United States Patent
Slovic et al.

(10) Patent No.: US 10,774,317 B2
(45) Date of Patent: Sep. 15, 2020

(54) ENGINEERED ENZYME HAVING ACETOACETYL-COA HYDROLASE ACTIVITY, MICROORGANISMS COMPRISING SAME, AND METHODS OF USING SAME

(71) Applicant: Braskem S.A., Camacari (BR)

(72) Inventors: Avram Michael Slovic, Camacari (BR); Iuri Estrada Gouvea, Camacari (BR); Daniel Johannes Koch, Camacari (BR); Felipe Galzerani, Camacari (BR)

(73) Assignee: BRASKEM S.A., Camacari (BR)

( * ) Notice: Subject to any disclaimer, the term of this patent is extended or adjusted under 35 U.S.C. 154(b) by 0 days.

(21) Appl. No.: 16/011,041

(22) Filed: Jun. 18, 2018

(65) Prior Publication Data

US 2018/0327727 A1 Nov. 15, 2018

Related U.S. Application Data

(62) Division of application No. 15/023,579, filed as application No. PCT/US2014/057020 on Sep. 23, 2014, now Pat. No. 10,000,744.

(60) Provisional application No. 61/881,267, filed on Sep. 23, 2013.

(51) Int. Cl.
*C12N 9/10* (2006.01)
*C12N 9/16* (2006.01)
*C12P 7/04* (2006.01)

(52) U.S. Cl.
CPC ............... *C12N 9/16* (2013.01); *C12N 9/13* (2013.01); *C12P 7/04* (2013.01); *C12Y 301/02011* (2013.01)

(58) Field of Classification Search
None
See application file for complete search history.

(56) References Cited

U.S. PATENT DOCUMENTS

| | | | |
|---|---|---|---|
| 2008/0293125 A1 | 11/2008 | Subbian et al. | |
| 2010/0261237 A1 | 10/2010 | Verseck et al. | |
| 2012/0322078 A1 | 12/2012 | McBride et al. | |
| 2015/0064759 A1 | 3/2015 | Perez et al. | |
| 2015/0064760 A1 | 3/2015 | Perez et al. | |

FOREIGN PATENT DOCUMENTS

| | | |
|---|---|---|
| EP | 2570485 | 3/2013 |
| WO | 2011/143592 A1 | 11/2011 |
| WO | 2012058603 | 5/2012 |
| WO | 2013/090915 A1 | 6/2013 |
| WO | 2015035226 | 3/2015 |
| WO | WO-2015035244 A1 * | 3/2015 ............... C12P 7/04 |

OTHER PUBLICATIONS

PCT International Preliminary Report on Patentability for International Application No. PCT/US2014/057020, dated Apr. 7, 2016, 8 pgs.
Flikweert et al., "Metabolic Responses of Pyruvate Decarboxylase-Negative *Saccaromyces cerevisiae* to Glucose Excess," Applied and Environmental Microbiology, 63(9):3399-3404, Sep. 1997.
Search Report for related International Application No. PCT/US2014/057020 dated Jan. 14, 2015 (4 pages).
Written Opinion for related International Application No. PCT/US2014/057020 dated Jan. 14, 2015 (6 pages).
PCT International Preliminary Report on Patentability for International Application No. PCT/US2014/057050, dated Apr. 7, 2016, 8 pgs.
Supplemental Partial European Search Report issued in related European Patent Application No. 14845077, dated Jan. 27, 2017, 5 pages.
Aftab Alam et al., "Aspects related to 3-Hydroxy-3-methylglutaryl-CoA synthesis in higher plants." Biochemical Society Transactions. Jan. 1, 1991 (Jan. 1, 1991). page 1645. XP055339953. Retrieved from the Internet: URI: http://www.biochemsoctrans.orgjcontent/19/2/164S.full.pdf [retrieved on Jan. 27, 2017.
Search Report issued in related European Patent Application No. 14845077.8 dated May 3, 2017.
Rangarajan et al., "Crystallographic Trapping of the Glutamyl-CoA Thioester Intermediate of Family I CoA Transferases", J. Biol. Chem. 280:42919-42928, 2005 (Year: 2005).
Dunn, B., "Engineered Enzymes", "Encyclopedia of Life Sciences", 2005, pp. 1-8 (Year: 2005).
Partial European Search Report and Provisional Opinion Accompanying the Partial Search Report issued in related European Patent Application No. 19164110.9, dated Jun. 28, 2019. 16 pages.

* cited by examiner

Primary Examiner — David Steadman
(74) Attorney, Agent, or Firm — K&L Gates LLP

(57) ABSTRACT

The disclosure provides engineered enzymes that are capable of mediating the conversion of acetoacetyl-CoA to acetoacetate that do not react with the same order of magnitude with acetyl-CoA as they do with acetoacetyl-CoA (e.g., the engineered enzymes have a specific acetoacetyl-CoA hydrolase activity at least 10× higher than its acetyl-CoA hydrolase activity). Additionally, the disclosure provides modified microorganisms that comprise the engineered enzymes disclosed herein and methods of using same.

12 Claims, 5 Drawing Sheets
Specification includes a Sequence Listing.

FIG. 3

| Uniprot Entry Name | Catalytic Glu location | Uniprot Acess | |
|---|---|---|---|
| ATOA_ECOLI | 41 ITLQS NGFL 50 | P76459 | SEQ ID NO: 40 |
| ATOA_HAEIN | 41 ITLQS NGFL 50 | P44874 | SEQ ID NO: 41 |
| CATJ_PSESB | 46 VVLIY SGPI 55 | Q8VPF2 | SEQ ID NO: 42 |
| CTFB_CLOAB | 46 ITFQS NGIV 55 | P23673 | SEQ ID NO: 43 |
| GCTB_ACIFV | 49 CHIIV SGLM 58 | Q59112 | SEQ ID NO: 44 |
| PCAJ_ACIAD | 45 VFLHS NGLL 54 | Q59091 | SEQ ID NO: 45 |
| PCAJ_PSEPK | 45 VFLHS NGLL 54 | P0A101 | SEQ ID NO: 46 |
| PCAJ_PSEPU | 45 VFLHS NGLL 54 | P0A102 | SEQ ID NO: 47 |
| SCOB_BACSU | 42 VMLQS NGLL 51 | P42316 | SEQ ID NO: 48 |
| SCOB_HELPJ | 38 IVFQS NGLL 47 | Q9ZLE4 | SEQ ID NO: 49 |
| SCOB_HELPY | 38 IVFQS NGLL 47 | P56007 | SEQ ID NO: 50 |
| SCOB_MYCBO | 45 VVLHS NGIL 54 | P63651 | SEQ ID NO: 51 |
| SCOB_MYCTU | 45 VVLHS NGIL 54 | P63650 | SEQ ID NO: 52 |
| SCOB_XANCB | 42 VWLQS NGLL 51 | B0RVK3 | SEQ ID NO: 53 |
| SCOB_XANCP | 42 VWLQS NGLL 51 | P0C7I8 | SEQ ID NO: 54 |
| Y3552_MYCTU | 46 ILLTDG AQL 55 | P63652 | SEQ ID NO: 55 |
| Y3582_MYCBO | 46 ILLTDG AQL 55 | P63653 | SEQ ID NO: 56 |
| YODR_BACSU | 45 VMFQA NGVL 54 | O34466 | SEQ ID NO: 57 |
| YDIF_ECOLI | 328 FILTV TGPI 337 | P37766 | SEQ ID NO: 58 |

ENGINEERED ENZYME HAVING ACETOACETYL-COA HYDROLASE ACTIVITY, MICROORGANISMS COMPRISING SAME, AND METHODS OF USING SAME

PRIORITY CLAIM

The present application is a divisional of U.S. application Ser. No. 15/023,579, filed on Mar. 21, 2016, which is a National Phase of International Application No. PCT/US2014/057020, filed on Sep. 23, 2014 which claims benefit of U.S. provisional patent application No. 61/881,267, filed on Sep. 23, 2013, the entire contents of each of which are being incorporated herein by reference.

BACKGROUND

The conversion of acetoacetyl-CoA to acetoacetate (FIG. 1) is an essential step in metabolic pathways with such intermediates. The specific hydrolysis of the thioester bond between coenzyme A (a thiol) and acetoacetate (an acyl group carrier) in acetoacetyl-CoA is an efficient way to produce the aforementioned conversion. Two classes of naturally occurring enzymes have been used to mediate such conversion including, CoA transferases (E.C. 2.8.3.-) and CoA-hydrolases (thioesterases) (E.C. 3.1.2.-). However, while acetoacetate-CoA transferases require the presence of a non-activated acid acting as CoA acceptor, the CoA-hydrolases (acyl-CoA thioesterases) described to act on acetoacetyl-CoA are unspecific in the sense that they react with the same order of magnitude with acetyl-CoA, the substrate required for acetoacetyl-CoA formation by the enzyme thiolase (E.C. 2.3.1.9), thereby degrading the substrate for the acetoacetyl-CoA biosynthesis itself.

Therefore, there exists a need in the art for improved enzymes to mediate the conversion of acetoacetyl-CoA to acetoacetate.

SUMMARY

The present disclosure provides engineered enzymes that are capable of mediating the conversion of acetoacetyl-CoA to acetoacetate that do not react with the same order of magnitude with acetyl-CoA as they do with acetoacetyl-CoA (e.g., the engineered enzymes have a specific acetoacetyl-CoA hydrolase activity at least 10× higher than its acetyl-CoA hydrolase activity).

The present disclosure also provides an engineered enzyme having acetoacetyl-CoA substrate specificity and acetoacetyl-CoA specific hydrolase activity.

In some embodiments of each or any of the above or below mentioned embodiments, the engineered enzyme comprises i) an amino acid sequence of an enzyme having acetoacetyl-CoA transferase activity; and ii) a substitution of a glutamic acid residue (i.e., the catalytic glutamic acid residue) to an aspartic acid residue at a position corresponding to amino acid position 51 of SEQ ID NO: 1, or a substitution of a glutamic acid residue to an aspartic acid residue at a position corresponding to amino acid position 46 of SEQ ID NO: 3, or a substitution of a glutamic acid residue to an aspartic acid residue at a position corresponding to amino acid position 333 of SEQ ID NO: 5.

In some embodiments of each or any of the above or below mentioned embodiments, the enzyme having acetoacetyl-CoA transferase activity is from an enzyme family having 3-oxoacid CoA-transferase activity.

In some embodiments of each or any of the above or below mentioned embodiments, the enzyme having acetoacetyl-CoA transferase activity is butyrate-acetoacetate CoA-transferase or acetate-acetoacetate-CoA transferase.

In some embodiments of each or any of the above or below mentioned embodiments, the enzyme having acetoacetyl-CoA transferase activity is from *Clostridium acetobutylicum*.

In some embodiments of each or any of the above or below mentioned embodiments, the engineered enzyme has the amino acid sequence as set forth in SEQ ID NO: 2.

In some embodiments of each or any of the above or below mentioned embodiments, the enzyme having acetoacetyl-CoA transferase activity is from *Escherichia coli*.

In some embodiments of each or any of the above or below mentioned embodiments, the engineered enzyme has the amino acid sequence as set forth in SEQ ID NO: 3.

In some embodiments of each or any of the above or below mentioned embodiments, the engineered enzyme has the amino acid sequence as set forth in SEQ ID NO: 5.

In some embodiments of each or any of the above or below mentioned embodiments, the engineered enzyme has a specific acetoacetyl-CoA hydrolase activity at least 10× higher than its acetyl-CoA hydrolase activity.

The present disclosure also provides an engineered enzyme having the amino acid sequence as set forth in SEQ ID NO: 2.

The present disclosure also provides a modified microorganism comprising one or more polynucleotides coding for one or more enzymes in a pathway with acetoacetate as an intermediate or end-product, and an engineered enzyme having acetoacetyl-CoA substrate specificity and acetoacetyl-CoA specific hydrolase activity.

In some embodiments of each or any of the above or below mentioned embodiments, the microorganism has a disruption in one or more polynucleotides that code for one or more enzymes that decarboxylate pyruvate or a disruption in one or more polynucleotides that code for a transcription factor of an enzyme that decarboxylates pyruvate.

In some embodiments of each or any of the above or below mentioned embodiments, the disruption in the one or more enzymes that decarboxylate pyruvate is a deletion or a mutation.

In some embodiments of each or any of the above or below mentioned embodiments, the one or more enzymes that decarboxylate pyruvate include pdc1, pdc 5, and/or pdc6, and wherein the one or more transcription factors of the one or more enzymes that decarboxylate pyruvate include pdc2.

In some embodiments of each or any of the above or below mentioned embodiments, the engineered enzyme comprises i) an amino acid sequence of an enzyme having acetoacetyl-CoA transferase activity and ii) a substitution of a glutamic acid residue to an aspartic acid residue at a position corresponding to amino acid position 51 of SEQ ID NO: 1.

In some embodiments of each or any of the above or below mentioned embodiments, the enzyme having acetoacetyl-CoA transferase activity is from an enzyme family having 3-oxoacid CoA-transferase activity.

In some embodiments of each or any of the above or below mentioned embodiments, the enzyme having acetoacetyl-CoA transferase activity is butyrateacetoacetate CoA-transferase or acetate-acetoacetate-CoA transferase.

In some embodiments of each or any of the above or below mentioned embodiments, the enzyme having acetoacetyl-CoA transferase activity is from *Clostridium acetobutylcum*.

In some embodiments of each or any of the above or below mentioned embodiments, the enzyme has the amino acid sequence as set forth in SEQ ID NO: 2.

In some embodiments of each or any of the above or below mentioned embodiments, the enzyme having acetoacetyl-CoA transferase activity is from *Escherichia coli*.

In some embodiments of each or any of the above or below mentioned embodiments, the engineered enzyme has the amino acid sequence as set forth in SEQ ID NO:4.

In some embodiments of each or any of the above or below mentioned embodiments, the engineered enzyme has the amino acid sequence as set forth in SEQ ID NO: 6.

In some embodiments of each or any of the above or below mentioned embodiments, the engineered enzyme has a specific acetoacetyl-CoA hydrolase activity at least 1 Ox higher than its acetyl-CoA hydrolase activity.

The present disclosure also provides a method of engineering an enzyme having acetoacetyl-CoA substrate specificity and acetoacetyl-CoA specific hydrolase activity, the method comprising: a) selecting an enzyme having acetoacetyl-CoA transferase activity, and b) substituting a glutamic acid residue to an aspartic acid residue at a position corresponding to amino acid position 51 of SEQ ID NO: 1 in the enzyme having acetoacetyl-CoA transferase activity to produce an engineered enzyme.

In some embodiments of each or any of the above or below mentioned embodiments, the substitution is introduced via site directed mutagenesis.

In some embodiments of each or any of the above or below mentioned embodiments, the enzyme having acetoacetyl-CoA transferase activity is from an enzyme family having 3-oxoacid CoA-transferase activity.

In some embodiments of each or any of the above or below mentioned embodiments, the enzyme having acetoacetyl-CoA transferase activity is butyrateacetoacetate CoA-transferase.

In some embodiments of each or any of the above or below mentioned embodiments, the enzyme having acetoacetyl-CoA transferase activity is from *Clostridium acetobutylicum* or *Escherichia coli*.

In some embodiments of each or any of the above or below mentioned embodiments, the engineered enzyme has a specific acetoacetyl-CoA hydrolase activity at least 10× higher than its acetyl-CoA hydrolase activity.

The present disclosure also provides a method of producing one or more products from a fermentable carbon source, said method comprising: a.) providing a fermentable carbon source; and b.) contacting the fermentable carbon source with the modified microorganism as disclosed herein in a fermentation media, wherein the microorganism produces one or more products from the fermentable carbon source.

In some embodiments of each or any of the above or below mentioned embodiments, the carbon source is contacted with the modified microorganism under anaerobic conditions.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

FIG. 3 depicts an alignment of 3-oxoacid CoA-transferases illustrating the identification and location of the active glutamic acid residue.

DETAILED DESCRIPTION

Figure 1:
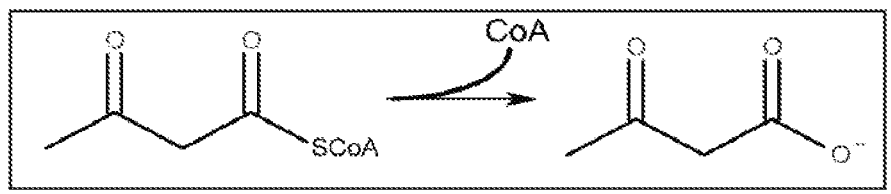
FIG. 1 depicts a reaction scheme for the formation of acetoacetate through hydrolysis of acetoacetyl-CoA.
Figure 2:
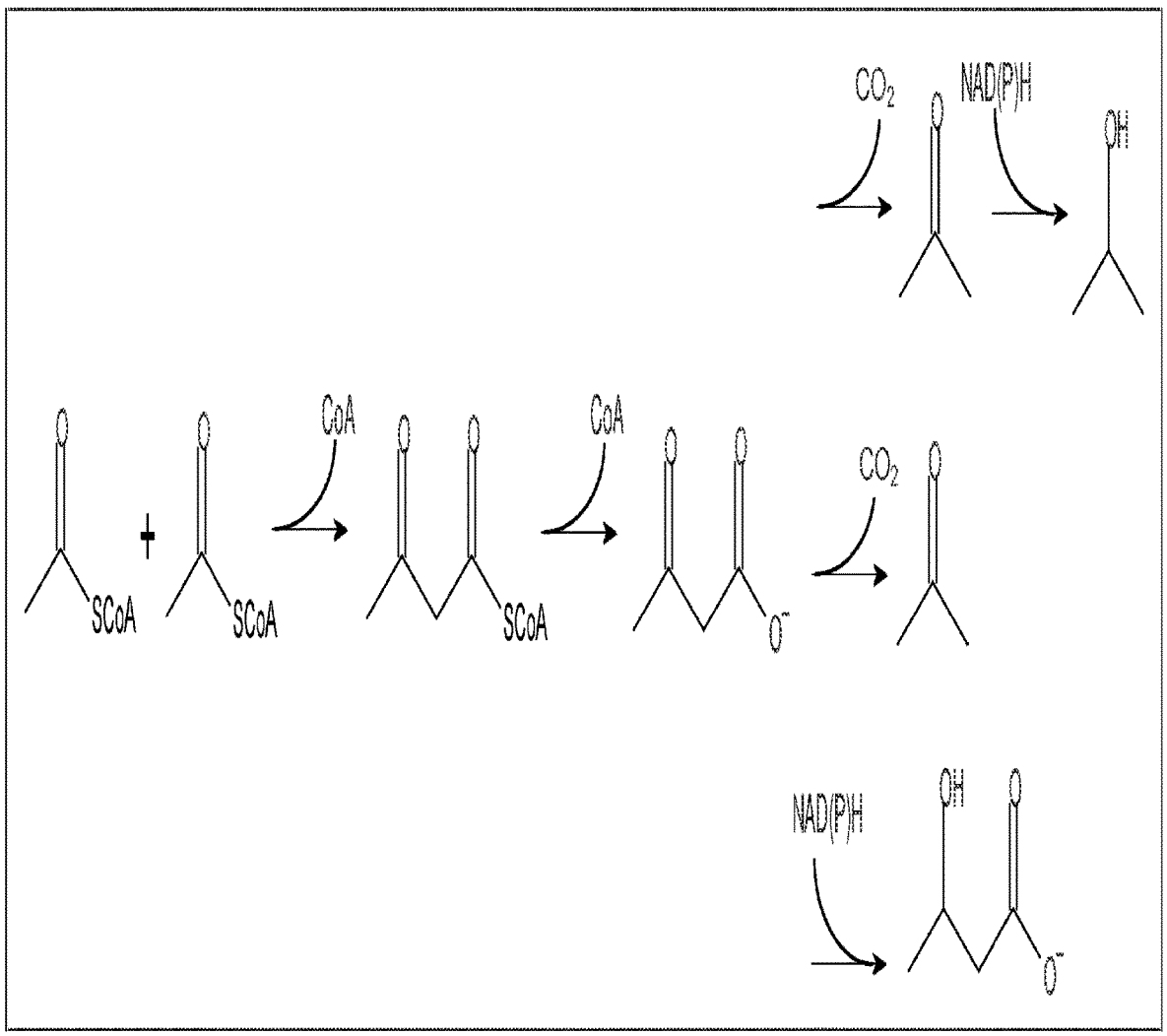
FIG. 2 depicts reaction schemes for metabolic pathways with the intermediates acetoacetyl-CoA and acetoacetate.

The conversion of acetoacetyl-CoA to acetoacetate (FIG. 1) is an essential step in metabolic pathways with such intermediates including, for example, pathways for the production of 3-hydroxy-butyrate, acetone or isopropanol (FIG. 2). However, no acetoacetyl-CoA specific hydrolase is known that can produce acetoacetate and regenerate free CoA without degrading acetyl-CoA, the substrate for the acetoacetylCoA biosynthesis itself. The present disclosure provides the rational engineering of a 3-oxoacid CoA-transferase with acetoacetyl-CoA substrate specificity (e.g., a butyrateacetoacetate CoA-transferase—SEQ ID NO: 1; a acetate-acetoacetate CoA-transferaseSEQ ID NO: 2; or Acetate CoA-transferase—SEQ ID NO: 3) to an acetoacetyl-CoA specific hydrolase and its use in metabolic pathways utilizing acetoacetate as an intermediate or an end-product including, for example, pathways for the synthesis of 3-hydroxy-butyrate, acetone and/or isopropanol. The engineered enzyme has a higher activity on acetoacetyl-CoA versus acetyl-CoA (e.g., 1 Ox, 15×, 20×, 25×, 30×, 35×, 40×, 45×, 50×, or more). The engineered enzyme may comprise: i) an amino acid sequence of an enzyme having acetoacetyl-CoA transferase activity and ii) a substitution of a glutamic acid residue to an aspartic acid residue at a position corresponding to amino acid position 51 of SEQ ID NO: 1, or a substitution of a glutamic acid residue to an aspartic acid residue at a position corresponding to amino acid position 46 of SEQ ID NO: 3, or a substitution of a glutamic acid residue to an aspartic acid residue at a position corresponding to amino acid position 333 of SEQ ID NO: 5; and have a specific acetoacetyl-CoA hydrolase activity at least 10× higher than its acetyl-CoA hydrolase activity. Exemplary 3-oxoacid CoA-transferases are listed in FIG. 3 as well as the location of the active glutamic acid residue that may be substituted to an aspartic acid residue to engineer an enzyme having acetoacetyl-CoA specific hydrolase activity.

The engineered acetoacetyl-CoA hydrolase disclosed herein solves the problem that no acetoacetyl-CoA specific hydrolase is known that can produce acetoacetate and regenerate free CoA. Natural wild type hydrolases are known to accept several acid CoA compounds with similar activities and can be expected to be very difficult to be engineered for such specificity. Thus, naturally occurring and known enzymes with acetoacetyl-CoA hydrolase activity suggested previously (see, US 2010/0261237 A 1) create the problem of unspecific acid-CoA (e.g., acetyl-CoA) hydrolase activity. Such enzymes destroy the precursor necessary for the formation of their own substrate, i.e. acetoacetyl-CoA generation from two acetyl-CoA by thiolase enzyme. As a result, their use in metabolic pathways containing further acid-CoA intermediates is highly inefficient.

Additionally, the engineered acetoacetyl-CoA hydrolase disclosed herein solves the problem of requiring an acceptor molecule and processing another acid-CoA intermediate. Appropriate transferase enzymes for the enzymatic removal of the CoA group from acetoacetyl-CoA are typically specific. However, the reaction requires an acceptor acid molecule and yields a further acid-CoA compound that needs to be processed for regeneration of free CoA. Removing the necessity of an acceptor molecule enables the creation of simplified, usually more efficient pathways.

Furthermore, transferases already described to accept acetoacetyl-CoA as substrate have a Km value for the acceptor molecule that is above 10 mM which is about 1000 times higher than the Km value for the acetoacetyl-CoA donor substrate. So the acceptor concentration is a limiting factor of the transferase reaction. Utilizing an acetoacetyl-CoA hydrolase engineered from an acetoacetyl-CoA transferase (i.e., a 3-oxoacid CoA-transferase that accepts Acetoacetyl-CoA as a CoA donor) has the added benefit of a very low Km for the substrate acetoacetyl-CoA. This allows hydrolysis of acetoacetyl-CoA with a high reaction rate at low substrate concentrations and therefore can prevent accumulation of acetoacetyl-CoA and establish a "pull" on the preceding, thiolase mediated reversible acetoacetyl-CoA biosynthesis reaction. Since the thiolase reaction often represents a rate limiting step in a biosynthesis, such a pull can be highly beneficial for the performance of the entire appropriate metabolic pathway.

The invention disclosed herein has particular importance in the context of a microorganism such as *Saccharomyces cerevisiase* strain that has the pyruvate decarbolylase genes (e.g., PDC1, PDC5 and PDC6) disrupted and/or deleted. In this strain, the reaction catalyzed by this enzyme, namely the conversion of pyruvate to acetaldehyde and $CO_2$ does not occur. The result of such a deletion is that acetaldehyde cannot be further reduced by alcohol dehydrogenase to make ethanol, and thus such strain is deemed ethanol null. A secondary effect of such a deletion is that such a strain also does not produce acetic acid, which in the 2-propanol pathway described herein (see, e.g., Table 3 and FIGS. 4 and 5), is an essential receptor for a CoA which is transferred from acetoacetyl-CoA as it is converted to acetoacetate by a transferase. Thus, in the absence of a CoA receptor for such a reaction, it is impossible to remove the CoA from acetoacetylCoA, and the pathway cannot advance to 2-propanol. Pyruvate decarbolylase null yeast strains modified to produce 2-propanol thus require either exogenous acetate to receive the CoA from acetoacetyl-CoA, or require the activity of an enzyme such as a hydrolase to remove such a CoA from acetoacetyl-CoA. The hydrolase thus proposed has practical application in the context of such a strain which is unable to produce acetic acid, but requires a manner to convert acetoacetyl-CoA to acetoacetate.

Microorganisms disclosed herein with an engineered acetoacetyl-CoA specific hydrolase may also be modified to have a disruption in one or more polynucleotides that code for one or more enzymes that decarboxylate pyruvate or a disruption in one or more polynucleotides that code for a transcription factor of an enzyme that decarboxylates pyruvate. In an embodiment, the disruption in the one or more enzymes that decarboxylate pyruvate is a deletion or a mutation. In a further embodiment, the one or more enzymes that decarboxylate pyruvate include pdc1, pdc 5, and/or pdc6, and the one or more transcription factors of the one or more enzymes that decarboxylate pyruvate include pdc2. The microorganism may additionally comprise one or more exogenous polynucleotides encoding one or more enzymes in pathways for the coproduction of 1-propanol and/or 2-propanol from a fermentable carbon source under anaerobic conditions.

As used herein, the term "biological activity" or "functional activity," when referring to a protein, polypeptide or peptide, may mean that the protein, polypeptide or peptide exhibits a functionality or property that is useful as relating to some biological process, pathway or reaction. Biological or functional activity can refer to, for example, an ability to interact or associate with (e.g., bind to) another polypeptide or molecule, or it can refer to an ability to catalyze or regulate the interaction of other proteins or molecules (e.g., enzymatic reactions).

As used herein, the term "culturing" may refer to growing a population of cells, e.g., microbial cells, under suitable conditions for growth, in a liquid or on solid medium.

As used herein, the term "derived from" may encompass the terms originated from, obtained from, obtainable from, isolated from, and created from, and generally indicates that one specified material finds its origin in another specified material or has features that can be described with reference to the another specified material.

As used herein, "exogenous polynucleotide" refers to any deoxyribonucleic acid that originates outside of the microorganism.

As used herein, the term "an expression vector" may refer to a DNA construct containing a polynucleotide or nucleic acid sequence encoding a polypeptide or protein, such as a DNA coding sequence (e.g. gene sequence) that is operably linked to one or more suitable control sequence(s) capable of affecting expression of the coding sequence in a host. Such control sequences include a promoter to affect transcription, an optional operator sequence to control such transcription, a sequence encoding suitable mRNA ribosome binding sites, and sequences which control termination of transcription and translation. The vector may be a plasmid, cosmid, phage particle, bacterial artificial chromosome, or simply a potential genomic insert. Once transformed into a suitable host, the vector may replicate and function independently of the host genome (e.g., independent vector or plasmid), or may, in some instances, integrate into the genome itself (e.g., integrated vector). The plasmid is the most commonly used form of expression vector. However, the disclosure is intended to include such other forms of expression vectors that serve equivalent functions and which are, or become, known in the art.

As used herein, the term "expression" may refer to the process by which a polypeptide is produced based on a nucleic acid sequence encoding the polypeptides (e.g., a gene). The process includes both transcription and translation.

As used herein, the term "gene" may refer to a DNA segment that is involved in producing a polypeptide or protein (e.g., fusion protein) and includes regions preceding and following the coding regions as well as intervening sequences (introns) between individual coding segments (exons).

As used herein, the term "heterologous," with reference to a nucleic acid, polynucleotide, protein or peptide, may refer to a nucleic acid, polynucleotide, protein or peptide that does not naturally occur in a specified cell, e.g., a host cell. It is intended that the term encompass proteins that are encoded by naturally occurring genes, mutated genes, and/or synthetic genes. In contrast, the term homologous, with reference to a nucleic acid, polynucleotide, protein or peptide, refers to a nucleic acid, polynucleotide, protein or peptide that occurs naturally in the cell.

As used herein, the term a "host cell" may refer to a cell or cell line, including a cell such as a microorganism which a recombinant expression vector may be transfected for expression of a polypeptide or protein (e.g., fusion protein). Host cells include progeny of a single host cell, and the progeny may not necessarily be completely identical (in morphology or in total genomic DNA complement) to the original parent cell due to natural, accidental, or deliberate mutation. A host cell may include cells transfected or transformed in vivo with an expression vector.

As used herein, the term "introduced," in the context of inserting a nucleic acid sequence or a polynucleotide sequence into a cell, may include transfection, transformation, or transduction and refers to the incorporation of a nucleic acid sequence or polynucleotide sequence into a eukaryotic or prokaryotic cell wherein the nucleic acid sequence or polynucleotide sequence may be incorporated into the genome of the cell (e.g., chromosome, plasmid, plastid, or mitochondrial DNA), converted into an autonomous replicon, or transiently expressed.

As used herein, the term "non-naturally occurring" or "modified" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Non-naturally occurring microbial organisms of the disclosure can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely. Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

As used herein, the term "operably linked" may refer to a juxtaposition or arrangement of specified elements that allows them to perform in concert to bring about an effect. For example, a promoter may be operably linked to a coding sequence if it controls the transcription of the coding sequence.

As used herein, "1-propanol" is intended to mean n-propanol with a general formula $CH_3CH_2CH_2OH$ (CAS number—71-23-8).

As used herein, "2-propanol" is intended to mean isopropyl alcohol with a general formula $CH_3CH_3CHOH$ (CAS number—67-63-0).

As used herein, the term "a promoter" may refer to a regulatory sequence that is involved in binding RNA polymerase to initiate transcription of a gene. A promoter may be an inducible promoter or a constitutive promoter. An inducible promoter is a promoter that is active under environmental or developmental regulatory conditions.

As used herein, the term "a polynucleotide" or "nucleic acid sequence" may refer to a polymeric form of nucleotides of any length and any three-dimensional structure and single- or multi-stranded (e.g., single-stranded, double-stranded, triplehelical, etc.), which contain deoxyribonucleotides, ribonucleotides, and/or analogs or modified forms of deoxyribonucleotides or ribonucleotides, including modified nucleotides or bases or their analogs. Such polynucleiotides or nucleic acid sequences may encode amino acids (e.g., polypeptides or proteins such as fusion proteins). Because the genetic code is degenerate, more than one codon may be used to encode a particular amino acid, and the present disclosure encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms polynucleotide, nucleic acid, and oligonucleotide are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S (thioate), P(S)S (dithioate), (O)NR$_2$ (amidate), P(O)R, P(O)OR', COCH$_2$ (formacetal), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, the term a "protein" or "polypeptide" may refer to a composition comprised of amino acids and recognized as a protein by those of skill in the art. The conventional one-letter or three-letter code for amino acid residues is used herein. The terms protein and polypeptide are used interchangeably herein to refer to polymers of amino acids of any length, including those comprising linked (e.g., fused) peptides/polypeptides (e.g., fusion proteins). The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, related proteins, polypeptides or peptides may encompass variant proteins, polypeptides or peptides. Variant proteins, polypeptides or peptides differ from a parent protein, polypeptide or peptide and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence.

As used herein, the term "recovered," "isolated," "purified," and "separated" may refer to a material (e.g., a protein, peptide, nucleic acid, polynucleotide or cell) that is removed from at least one component with which it is naturally associated. For example, these terms may refer to a material which is substantially or essentially free from components which normally accompany it as found in its native state, such as, for example, an intact biological system.

As used herein, the term "recombinant" may refer to nucleic acid sequences or polynucleotides, polypeptides or proteins, and cells based thereon, that have been manipulated by man such that they are not the same as nucleic acids, polypeptides, and cells as found in nature. Recombinant may also refer to genetic material (e.g., nucleic acid sequences or polynucleotides, the polypeptides or proteins they encode, and vectors and cells comprising such nucleic acid sequences or polynucleotides) that has been modified to alter its sequence or expression characteristics, such as by mutating the coding sequence to produce an altered polypeptide, fusing the coding sequence to that of another coding sequence or gene, placing a gene under the control of a different promoter, expressing a gene in a heterologous organism, expressing a gene at decreased or elevated levels, expressing a gene conditionally or constitutively in manners different from its natural expression profile, and the like.

As used herein, the term "selective marker" or "selectable marker" may refer to a gene capable of expression in a host cell that allows for ease of selection of those hosts containing an introduced nucleic acid sequence, polynucleotide or vector. Examples of selectable markers include but are not limited to antimicrobial substances (e.g., hygromycin, bleomycin, or chloramphenicol) and/or genes that confer a metabolic advantage, such as a nutritional advantage, on the host cell.

As used herein, the term "substantially anaerobic" means that growth of the modified microorganism takes place in culture media that comprises a dissolved oxygen concentration of less than 5 ppm.

As used herein, the term "substantially similar" and "substantially identical" in the context of at least two nucleic acids, polynucleotides, proteins or polypeptides may mean that a nucleic acid, polynucleotide, protein or polypeptide comprises a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) nucleic acid, polynucleotide, protein or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:1 0915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448). In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

As used herein, the term "transfection" or "transformation" may refer to the insertion of an exogenous nucleic acid or polynucleotide into a host cell. The exogenous nucleic acid or polynucleotide may be maintained as a non-integrated vector, for example, a plasmid, or alternatively, may be integrated into the host cell genome. The term transfecting or transfection is intended to encompass all conventional techniques for introducing nucleic acid or polynucleotide into host cells. Examples of transfection techniques include, but are not limited to, calcium phosphate precipitation, DEAE-dextranmediated transfection, lipofection, electroporation, and microinjection.

As used herein, the term "transformed," "stably transformed," and "transgenic" may refer to a cell that has a non-native (e.g., heterologous) nucleic acid sequence or polynucleotide sequence integrated into its genome or as an episomal plasmid that is maintained through multiple generations.

As used herein, the term "vector" may refer to a polynucleotide sequence designed to introduce nucleic acids into one or more cell types. Vectors include cloning vectors, expression vectors, shuttle vectors, plasmids, phage particles, single and double stranded cassettes and the like.

As used herein, the term "wild-type," "native," or "naturally-occurring" proteins may refer to those proteins found in nature. The terms wild-type sequence refers to an amino acid or nucleic acid sequence that is found in nature or naturally occurring. In some embodiments, a wild-type sequence is the starting point of a protein engineering project, for example, production of variant proteins.

Unless defined otherwise herein, all technical and scientific terms used herein have the same meaning as commonly understood by one of ordinary skill in the art to which this disclosure belongs. Singleton, et al., Dictionary of Microbiology and Molecular Biology, second ed., John Wiley and Sons, New York (1994), and Hale & Markham, The Harper Collins Dictionary of Biology, Harper Perennial, NY (1991) provide one of skill with a general dictionary of many of the terms used in this disclosure. Further, it will be understood that any of the substrates disclosed in any of the pathways herein may alternatively include the anion or the cation of the substrate.

Numeric ranges provided herein are inclusive of the numbers defining the range.

Unless otherwise indicated, nucleic acids sequences are written left to right in 5' to 3' orientation; amino acid sequences are written left to right in amino to carboxy orientation, respectively.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Engineering of Acetoacetyl-CoA Hydrolase

A transferase with acetoacetyl-CoA substrate specificity may be engineered to produce an acetoacetyl-CoA specific hydrolase. The disclosure contemplates that any method known in the art may be used to modify a transferase with acetoacetyl-CoA substrate specificity including, for example, site directed mutagenesis. In an embodiment, the transferase with acetoacetyl-CoA substrate specificity may be modified to comprise a substitution of a glutamic acid residue to an aspartic acid residue at a position corresponding to amino acid position 51 of SEQ ID NO: 1. The engineered enzyme may be subjected to further mutagenesis (e.g., random mutagenesis) to further increase its hydrolase activity.

The present disclosure also provides a method of engineering an enzyme having acetoacetyl-CoA substrate specificity and acetoacetyl-CoA specific hydrolase activity, the method comprising: a) selecting an enzyme having acetoacetyl-CoA transferase activity, and b) substituting a glutamic acid residue to an aspartic acid residue at a position corresponding to amino acid position 51 of SEQ ID NO: 1 in the enzyme having acetoacetyl-CoA transferase activity to produce an engineered enzyme.

In an embodiment of the disclosure, an active site glutamate residue at position 51 of SEQ ID NO: 1, or an active site glutamic acid residue at position 46 of SEQ ID NO: 3, or an active site glutamic acid residue at position 333 of SEQ ID NO: 5, is substituted with an aspartate residue using site direct mutagenesis to generate a CoA hydrolase (i.e., a thioesterase) with higher activity on acetoacetyl-CoA versus acetyl-CoA.

Alternatively, in an embodiment of the disclosure an acetoacetyl-CoA hydrolase may be engineered from a transferase by directed evolution. In an exemplary method, libraries of at least partially random mutated acetoacetyl-CoA transferases are created and a mutant with the desired hydrolase activity is identified through appropriate screening and selection methods (i.e. detection of free CoA after contacting enzyme variant with acetoacetyl-CoA, but without acceptor molecule). Such a method can result in other mutations than an exchange of the active glutamate acid residue to result in hydrolase activity. For instance, the three dimensional structure of the protein could get changed in such a way, that the distance between substrate and acid group of the active glutamic acid residue is increased to the same extent as in a replacement of the active glutamic acid with an aspartic acid residue, with similar effects on enzyme activity.

It will be appreciated by one of skill in the art that the active site glutamate residue of an enzyme with acetoacetyl-CoA transferase activity can be readily identified in any known transferase (see, Table 1) by sequence alignment of such enzyme with SEQ ID NO: 1 and that any known transferase can be modified to produce an acetoacetyl-CoA specific hydrolase. Such an alignment permits the identification of the glutamic acid residue at a position corresponding to amino acid position 51 of SEQ ID NO: 1 to be substituted with an aspartic acid residue. It will also be appreciated that not all transferases can accept acetoacetyl-CoA as a substrate. As such, those transferases that can accept acetoacetyl-CoA as a substrate are preferred for use in the methods of the disclosure. Optionally, the engineered acetoacetyl-CoA specific hydrolase may be further modified by any methods known in the art including, by random mutagenesis, to increase hydrolase activity.

Exemplary enzymes suitable to accept acetoacetyl-CoA as substrate are set forth in Table 2 and are found among the subfamily of transferases acting at 3-oxoacids (Table 1). These enzymes can be engineered to not consume the equimolar amount of the acceptor acid molecule as co-substrate, but instead perform the hydrolysis of the thioester bound and liberate acetoacetate and free Coenzyme A (HCoA) as products. With the exception of Uniprot No. P37766 (this sequence is a fusion of an alpha and beta subunit), Table 1 lists the beta subunit of a CoA-transferase. CoA-transferases are comprised of an alpha subunit and a beta subunit, and as such, those beta subunits listed in Table 1 must be combined with an alpha subunit in order to produce a catalytically active CoA-transferase. It will be understood that the CoA-transferase beta subunits listed in Table 1 may be combined with any known CoA-transferase alpha subunit that renders the combination of the beta subunit and alpha subunit catalytically active.

TABLE 1

Exemplary 3-oxoacid CoA-transferases.

| Protein Name | Gene Name | Organism | Uniprot | Uniprot Entry Name | Catalytic Glu |
|---|---|---|---|---|---|
| Acetate CoA-transferase subunit beta | atoA | *Escherichia coli* (strain K12) | P76459 | ATOA_ECOLI | E46 |

TABLE 1-continued

Exemplary 3-oxoacid CoA-transferases.

| Protein Name | Gene Name | Organism | Uniprot | Uniprot Entry Name | Catalytic Glu |
|---|---|---|---|---|---|
| Acetate CoA-transferase | YdiF | *Escherichia coli* (strain K12) | P37766 | YDIF_ECOLI | E333 |
| Acetate CoA-transferase subunit beta | atoA | *Haemophilus influenzae* | P44874 | ATOA_HAEIN | E46 |
| 3-oxoadipate CoA-transferase subunit B | catJ | *Pseudomonas* sp. | Q8VPF2 | CATJ_PSESB | E51 |
| Butyrate-acetoacetate CoA-transferase subunit B | ctfB | *Clostridium acetobutylicum* | P23673 | CTFB_CLOAB | E51 |
| Glutaconate CoA-transferase subunit B | gctB | *Acidaminococcus fermentans* (strain ATCC 25085/DSM 20731/VR4) | Q59112 | GCTB_ACIFV | E54 |
| 3-oxoadipate CoA-transferase subunit | pcaJ catJ | *Acinetobacter* sp. (strain ADP1) | Q59091 | PCAJ_ACIAD | E50 |
| 3-oxoadipate CoA-transferase subunit | pcaJ | *Pseudomonas putida* (strain KT2440) | P0A101 | PCAJ_PSEPK | E50 |
| 3-oxoadipate CoA-transferase subunit | pcaJ | *Pseudomonas putida* (*Arthrobacter siderocapsulatus*) | P0A102 | PCAJ_PSEPU | E50 |
| Probable succinyl-CoA:3-ketoacid coenzyme A | scoB | *Bacillus subtilis* (strain 168) | P42316 | SCOB_BACSU | E47 |
| Succinyl-CoA:3-ketoacid coenzyme A transferase | scoB | *Helicobacter pylori* (strain J99) (*Campylobacter pylori* J99) | Q9ZLE4 | SCOB_HELPJ | E43 |
| Succinyl-CoA:3-ketoacid coenzyme A transferase | scoB | *Helicobacter pylori* (strain ATCC 700392/ 26695) (*Campylobacter pylori*) | P56007 | SCOB_HELPY | E43 |
| Probable succinyl-CoA:3-ketoacid coenzyme A transferase | scoB | *Mycobacterium bovis* (strain ATCC BAA-935/ AF2122/97) | P63651 | SCOB_MYCBO | E50 |
| Probable succinyl-CoA:3-ketoacid coenzyme A transferase | scoB | *Mycobacterium tuberculosis* | P63650 | SCOB_MYCTU | E50 |
| Succinyl-CoA:3-ketoacid coenzyme A transferase | lpsJ | *Xanthomonas campestris* pv. *campestris* (strain B100) | B0RVK3 | SCOB_XANCB | E47 |

TABLE 1-continued

Exemplary 3-oxoacid CoA-transferases.

| Protein Name | Gene Name | Organism | Uniprot | Uniprot Entry Name | Catalytic Glu |
|---|---|---|---|---|---|
| Succinyl-CoA:3-ketoacid coenzyme A transferase | IpsJ | Xanthomonas campestris pv. campestris (strain ATCC 33913/ NCPPB 528/ LMG 568) | POC718 | SCOB_XANCP | E47 |
| Putative CoA-transferase subunit beta Rv3552 | Rv3552 | Mycobacterium tuberculosis | P63652 | Y3552_MYCTU | E52 |
| Putative CoA-transferase subunit beta Mb3582 | Mb3582 | Mycobacterium bovis (strain ATCC BAA-935/ AF2122/97) | P63653 | Y3582_MYCBO | E52 |
| Probable coenzyme A transferase subunit beta | yodR | Bacillus subtilis (strain 168) | O34466 | YODR_BACSU | E50 |

TABLE 2

Exemplary 3-oxoacid CoA-transferases able to accept acetoacetyl-CoA as substrate.

| Protein Names | Gene Names | Organism | Uniprot | Entry Name |
|---|---|---|---|---|
| Acetate CoA-transferase subunit beta | atoA | Escherichia coli (strain K12) | P76459 | ATOA_ECOLI |
| Acetate CoA-transferase | YdiF | Escherichia coli | P37766 | YDIF_ECOLI |
| Butyrate-acetoacetate CoA-transferase subunit B | ctfB | Clostridium acetobutylicum | P23673 | CTFB_CLOAB |
| Probable succinyl-CoA:3-ketoacid coenzyme A transferase | scoB | Bacillus subtilis (strain 168) | P42316 | SCOB_BACSU |

Modification of Microorganism

A microorganism may be modified (e.g., genetically engineered) by any method known in the art to comprise and/or express one or more polynucleotides coding for enzymes in a pathway that catalyze a conversion of a fermentable carbon source to one or more products. Such microorganism may comprise a polynucleotide coding for an engineered enzyme having acetoacetyl-CoA substrate specificity and acetoacetyl-CoA specific hydrolase activity (e.g., an enzyme that comprises i) an amino acid sequence of an enzyme having acetoacetyl-CoA transferase activity and ii) a substitution of a glutamic acid residue to an aspartic acid residue at a position corresponding to amino acid position 51 of SEQ ID NO: 1).

Pathways that utilize an engineered enzyme having acetoacetyl-CoA substrate specificity and acetoacetyl-CoA specific hydrolase activity are shown below. Such pathways are merely exemplary and represent a few of the ways in which the engineered enzyme disclosed herein may be exploited to catalyze the conversion of a fermentable carbon source to one or more desired end-products.

In some embodiments, a microorganism may be modified (e.g., genetically engineered) by any method known in the art to comprise and/or express one or more polynucleotides coding for enzymes in a pathway that catalyze a conversion of a fermentable carbon source to intermediates in a pathway for the co-production of 1-propanol and 2-propanol. Such enzymes may include any of those enzymes as set forth in FIG. 4 or 5. For example, the microorganism may be modified to comprise one or more polynucleotides coding for enzymes that catalyze a conversion of dihydroxyacetone phosphate or pyruvate to 1-propanol.

In some embodiments, the microorganism may comprise one or more exogenous polynucleotides encoding one or more enzymes in pathways for the co-production of 1-propanol and 2-propanol from a fermentable carbon source under anaerobic conditions.

In some embodiments, the microorganism may comprise one or more polynucleotides coding for enzymes in a pathway that catalyzes a conversion of pyruvate to 2-propanol including, for example, one or more polynucleotides coding for enzymes in a pathway that catalyze a conversion of pyruvate to acetyl-CoA, one or more polynucleotides coding for enzymes in a pathway that catalyze a conversion of acetyl-CoA to acetoacetyl-CoA, one or more polynucleotides coding for enzymes in a pathway that catalyze a conversion of acetoacetyl-CoA to acetoacetate, one or more polynucleotides coding for enzymes in a pathway that catalyze a conversion of acetoacetate to acetone, and/or one or more polynucleotides coding for enzymes in a pathway that catalyze a conversion of acetone to 2-propanol. Enzymes catalyzing any of these conversions may include, for example, those enzymes listed in Table 3.

In some embodiments, the non-naturally occurring microorganism may comprise one or more polynucleotides coding for enzymes in a pathway that catalyzes a conversion of dihydroxyacetone-phosphate to 1-propanol including, for example—one or more polynucleotides coding for enzymes in a pathway that catalyze a conversion of dihydroxyacetone-phosphate to methylglyoxal, one or more polynucleotides coding for enzymes in a pathway that catalyze a conversion of methylglyoxal to hydroxyacetone, one or more polynucleotides coding for enzymes in a pathway that catalyze a conversion of hydroxyacetone to 1,2-propanediol, one or more polynucleotides coding for enzymes in a pathway that catalyze a conversion of methylglyoxal to lactaldehyde, one or more polynucleotides coding for enzymes in a pathway that catalyze a conversion of lactaldehyde to 1,2-propanediol, one or more polynucleotides coding for enzymes in a pathway that catalyze a conversion of 1,2-propanediol to propionaldehyde, and/or one or more polynucleotides coding for enzymes in a pathway that catalyze a conversion of propionaldehyde to 1-propanol. Enzymes catalyzing any of these conversions may include, for example, those enzymes listed in Table 4.

In some embodiments, the non-naturally occurring microorganism may comprise one or more polynucleotides coding for enzymes in a pathway that catalyzes a conversion of lactate to 1-propanol including, for example, one or more polynucleotides coding for enzymes in a pathway that catalyze a conversion of lactate to lactoyl-CoA, one or more polynucleotides coding for enzymes in a pathway that catalyze a conversion of lactoyl-CoA to lactaldehyde, one or more polynucleotides coding for enzymes in a pathway that catalyze a conversion of lactaldehyde to 1,2-propanediol, one or more polynucleotides coding for enzymes in a pathway that catalyze a conversion of 1,2-propanediol to propionaldehyde, and/or one or more polynucleotides coding for enzymes in a pathway that catalyze a conversion of propionaldehyde to 1-propanol. Enzymes catalyzing any of these conversions may include, for example, those enzymes listed in Table 5.

A modified microorganism as provided herein may comprise:
    one or more polynucleotides coding for enzymes in a pathway that catalyzes a conversion of lactate to pyruvate,
    one or more polynucleotides coding for enzymes in a pathway that catalyzes a conversion of pyruvate to cytosolic acetyl-CoA,
    one or more polynucleotides coding for enzymes in a pathway that catalyzes a conversion of acetyl-CoA to acetoacetyl-CoA,
    one or more polynucleotides coding for enzymes in a pathway that catalyzes a conversion of acetoacetyl-CoA to AcAcetate,
    one or more polynucleotides coding for enzymes in a pathway that catalyzes a conversion of AcAcetate to acetone,
    one or more polynucleotides coding for enzymes in a pathway that catalyzes a conversion of acetone to 2-propanol,
    one or more polynucleotides coding for enzymes in a pathway that catalyzes a conversion of dihydroxyacetone phosphate to methylglyoxal,
    one or more polynucleotides coding for enzymes in a pathway that catalyzes a conversion of methylglyoxal to lactaldehyde,
    one or more polynucleotides coding for enzymes in a pathway that catalyzes a conversion of methylglyoxal to hydroxyacetone,
    one or more polynucleotides coding for enzymes in a pathway that catalyzes a conversion of hydroxyacetone to 1,2-propanediol,
    one or more polynucleotides coding for enzymes in a pathway that catalyzes a conversion of lactaldehyde to 1,2-propanediol,
    one or more polynucleotides coding for enzymes in a pathway that catalyzes a conversion of 1,2-propanediol to propionaldehyde, and/or
    one or more polynucleotides coding for enzymes in a pathway that catalyzes a conversion of propionaldehyde to 1-propanol.

In some embodiments, the modified microorganism has a disruption in each of the one or more polynucleotides that code for enzymes that decarboxylate pyruvate and associated transcription factor (e.g., pyruvate decarboxylase 1, 2, 5, and 6). In some embodiments, the modified microorganism is capable of growth on a C6 carbon source under anaerobic conditions. In some embodiments, the modified microorganism has a disruption in each of the one or more polynucleotides that code for enzymes that decarboxylate pyruvate and associated transcription factor (e.g., pyruvate decarboxylase 1, 2, 5, and 6) and is capable of growth on a C6 carbon source under anaerobic conditions.

A modified microorganism as provided herein may comprise:
    one or more polynucleotides coding for enzymes in a pathway that catalyzes a conversion of pyruvate to lactate,
    one or more polynucleotides coding for enzymes in a pathway that catalyzes a conversion of lactate to lactoyl-CoA,
    one or more polynucleotides coding for enzymes in a pathway that catalyzes a conversion of lactoyl-CoA to lactaldehyde,
    one or more polynucleotides coding for enzymes in a pathway that catalyzes a conversion of lactate and acetyl-CoA to lactoyl-CoA and acetic acid;
    one or more polynucleotides coding for enzymes in a pathway that catalyzes a conversion of lactaldehyde to 1,2-propanediol,
    one or more polynucleotides coding for enzymes in a pathway that catalyzes a conversion of 1,2-propanediol to propionaldehyde,
    one or more polynucleotides coding for enzymes in a pathway that catalyzes a conversion of propionaldehyde to 1-propanol,
    one or more polynucleotides coding for enzymes in a pathway that catalyzes a conversion of pyruvate to acetyl-CoA,
    one or more polynucleotides coding for enzymes in a pathway that catalyzes a conversion of acetyl-CoA to acetoacetyl-CoA,
    one or more polynucleotides coding for enzymes in a pathway that catalyzes a conversion of acetoacetyl-CoA to AcAcetate,
    one or more polynucleotides coding for enzymes in a pathway that catalyzes a conversion of AcAcetate to acetone, and/or
    one or more polynucleotides coding for enzymes in a pathway that catalyzes a conversion of acetone to 2-propanol.

In some embodiments, the modified microorganism has a disruption in each of the one or more polynucleotides that code for enzymes that decarboxylate pyruvate (e.g., pyruvate decarboxylase 1, 5, and 6). In some embodiments, the modified microorganism is capable of growth on a C6 carbon source under anaerobic conditions. In some embodiments, the modified microorganism has a disruption in each of the one or more polynucleotides that code for enzymes that decarboxylate pyruvate (e.g., pyruvate decarboxylase 1, 5, and 6) and is capable of growth on a C6 carbon source under anaerobic conditions.

Exemplary enzymes that convert a fermentable carbon source such as glucose to 1-propanol (Pathways B and C)

and/or 2-propanol (Pathway A) including, enzyme substrates, and enzyme reaction products associated with the conversions are presented in Tables 3 to 5 below. The enzyme reference identifier listed in Tables 3 to 5 correlates with the enzyme numbering used in FIGS. 4 and 5, which schematically represents the enzymatic conversion of a fermentable carbon source such as glucose to dihydroxyacetone phosphate or lactate and pyruvate. Dihydroxyacetone phosphate or lactate and pyruvate may be further converted to 1-propanol and/or 2-propanol, using any combination of those enzymes provided in Tables 3 to 5 above including, all of those enzymes as provided in Table 3 to 5 below.

TABLE 3

Pathway A (2-propanol from pyruvate)

| Enzyme No. | Enzyme name | EC Number | Reaction |
|---|---|---|---|
| A1. | Formate-C acetyltransferase | 2.3.1.54 | Pyruvate + CoA → Acetyl-CoA + formate |
|  | Formate-C acetyltransferase activating enzyme | 1.97.1.4 |  |
| A2. | Pyruvate dehydrogenase | 1.2.4.1 2.3.1.12 1.8.1.4 | Pyruvate + CoA + $NAD^+$ → Acetyl-CoA + $CO_2$ + NADH |
| B. | Thiolase | 2.3.1.9 | 2 acetyl-Coa → acetoacetyl-CoA + CoA |
| C. | Acetoacetyl-CoA acetyltransferase (engineered as described herein) | 2.8.3.8 | acetoacetyl-Coa + acetate → acetoacetate + acetyl-CoA |
| D. | Acetatoacetate decarboxylase | 4.1.1.4 | acetoacetate → acetone + CO2 |
| E. | Secondary alcohol dehydrogenase | 1.1.1.2 | acetone + NAD(P)H → 2-propanol + NAD(P)+ |

TABLE 4

Pathway B (1-propanol from Dihydroxyacetone phosphate)

| Enzyme No. | Enzyme name | EC Number | Reaction |
|---|---|---|---|
| F1. | methylglyoxal synthase | 4.2.3.3 | dihydroxyacetone phosphate → methylglyoxal |
| F2. | methylglyoxal synthase, phosphate insensitive | 4.2.3.3 | dihydroxyacetone phosphate → methylglyoxal |
| G. | Methylglyoxal reductase | 1.1.1.— | Methylglyoxal → lactaldehyde |
| H. | Methylglyoxal reductase | 1.1.1.78 | methylglyoxal → hydroxyacetone |
| I. | methylglyoxal reductase [multifunctional] | 1.1.1.— | Hydroxyacetone + NAD(P)H + $H^+$ → 1,2-propanediol + $NAD(P)^+$ |
| J. | methylglyoxal reductase [multifunctional] | 1.1.1.— | Lactaldehyde + NAD(P)H + $H^+$ → 1,2-propanediol + $NAD(P)^+$ |
| K. | 1,2 propanediol dehydratase | 4.2.1.30 | R/S 1,2 propanediol → proprionaldehyde |
| L. | 1-propanol dehydrogenase | 1.1.1.— | proprionaldehyde + NADH → propanol + NAD+ |

TABLE 5

Pathway C (1-propanol from lactate)

| Enzyme No. | Enzyme name | EC Number | Reaction |
|---|---|---|---|
| M1. | D-Lactate dehydrogenase | 1.1.1.28 | Pyruvate + NAD(P)H + $H^+$ → D-Lactate + $NAD(P)^+$ |
| M2. | L-Lactate dehydrogenase | 1.1.1.27 | Pyruvate + NAD(P)H + $H^+$ → L-Lactate + $NAD(P)^+$ |
| N. | Propionate CoA-transferase* | 2.8.3.1 | Lactate + Acetyl-CoA → lactoyl-CoA + acetic acid |
| O. | Lactoyl-CoA synthase | 2.3.3.— | Lactate + CoA + ATP → lactoyl-CoA + AMP |
| P. | 1,2-propanediol oxidoreductase | 1.2.1.— | Lactoyl-CoA + NAD(P)H + $H^+$ → Lactaldehyde + NAD(P) + |
| Q. | Lactaldehyde reductase | 1.1.1.77 | L-Lactaldehyde + NAD(P)H + $H^+$ → L1,2-propanediol + NAD(P) + |

TABLE 5-continued

Pathway C (1-propanol from lactate)

| Enzyme No. | Enzyme name | EC Number | Reaction |
|---|---|---|---|
| J. | methylglyoxal reductase [multifunctional] | 1.1.1.— | Lactaldehyde + NAD(P)H + H$^+$ → 1,2-propanediol + NAD(P)$^+$ |
| K. | 1,2 propanediol dehydratase | 4.2.1.28 | R/S 1,2 propanediol → propionaldehyde |
| L. | 1-propanol dehydrogenase | 1.1.1.— | Propionaldehyde → 1-propanol |

*enzyme with homologous function but altered substrate specificity is required/preferred The microorganism may be an archea, bacteria, or eukaryote. In some embodiments, the bacteria is a *Propionibacterium, Propionispira, Clostridium, Bacillus, Escherichia, Pelobacter*, or *Lactobacillus* including, for example, *Pelobacter propionicus, Clostridium propionicum, Clostridium acetobutylicum, Lactobacillus, Propionibacterium acidipropionici* or *Propionibacterium freudenreichii*. In some embodiments, the eukaryote is a yeast, filamentous fungi, protozoa, or algae. In some embodiments, the yeast is *Saccharomyces cerevisiae, Kluyveromyces lactis* or *Pichia pastoris*.

In some embodiments, the microorganism is additionally modified to comprise one or more tolerance mechanisms including, for example, tolerance to a produced molecule (i.e., methylglyoxal, 1-propanol, 2-propanol, or butadiene), and/or organic solvents. A microorganism modified to comprise such a tolerance mechanism may provide a means to increase titers of fermentations and/or may control contamination in an industrial scale process.

The present disclosure also provides microorganisms (e.g., *S. cerevisiae*) for the co-production of 2-propanol and 1-propanol and/or 1,2-propanediol. Microorganisms may be modified so that they may co-produce 2-propanol and 1-propanol and/or 1,2-propanediol. In an embodiment, a microorganism may have its native ethanol production reduced or eliminated (i.e., shut off). In an embodiment, to eliminate ethanol production in the microorganism the activity of pyruvate decarboxylase (i.e., the enzyme which decarboxylates pyruvate and in the process makes acetaldehyde and CO2) may be disrupted including, for example, knocked-out. Pyruvate decarboxylase comes in three isoforms in yeast and its activity can be mostly knocked out by deleting the genes PDC1, PDC5, and PDC6. Without wishing to be bound by a theory of the invention, the elimination of the pyruvate decarboxylase activity in the cell's cytoplasm renders the yeast cell unable to grow under anaerobic conditions due to two factors: (1) the lack of an alternative route for cytoplasmic acetyl-CoA production, due to the lack of acetaldehyde that would be converted to acetate and acetyl-coA; and (2) a redox imbalance due to excess NADH because the NADH is no longer oxidized in the conversion of acetaldehyde to ethanol. Thus, it is necessary to also alter the ability of the microorganism to import glucose by truncating a transcription factor of the glucose importer called MTH1. This truncation then restores the ability of the APDC1,5,6 mutant microorganism to survive on C6 sugars. In an embodiment, one or more polynucleotides coding for a bacterial pyruvate formate lyase or cytosolic pyruvate dehydrogenase complex may be inserted into the microorganism to convert pyruvate into Acetyl CoA in the cytosol. In an embodiment, the microorganism may be modified to comprise one or more polynucleotides that code for enzymes in a pathway for the coproduction of 2-propanol and 1-propanol and/or 1,2-propanediol. In a further embodiment, the microorganism may be modified to comprise an acetoacetyl CoA hydrolase. Such an acetoacetyl CoA hydrolase may be engineered from an acetoacetylCoA:acetate transferase by making a single Glu-Asp mutation in the acetoacetylCoA: acetate transferase. In an additional embodiment, a microorganism may be modified to comprise one or more polynucleotides coding for a B12-independent dehydratase from the organism *Roseburia inuvolurans* to convert 1,2-propanediol to propanaldehyde. Microorganisms that comprise one or more of the modifications set forth above are termed a non-naturally occurring microorganism or a modified microorganism.

WO2004099425 discloses the overproduction of pyruvate in *S. cerevisiae* by knocking out pyruvate decarboxylase activity and a directed evolution process that allowed this triple mutant to grow on glucose due to a truncation of the MTH1 transcription factor. However, the scope stopped at the overproduction of pyruvate in aerobic fermentation systems. The use of oxygen, in this context, was essential as there is a huge buildup of NADH in the cell due to the fact that NADH is no longer oxidized in the conversion of acetaldehyde to ethanol.

The present disclosure also provides modified microorganisms that comprise: a disruption of one or more enzymes that decarboxylate pyruvate and/or a disruption of one or more transcription factors of one or more enzymes that decarboxylate pyruvate; a genetic modification that substantially decreases glucose import into the microorganism; one or more polynucleotides encoding an acetoacetyl-CoA specific hydrolase as disclosed herein, one or more polynucleotides encoding one or more enzymes in a pathway that produces cytosolic acetyl-CoA; one or more polynucleotides encoding one or more enzymes in a pathway that catalyze a conversion of cytosolic acetyl-CoA to 2-propanol; and one or more polynucleotides encoding one or more enzymes in a pathway that catalyze a conversion of dihydroxyacetone-phosphate to 1-propanol and/or 1,2-propanediol.

The present disclosure further comprises a pyruvate overproducing cell able to produce cytosolic Acetyl-CoA inserting for example, bacterial pyruvate formate lyase or cytosolic pyruvate dehydrogenase complex to convert pyruvate into Acetyl-CoA in the cytosol of the eukaryote cell. The insertion of pyruvate formate lyase in to a PDC-negative yeast strain was disclosed by Waks and Silver in Engineering a Synthetic Dual-Organism System for Hydrogen Production (Applied and Environmental Microbiology, vol. 75, n. 7, 2009, p. 1867-1875) without success in anaerobic growth or metabolism. Furthermore, the present disclosure further comprises a pyruvate overproducing cell able to produce cytosolic Acetyl-CoA and to grow under anaerobic conditions by providing a temporary redox sink that allows reoxidation of NADH by introducing a gene coding for a bacterial soluble NAD(P)+ transhydrogenase (Si-specific) (udhA gene from *E. coli*, E.C. number 1.6.1.1.) that catalyzes the interconversion of NADP++NADH=NADPH+NAD+. The concomitant expression of the PFL and udhA enzymes to restore anaerobic growth to the PDC-null yeast strain expressing the truncated MTH1 constitutes the first report of anaerobic growth of a PDC-null yeast strain and serves as a new eukaryotic chassis for the production of commodity chemicals.

In some embodiments, the disclosure contemplates the modification (e.g., engineering) of one or more of the enzymes provided herein. Such modification may be performed to redesign the substrate specificity of the enzyme and/or to modify (e.g., reduce) its activity against others substrates in order to increase its selectivity for a given substrate. Additionally or alternatively, one or more enzymes as provided herein may be engineered to alter (e.g., enhance including, for example, increase its catalytic activity or its substrate specificity) one or more of its properties, including acceptance of different co-factors such as NADH instead of NADPH.

In some embodiments, sequence alignment and comparative modeling of proteins may be used to alter one or more of the enzymes disclosed herein. Homology modeling or comparative modeling refers to building an atomic-resolution model of the desired protein from its primary amino acid sequence and an experimental three-dimensional structure of a similar protein. This model may allow for the enzyme substrate binding site to be defined, and the identification of specific amino acid positions that may be replaced to other natural amino acid in order to redesign its substrate specificity.

Variants or sequences having substantial identity or homology with the polynucleotides encoding enzymes as disclosed herein may be utilized in the practice of the disclosure. Such sequences can be referred to as variants or modified sequences. That is, a polynucleotide sequence may be modified yet still retain the ability to encode a polypeptide exhibiting the desired activity. Such variants or modified sequences are thus equivalents in the sense that they retain their intended function. Generally, the variant or modified sequence may comprise at least about 40%-60%, preferably about 60%-80%, more preferably about 80%-90%, and even more preferably about 90%-95% sequence identity with the native sequence.

In some embodiments, a microorganism may be modified to express including, for example, overexpress, one or more enzymes as provided herein. The microorganism may be modified by genetic engineering techniques (i.e., recombinant technology), classical microbiological techniques, or a combination of such techniques and can also include naturally occurring genetic variants to produce a genetically modified microorganism. Some of such techniques are generally disclosed, for example, in Sambrook et al., 1989, *Molecular Cloning: A Laboratory Manual*, Cold Spring Harbor Labs Press; and Selifonova et al. (2001) *Appl. Environ. Microbiol.* 67(8):3645.

A genetically modified microorganism may include a microorganism in which a polynucleotide has been inserted, deleted or modified (i.e., mutated; e.g., by insertion, deletion, substitution, and/or inversion of nucleotides), in such a manner that such modifications provide the desired effect of expression (e.g., over-expression) of one or more enzymes as provided herein within the microorganism. Genetic modifications which result in an increase in gene expression or function can be referred to as amplification, overproduction, overexpression, activation, enhancement, addition, or up-regulation of a gene. Addition of cloned genes to increase gene expression can include maintaining the cloned gene(s) on replicating plasmids or integrating the cloned gene(s) into the genome of the production organism. Furthermore, increasing the expression of desired cloned genes can include operatively linking the cloned gene(s) to native or heterologous transcriptional control elements.

Where desired, the expression of one or more of the enzymes provided herein are under the control of a regulatory sequence that controls directly or indirectly the expression of the enzyme in a time-dependent fashion during a fermentation reaction.

In some embodiments, a microorganism is transformed or transfected with a genetic vehicle such as, an expression vector comprising an exogenous polynucleotide sequence coding for the enzymes provided herein.

Polynucleotide constructs prepared for introduction into a prokaryotic or eukaryotic host may typically, but not always, comprise a replication system (i.e. vector) recognized by the host, including the intended polynucleotide fragment encoding the desired polypeptide, and may preferably, but not necessarily, also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, mRNA stabilizing sequences, nucleotide sequences homologous to host chromosomal DNA, and/or a multiple cloning site. Signal peptides may also be included where appropriate, preferably from secreted polypeptides of the same or related species, which allow the protein to cross and/or lodge in cell membranes or be secreted from the cell.

The vectors can be constructed using standard methods (see, e.g., Sambrook et al., *Molecular Biology: A Laboratory Manual*, Cold Spring Harbor, N.Y. 1989; and Ausubel, et al., Current Protocols in Molecular Biology, Greene Publishing, Co. N.Y., 1995).

The manipulation of polynucleotides of the present disclosure including polynucleotides coding for one or more of the enzymes disclosed herein is typically carried out in recombinant vectors. Numerous vectors are publicly available, including bacterial plasmids, bacteriophage, artificial chromosomes, episomal vectors and gene expression vectors, which can all be employed. A vector of use according to the disclosure may be selected to accommodate a protein coding sequence of a desired size. A suitable host cell is transformed with the vector after in vitro cloning manipulations. Host cells may be prokaryotic, such as any of a number of bacterial strains, or may be eukaryotic, such as yeast or other fungal cells, insect or amphibian cells, or mammalian cells including, for example, rodent, simian or human cells. Each vector contains various functional components, which generally include a cloning site, an origin of replication and at least one selectable marker gene. If given vector is an expression vector, it additionally possesses one or more of the following—enhancer element, promoter, transcription termination and signal sequences, each positioned in the vicinity of the cloning site, such that they are operatively linked to the gene encoding a polypeptide repertoire member according to the disclosure.

Vectors, including cloning and expression vectors, may contain nucleic acid sequences that enable the vector to replicate in one or more selected host cells. For example, the sequence may be one that enables the vector to replicate independently of the host chromosomal DNA and may include origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

A cloning or expression vector may contain a selection gene also referred to as a selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors may be performed in *E. coli* (e.g., strain TB1 or TG1, DH5α, DH10β, JM110). An *E. coli*-selectable marker, for example, the β-lactamase gene that confers resistance to the antibiotic ampicillin, may be of use. These selectable markers can be obtained from *E. coli* plasmids, such as pBR322 or a pUC plasmid such as pUC18 or pUC19, or pUC119.

Expression vectors may contain a promoter that is recognized by the host organism. The promoter may be operably linked to a coding sequence of interest. Such a promoter may be inducible or constitutive. Polynucleotides are operably linked when the polynucleotides are in a relationship permitting them to function in their intended manner.

Promoters suitable for use with prokaryotic hosts may include, for example, the α-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Moreover, host constitutive or inducible promoters may be used. Promoters for use in bacterial systems will also generally contain a Shine-Dalgarno sequence operably linked to the coding sequence.

Viral promoters obtained from the genomes of viruses include promoters from polyoma virus, fowlpox virus, adenovirus (e.g., Adenovirus 2 or 5), herpes simplex virus (thymidine kinase promoter), bovine papilloma virus, avian sarcoma virus, cytomegalovirus, a retrovirus (e.g., MoMLV, or RSV LTR), Hepatiti B virus, Myeloproliferative sarcoma virus promoter (MPSV), VISNA, and Simian Virus 40 (SV40). Heterologous mammalian promoters include, e.g., the actin promoter, immunoglobulin promoter, heat-shock protein promoters.

The early and late promoters of the SV40 virus are conveniently obtained as a restriction fragment that also contains the SV40 viral origin of replication (see, e.g., Fiers et al., *Nature*, 273:113 (1978); Mulligan and Berg, *Science*, 209:1422-1427 (1980); and Pavlakis et al., *Proc. Natl. Acad. Sci. USA*, 78:7398-7402 (1981)). The immediate early promoter of the human cytomegalovirus (CMV) is conveniently obtained as a Hind III E restriction fragment (see, e.g., Greenaway et al., *Gene*, 18:355-360 (1982)). A broad host range promoter, such as the SV40 early promoter or the Rous sarcoma virus LTR, is suitable for use in the present expression vectors.

Generally, a strong promoter may be employed to provide for high level transcription and expression of the desired product. Among the eukaryotic promoters that have been identified as strong promoters for high-level expression are the SV40 early promoter, adenovirus major late promoter, mouse metallothionein-I promoter, Rous sarcoma virus long terminal repeat, and human cytomegalovirus immediate early promoter (CMV or CMV IE). In an embodiment, the promoter is a SV40 or a CMV early promoter.

The promoters employed may be constitutive or regulatable, e.g., inducible. Exemplary inducible promoters include jun, fos and metallothionein and heat shock promoters. One or both promoters of the transcription units can be an inducible promoter. In an embodiment, the GFP is expressed from a constitutive promoter while an inducible promoter drives transcription of the gene coding for one or more enzymes as disclosed herein and/or the amplifiable selectable marker.

The transcriptional regulatory region in higher eukaryotes may comprise an enhancer sequence. Many enhancer sequences from mammalian genes are known e.g., from globin, elastase, albumin, α-fetoprotein and insulin genes. A suitable enhancer is an enhancer from a eukaryotic cell virus. Examples include the SV40 enhancer on the late side of the replication origin (bp 100-270), the enhancer of the cytomegalovirus immediate early promoter (Boshart et al. *Cell* 41:521 (1985)), the polyoma enhancer on the late side of the replication origin, and adenovirus enhancers (see also, e.g., Yaniv, *Nature*, 297:17-18 (1982) on enhancing elements for activation of eukaryotic promoters). The enhancer sequences may be introduced into the vector at a position 5' or 3' to the gene of interest, but is preferably located at a site 5' to the promoter.

Yeast and mammalian expression vectors may contain prokaryotic sequences that facilitate the propagation of the vector in bacteria. Therefore, the vector may have other components such as an origin of replication (e.g., a nucleic acid sequence that enables the vector to replicate in one or more selected host cells), antibiotic resistance genes for selection in bacteria, and/or an amber stop codon which can permit translation to read through the codon. Additional eukaryotic selectable gene(s) may be incorporated. Generally, in cloning vectors the origin of replication is one that enables the vector to replicate independently of the host chromosomal DNA, and includes origins of replication or autonomously replicating sequences. Such sequences are well known, e.g., the ColE1 origin of replication in bacteria. Various viral origins (e.g., SV40, polyoma, adenovirus, VSV or BPV) are useful for cloning vectors in mammalian cells. Generally, a eukaryotic replicon is not needed for expression in mammalian cells unless extrachromosomal (episomal) replication is intended (e.g., the SV40 origin may typically be used only because it contains the early promoter).

To facilitate insertion and expression of different genes coding for the enzymes as disclosed herein from the constructs and expression vectors, the constructs may be designed with at least one cloning site for insertion of any gene coding for any enzyme disclosed herein. The cloning site may be a multiple cloning site, e.g., containing multiple restriction sites.

The plasmids may be propagated in bacterial host cells to prepare DNA stocks for subcloning steps or for introduction into eukaryotic host cells. Transfection of eukaryotic host cells can be any performed by any method well known in the art. Transfection methods include lipofection, electroporation, calcium phosphate co-precipitation, rubidium chloride or polycation mediated transfection, protoplast fusion and microinjection. Preferably, the transfection is a stable transfection. The transfection method that provides optimal transfection frequency and expression of the construct in the particular host cell line and type, is favored. Suitable methods can be determined by routine procedures. For stable transfectants, the constructs are integrated so as to be stably maintained within the host chromosome.

Vectors may be introduced to selected host cells by any of a number of suitable methods known to those skilled in the art. For example, vector constructs may be introduced to appropriate cells by any of a number of transformation methods for plasmid vectors. For example, standard calcium-chloride-mediated bacterial transformation is still commonly used to introduce naked DNA to bacteria (see, e.g., Sambrook et al., 1989, *Molecular Cloning, A Laboratory Manual*, Cold Spring Harbor Laboratory Press, Cold Spring Harbor, N.Y.), but electroporation and conjugation may also be used (see, e.g., Ausubel et al., 1988, *Current Protocols in Molecular Biology*, John Wiley & Sons, Inc., NY, N.Y.).

For the introduction of vector constructs to yeast or other fungal cells, chemical transformation methods may be used (e.g., Rose et al., 1990, *Methods in Yeast Genetics*, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to mammalian cells, the method used may depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, *Current Protocols in Molecular Biology*, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, lipofection reagents such as LIPOFECTAMINE™ (Life Technologies) or LIPOTAXI™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation Immortalized host cell cultures amenable to transfection and in vitro cell culture and of the kind typically employed in genetic engineering are preferred. Examples of useful mammalian host cell lines are monkey kidney CV1 line transformed by SV40 (CO 7, ATCC CRL 1651); human embryonic kidney line (293 or 293 derivatives adapted for growth in suspension culture, Graham et al., J. Gen Virol., 36:59 (1977); baby hamster kidney cells (BHK, ATCC CCL 10); DHFR-Chinese hamster ovary cells (ATCC CRL-9096); dp12.CHO cells, a derivative of CHO/DHFR-(EP 307,247 published 15 Mar. 1989); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); PEER human acute lymphoblastic cell line (Ravid et al. Int. J. Cancer 25:705-710 (1980)); MRC 5 cells; FS4 cells; human hepatoma line (Hep G2), human HT1080 cells, KB cells, JW-2 cells, Detroit 6 cells, NIH-3T3 cells, hybridoma and myeloma cells. Embryonic cells used for generating transgenic animals are also suitable (e.g., zygotes and embryonic stem cells).

Suitable host cells for cloning or expressing polynucleotides (e.g., DNA) in vectors may include, for example, prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), *E. coli* JM110 (ATCC 47,013) and *E. coli* W3110 (ATCC 27,325) are suitable.

In addition to prokaryotes, eukaryotic microbes such as filamentous fungi or yeast may be suitable cloning or expression hosts for vectors comprising polynucleotides coding for one or more enzymes. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia* pastors (EP 183,070); *Candida*; *Trichoderma* reesia (EP 244,234); *Neurospora crassa*; *Schwanniomyces* such as *Schwanniomyces occidentalis*; and filamentous fungi such as, e.g., *Neurospora*, *Peniciffium*, *Tolypocladium*, and *Aspergillus* hosts such as *A. nidulans* and *A. niger*.

When the enzyme is glycosylated, suitable host cells for expression may be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* (silk moth) have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, *petunia*, tomato, tobacco, lemna, and other plant cells can also be utilized as host cells.

Examples of useful mammalian host cells are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (CO 7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for production of one or more enzymes as disclosed herein or with polynucleotides coding for one or more enzymes as disclosed herein and cultured in conventional nutrient media modified as appropriate for inducing promoters, selecting transformants, or amplifying the genes encoding the desired sequences.

Host cells containing desired nucleic acid sequences coding for the disclosed enzymes may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44, (1979); Barnes et al., Anal. Biochem. 102: 255 (1980); U.S. Pat. Nos. 4,767,704; 4,657, 866; 4,927,762; 4,560,655; or 5,122,469; W090103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adeNOSine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Any of the intermediates produced in any of the enzymatic pathways disclosed herein may be an intermediate in the classical sense of the word in that they may be enzymatically converted to another intermediate or an end product. Alternatively, the intermediates themselves may be considered an end product.

TABLE 4

Exemplary Gene Identified (GI) numbers

| Pathways | FIGS. | Enzyme No. | EC No. | Enzyme candidate | Gene | Uniprot ID (aa) | SEQ ID NO. |
|---|---|---|---|---|---|---|---|
| A | 4, 5 | A | 2.3.1.54/1.97.1.4 | Formate-C acetyltransferase | PFLB | P75793 | 7 |
| A | 4, 5 | A | 2.3.1.54/1.97.1.4 | Formate-C acetyltransferase (activating enzyme) | PFLA | C4ZXZ6 | 8 |
| A | 4, 5 | A | 2.3.1.54/1.97.1.4 | Formate-C acetyltransferase | PFLB | K9LI23 | 9 |
| A | 4, 5 | A | 2.3.1.54/1.97.1.4 | Formate-C acetyltransferase (activating enzyme) | PFLA | Q6RFH6 | 10 |
| A | 4, 5 | A | 1.2.4.1/2.3.1.12/ 1.8.1.4 | Pyruvate dehydrogenase complex | pda1 | P16387 | 11 |
| A | 4, 5 | A | 1.2.4.1/2.3.1.12/ 1.8.1.4 | Pyruvate dehydrogenase complex | pdb1 | P32473 | 12 |
| A | 4, 5 | A | 1.2.4.1/2.3.1.12/ 1.8.1.4 | Pyruvate dehydrogenase complex | lat1 | P12695 | 13 |
| A | 4, 5 | A | 1.2.4.1/2.3.1.12/ 1.8.1.4 | Pyruvate dehydrogenase complex | lpd1 | P09624 | 14 |
| A | 4, 5 | A | 1.2.4.1/2.3.1.12/ 1.8.1.4 | Pyruvate dehydrogenase complex | pdx1 | P16451 | 15 |
| A | 4, 5 | A | 1.2.4.1/2.3.1.12/ 1.8.1.4 | Pyruvate dehydrogenase complex (El aplha) | pdhA | F2MRX7 | 16 |

TABLE 4-continued

Exemplary Gene Identified (GI) numbers

| Pathways | FIGS. | Enzyme No. | EC No. | Enzyme candidate | Gene | Uniprot ID (aa) | SEQ ID NO. |
|---|---|---|---|---|---|---|---|
| A | 4, 5 | B | 3.1.2.— | Acetoacetyl-CoA hydrolase | — | — | SEQ ID NO: 2, 4, or 6 |
| A | 4, 5 | D | 4.1.1.4 | acetoacetate decarboxylase | adc | P23670 | 17 |
| A | 4, 5 | D | 4.1.1.4 | acetoacetate decarboxylase | adc | A6M020 | 18 |
| A | 4, 5 | E | 1.1.1.2 | secondary alcohol dehydrogenase | adh | P25984 | 19 |
| B | 4 | F | 4.2.3.3 | methylglyoxal synthase | mgsA | P42980 | 20 |
| B | 4 | F | 4.2.3.3 | methylglyoxal synthase | mgsA | P0A731 | 21 |
| B | 4 | F | 4.2.3.3 | methylglyoxal synthase | mgsA* | P0A731 | 22 |
| B | 4 | G | 1.1.1.— | methylglyoxal reductase, multifunctional | ydjg | P77256 | 23 |
| B | 4 | H | 1.1.1.78 | methylglyoxal reductase | ypr1 | C7GMG9 | 24 |
| B | 4 | I | 1.1.1.304 | methylglyoxal reductase, multifunctional | budC | Q48436 | 25 |
| B, C | 4, 5 | J | 1.1.1.77 | lactaldehyde reductase | fucO | P0A9S1 | 26 |
| B, C | 4, 5 | J | 1.1.1.— | methylglyoxal reductase [multifunctional] | yafB | P30863 | 27 |
| B, C | 4, 5 | K | 4.2.1.30 | glycerol dehydratase | dhaB1 | Q8GEZ8 | 28 |
| B, C | 4, 5 | K | 4.2.1.30 | glycerol dehydratase activator | dhaB2 | Q8GEZ7 | 29 |
| B, C | 4, 5 | K | 4.2.1.30 | diol dehydratase | b1 | Q1A666 | 30 |
| B, C | 4, 5 | K | 4.2.1.30 | diol dehydratase activator | b2 | Q1A665 | 31 |
| B, C | 4, 5 | L | 1.1.1.1 | alcohol dehydrogenase | adh | C6PZV5 | 32 |
| C | 5 | M | 1.1.1.28 | D-Lactate dehydrogenase | ldhA | P52643 | 33 |
| C | 5 | M | 1.1.1.27 | L-Lactate dehydrogenase | ldhL2 | P59390 | 34 |
| C | 5 | M | 1.1.1.27 | L-lactate dehydrogenase | ldh2 | P19858 | 35 |
| C | 5 | N | 2.8.3.1 | propionate CoA-transferase* | pct | Q9L3F7 | 36 |
| C | 5 | O | 2.3.3.— | Lactoyl-CoA Synthase | ACS1 | Q01574 | 37 |
| C | 5 | P | 1.2.1.— | CoA-dependent propionaldehyde dehydrogenase* | pduP | Q9XDN1 | 38 |
| C | 5 | Q | 1.1.1.77 | L-1,2-propanediol oxidoreductase | fucO | P0A9S1 | 39 |

Polynucleotides and Encoded Enzymes

Figure 4:
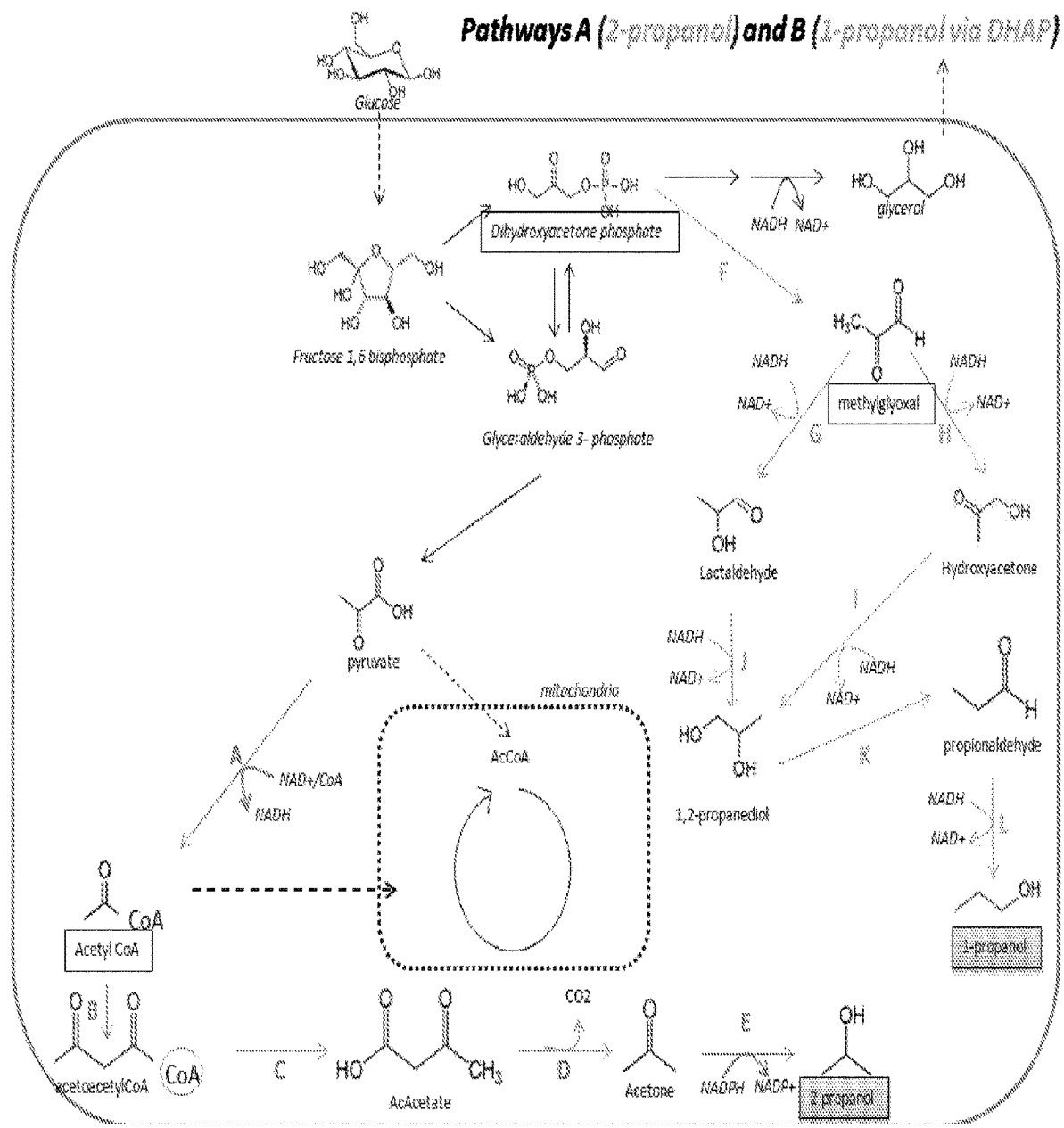
FIG. 4 depicts an exemplary pathway for the co-production of 1-propanol and 2-propanol, where 1-propanol is produced via a dihydroxyacetone-phosphate intermediate.
Figure 5:
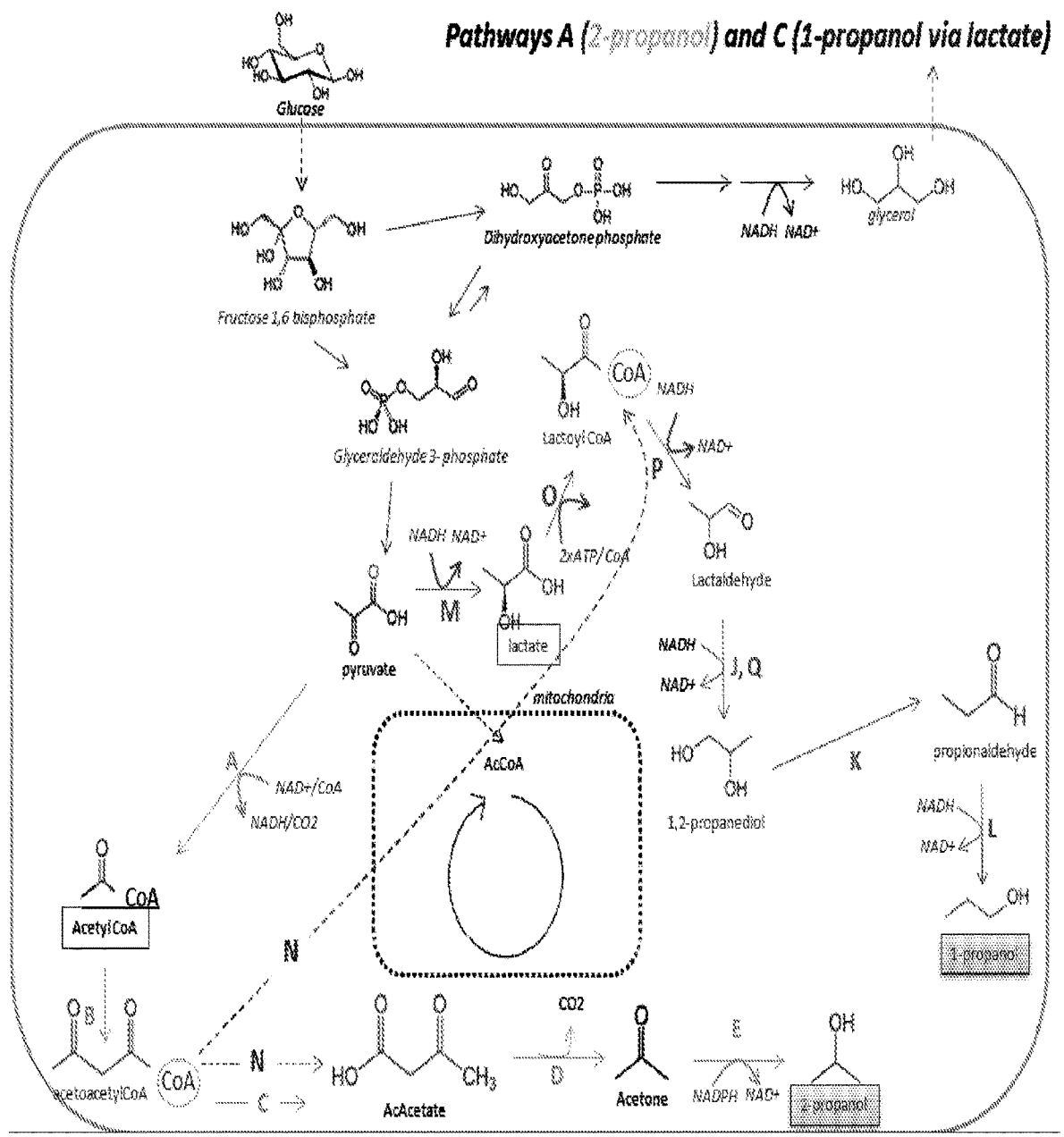
FIG. 5 depicts an exemplary pathway for the co-production of 1-propanol and 2-propanol, where 1-propanol is produced via a glyceraldehyde 3-phosphate.

Any known polynucleotide (e.g., gene) that codes for an enzyme or variant thereof that is capable of catalyzing an enzymatic conversion including, for example, an enzyme as set forth in any one of Tables 3-5 or FIGS. 4-5, is contemplated for use by the present disclosure. Such polynucleotides may be modified (e.g., genetically engineered) to modulate (e.g., increase or decrease) the substrate specificity of an encoded enzyme, or the polynucleotides may be modified to change the substrate specificity of the encoded enzyme (e.g., a polynucleotide that codes for an enzyme with specificity for a substrate may be modified such that the enzyme has specificity for an alternative substrate). Preferred microorganisms may comprise polynucleotides coding for one or more of the enzymes as set forth in Tables 3-5 and FIGS. 4-5.

Enzymes for catalyzing the conversions set forth in pathways A, B, and C of Tables 3-5 and FIGS. 4-5 are categorized in Table 4 below.

Methods for the Co-Production of 1-Propanol and 2-Propanol 1-propanol and 2-propanol may be produced by contacting any of the genetically modified microorganisms provided herein with a fermentable carbon source. Such methods may preferably comprise contacting a fermentable carbon source with a microorganism comprising one or more polynucleotides coding for enzymes in a pathway that catalyzes a conversion of the fermentable carbon source to any of the intermediates provided in FIGS. 4-5 (Tables 3-5) and one or more polynucleotides coding for enzymes in a pathway that catalyze a conversion of the one or more intermediates provided in FIGS. 4-5 (tables 3-5) to 1-propanol and 2-propanol in a fermentation media; and expressing the one or more polynucleotides coding for the enzymes in the pathway that catalyzes a conversion of the fermentable carbon source to the one or more intermediates provided in FIGS. 4-5 (tables 3-5) and one or more polynucleotides coding for enzymes in a pathway that catalyze a conversion of the one or more intermediates provided in FIGS. 4-5 (tables 3-5) to 1-propanol and 2-propanol.

The metabolic pathways that lead to the production of industrially important compounds involve oxidation-reduction (redox) reactions. For example, during fermentation, glucose is oxidized in a series of enzymatic reactions into smaller molecules with the concomitant release of energy. The electrons released are transferred from one reaction to another through universal electron carriers, such Nicotinamide Adenine Dinucleotide (NAD) and Nicotinamide Adenine Dinucleotide Phosphate (NAD(P)), which act as cofactors for oxidoreductase enzymes. In microbial catabolism, glucose is oxidized by enzymes using the oxidized form of the cofactors (NAD(P)+ and/or NAD+) as cofactor thus generating reducing equivalents in the form of the reduced cofactor (NAD(P)H and NADH). In order for fermentation to continue, redox-balanced metabolism is required, i.e., the cofactors must be regenerated by the reduction of microbial cell metabolic compounds.

Microorganism-catalyzed fermentation for the production of natural products is a widely known application of biocatalysis. Industrial microorganisms can affect multistep conversions of renewable feedstocks to high value chemical products in a single reactor. Products of microorganism-catalyzed fermentation processes range from chemicals such as ethanol, lactic acid, amino acids and vitamins, to high value small molecule pharmaceuticals, protein pharmaceuticals, and industrial enzymes. In many of these processes, the biocatalysts are whole-cell microorganisms, including microorganisms that have been genetically modified to express heterologous genes.

Some key parameters for efficient microorganism-catalyzed fermentation processes include the ability to grow microorganisms to a greater cell density, increased yield of desired products, increased amount of volumetric productivity, removal of unwanted co-metabolites, improved utilization of inexpensive carbon and nitrogen sources, adaptation to varying fermenter conditions, increased production of a primary metabolite, increased production of a secondary metabolite, increased tolerance to acidic conditions, increased tolerance to basic conditions, increased tolerance to organic solvents, increased tolerance to high salt conditions and increased tolerance to high or low temperatures. Inefficiencies in any of these parameters can result in high manufacturing costs, inability to capture or maintain market share, and/or failure to bring fermented end-products to market.

The methods and compositions of the present disclosure can be adapted to conventional fermentation bioreactors (e.g., batch, fed-batch, cell recycle, and continuous fermentation).

In some embodiments, a microorganism (e.g., a genetically modified microorganism) as provided herein is cultivated in liquid fermentation media (i.e., a submerged culture) which leads to excretion of the fermented product(s) into the fermentation media. In one embodiment, the fermented end product(s) can be isolated from the fermentation media using any suitable method known in the art.

In some embodiments, formation of the fermented product occurs during an initial, fast growth period of the microorganism. In one embodiment, formation of the fermented product occurs during a second period in which the culture is maintained in a slow-growing or non-growing state. In one embodiment, formation of the fermented product occurs during more than one growth period of the microorganism. In such embodiments, the amount of fermented product formed per unit of time is generally a function of the metabolic activity of the microorganism, the physiological culture conditions (e.g., pH, temperature, medium composition), and the amount of microorganisms present in the fermentation process.

In some embodiments, the fermentation product is recovered from the periplasm or culture medium as a secreted metabolite. In one embodiment, the fermentation product is extracted from the microorganism, for example when the microorganism lacks a secretory signal corresponding to the fermentation product. In one embodiment, the microorganisms are ruptured and the culture medium or lysate is centrifuged to remove particulate cell debris. The membrane and soluble protein fractions may then be separated if necessary. The fermentation product of interest may then be purified from the remaining supernatant solution or suspension by, for example, distillation, fractionation, chromatography, precipitation, filtration, and the like.

The methods of the present disclosure are preferably preformed under anaerobic conditions. Both the degree of reduction of a product as well as the ATP requirement of its synthesis determines whether a production process is able to proceed aerobically or anaerobically. To produce 1-propanol and 2-propanol or 1-propanol and butadiene via anaerobic microbial conversion, or at least by using a process with reduced oxygen consumption, redox imbalances should be avoided. Several types of metabolic conversion steps involve redox reactions. Such redox reactions involve electron transfer mediated by the participation of redox cofactors such as NADH, NADPH and ferredoxin. Since the amounts of redox cofactors in the cell are limited to permit the continuation of metabolic processes, the cofactors have to be regenerated. In order to avoid such redox imbalances, alternative ways of cofactor regeneration may be engineered, and in some cases additional sources of ATP generation may be provided. Alternatively, oxidation and reduction processes may be separated spatially in bioelectrochemical systems (Rabaey and Rozendal, 2010, *Nature reviews, Microbiology*, vol. 8: 706-716).

In some embodiment, redox imbalances may be avoided by using substrates (e.g., fermentable carbon sources) that are more oxidized or more reduced. for example, if the utilization of a substrate results in a deficit or surplus of electrons, a requirement for oxygen can be circumvented by using substrates that are more reduced or oxidized, respectively. For example, glycerol which is a major byproduct of biodiesel production is more reduced than sugars, and is therefore more suitable for the synthesis of compounds whose production from sugar results in cofactor oxidation, such as succinic acid. In some embodiments, if the conversion of a substrate to a product results in an electron deficit, co-substrates can be added that function as electron donors (Babel 2009, *Eng. Life Sci.* 9, 285-290). An important criterion for the anaerobic use of co-substrates is that their redox potential is higher than that of NADH (Geertman et al., 2006, *FEMS Yeast Res.* 6, 1193-1203). If the conversion of substrate to produce results in an electron surplus, co-substrates can be added that function as electron acceptors.

Methods for the Production of Polypropylene 1-propanol produced via methods disclosed herein may be dehydrated to form propylene, which may then be polymerized to produce polypropylene in a cost-effective manner.

Propylene is a chemical compound that is widely used to synthesize a wide range of petrochemical products. For instance, this olefin is the raw material used for the production of polypropylene, its copolymers and other chemicals such as acrylonitrile, acrylic acid, epichloridrine and acetone. Propylene demand is growing faster than ethylene demand, mainly due to the growth of market demand for polypropylene. Propylene is polymerized to produce thermoplastics resins for innumerable applications such as rigid or flexible packaging materials, blow molding and injection molding.

Propylene is typically obtained in large quantity scales as a byproduct of catalytical or thermal oil cracking, or as a co-product of ethylene production from natural gas. (Propylene, Jamie G. Lacson, CEH Marketing Research Report-2004, Chemical Economics Handbook-SRI International). The use of alternative routes for the production of propylene has been continuously evaluated using a wide range of renewable raw materials ("Green Propylene", Nexant, January 2009). These routes include, for example, dimerization of ethylene to yield butylene, followed by metathesis with additional ethylene to produce propylene. Another route is biobutanol production by sugar fermentation followed by dehydration and methatesis with ethylene. Some thermal routes are also being evaluated such as gasification of biomass to produce a syngas followed by synthesis of methanol, which may then produce green propylene via methanol-to-olefin technology.

Propylene production by iso-propanol dehydration has been well-described in document EP00498573B1, wherein all examples show propylene selectivity higher than 90% with high conversions. Dehydration of 1-propanol has also been studied in the following articles: "Mechanism and Kinetics of the Acid-Catalyzed Dehydration of 1- and iso-propanol in Hot Compressed Liquid Water" (Antal, M et al., *Ind. Eng. Chem. Res.* 1998, 37, 3820-3829) and "Fischer-Tropsch Aqueous Phase Refining by Catalytic Alcohol Dehydration" (Nel, R. et al., *Ind. Eng. Chem. Res.* 2007, 46, 3558-3565). The reported yield is higher than 90%.

EXAMPLES

Example 1: Engineering of Acetoacetyl-CoA Hydrolase

An enzyme having acetoacetyl-CoA transferase activity may be engineered by any method known in the art to produce an acetoacetyl-CoA specific hydrolase.

In an exemplary method, an amino acid sequence of an enzyme having acetoacetyl-CoA transferase activity is obtained. Next, the glutamic acid residue at a position corresponding to amino acid position 51 of SEQ ID NO: 1 in the enzyme is identified by aligning the amino acid sequence of the enzyme with SEQ ID NO: 1. A site in the enzyme corresponding to amino acid position 51 of SEQ ID NO: 1 is then selected for substitution. Such substitution of the identified glutamic acid residue may include substitution of the glutamic acid residue for aspartic acid and may be made by any method known in the art including, for example, site directed mutagenesis. Subsequently, an acetoacetyl-CoA specific hydrolase is obtained having a specific acetoacetyl-CoA hydrolase activity at least 10× higher than its acetyl-CoA hydrolase activity.

Example 2: Modification of Microorganism for Production of 1-Propanol and 2-Propanol A microorganism such as a bacterium is genetically modified to produce 1-propanol and 2-propanol from a fermentable carbon source including, for example, glucose.

In an exemplary method, a microorganism may be genetically engineered by any methods known in the art to comprise: i.) one or more polynucleotides coding for enzymes in a pathway that catalyze a conversion of the fermentable carbon source to dihydroxyacetone-phosphate or glyceraldehyde 3-phosphate and one or more polynucleotides coding for enzymes in a pathway that catalyze a conversion of dihydroxyacetone-phosphate or glyceraldehyde 3-phosphate to 1-propanol and 2-propanol.

Alternatively, a microorganism that lacks one or more enzymes (e.g., one or more functional enzymes that are catalytically active) for the conversion of a fermentable carbon source to 1-propanol and 2-propanol may be genetically modified to comprise one or more polynucleotides coding for enzymes (e.g., functional enzymes including, for example any enzyme disclosed herein) in a pathway that the microorganism lacks to catalyze a conversion of the fermentable carbon source to 1-propanol and 2-propanol.

Example 3: Fermentation of Glucose by Genetically Modified Microorganism to Produce 1-Propanol and 2-Propanol A genetically modified microorganism, as produced in Example 1 above, may be used to ferment a carbon source to produce 1-propanol and 2-propanol.

In an exemplary method, a previously-sterilized culture medium comprising a fermentable carbon source (e.g., 9 g/L glucose, 1 g/L KH2PO4, 2 g/L (NH4)2HPO4, 5 mg/L FeSO4O7H2O, 10 mg/L MgSO4O7H2O, 2.5 mg/L MnSO4.H2O, 10 mg/L CaCl2.6H2O, 10 mg/L CoCl2O6H2O, and 10 g/L yeast extract) is charged in a bioreactor.

During fermentation, anaerobic conditions are maintained by, for example, sparging nitrogen through the culture medium. A suitable temperature for fermentation (e.g., about 30° C.) is maintained using any method known in the art. A near physiological pH (e.g., about 6.5) is maintained by, for example, automatic addition of sodium hydroxide. The bioreactor is agitated at, for example, about 50 rpm. Fermentation is allowed to run to completion.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. An engineered enzyme having acetoacetyl-CoA substrate specificity and acetoacetyl-CoA specific hydrolase activity, wherein the engineered enzyme has the amino acid sequence as set forth in SEQ ID NO: 2, SEQ ID NO: 4, or SEQ ID NO: 6.

2. The engineered enzyme of claim 1, wherein the engineered enzyme comprises i) an amino acid sequence of an enzyme having acetoacetyl-CoA transferase activity and ii) a substitution of a glutamic acid residue to an aspartic acid residue at a position corresponding to amino acid position 51 of SEQ ID NO: 1.

3. The engineered enzyme of claim 2, wherein the enzyme having acetoacetyl-CoA transferase activity belongs to an enzyme family having 3-oxoacid CoA-transferase activity.

4. The engineered enzyme of claim 2, wherein the enzyme having acetoacetyl-CoA transferase activity is butyrate-acetoacetate CoA-transferase or acetate-acetoacetate-CoA transferase.

5. The engineered enzyme of claim 2, wherein the enzyme having acetoacetyl-CoA transferase activity is from *Clostridium acetobutylicum* or *Escherichia coli*.

6. The engineered enzyme of claim 1, wherein the engineered enzyme has a specific acetoacetyl-CoA hydrolase activity at least 10× higher than its acetylCoA hydrolase activity.

7. A method of producing the engineered enzyme of claim 1, the method comprising:
   a) selecting an enzyme having acetoacetyl-CoA transferase activity, wherein the amino acid sequence of the selected enzyme comprises SEQ ID NO: 1, SEQ ID NO: 3, or SEQ ID NO: 5, and
   b) substituting a glutamic acid residue to an aspartic acid residue at a position corresponding to amino acid position 51 of SEQ ID NO: 1, amino acid position 46 of SEQ ID NO: 3, or amino acid position 333 of SEQ ID NO: 5 in the amino acid sequence of the selected enzyme to produce the engineered enzyme of claim 1.

8. The method of claim 7, wherein the substitution is introduced via site directed mutagenesis.

9. The method of claim 7, wherein the enzyme having acetoacetyl-CoA transferase activity belongs to an enzyme family having 3-oxoacid CoA-transferase activity.

10. The method of claim 7, wherein the enzyme having acetoacetyl-CoA transferase activity is butyrate-acetoacetate CoA-transferase or acetate-acetoacetate-CoA transferase.

11. The method of claim 7, wherein the enzyme having acetoacetyl-CoA transferase activity is from *Clostridium acetobutylicum* or *Escherichia coli*.

12. The method of claim 7, wherein the engineered enzyme has a specific acetoacetyl-CoA hydrolase activity at least 10× higher than its acetylCoA hydrolase activity.

\* \* \* \* \*

SEQUENCE LISTING

```
<160> NUMBER OF SEQ ID NOS: 58

<210> SEQ ID NO 1
<211> LENGTH: 221
<212> TYPE: PRT
<213> ORGANISM: Artificial sequence
<220> FEATURE:
<223> OTHER INFORMATION: Synthesized: Butyrate--acetoacetate CoA-
      transferase subunit B [Clostridium acetobutylicum]

<400> SEQUENCE: 1

Met Ile Asn Asp Lys Asn Leu Ala Lys Glu Ile Ile Ala Lys Arg Val
1               5                   10                  15

Ala Arg Glu Leu Lys Asn Gly Gln Leu Val Asn Leu Gly Val Gly Leu
            20                  25                  30

Pro Thr Met Val Ala Asp Tyr Ile Pro Lys Asn Phe Lys Ile Thr Phe
        35                  40                  45

Gln Ser Glu Asn Gly Ile Val Gly Met Gly Ala Ser Pro Lys Ile Asn
    50                  55                  60
```

Glu Ala Asp Lys Asp Val Val Asn Ala Gly Gly Asp Tyr Thr Thr Val
65                  70                  75                  80

Leu Pro Asp Gly Thr Phe Phe Asp Ser Ser Val Ser Phe Ser Leu Ile
                85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
    130                 135                 140

Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
                165                 170                 175

Glu Leu Gly Val Ile Glu Val Ile Asn Asp Gly Leu Leu Leu Thr Glu
            180                 185                 190

Ile Asn Lys Asn Thr Thr Ile Asp Glu Ile Arg Ser Leu Thr Ala Ala
        195                 200                 205

Asp Leu Leu Ile Ser Asn Glu Leu Arg Pro Met Ala Val
    210                 215                 220

<210> SEQ ID NO 2
<211> LENGTH: 221
<212> TYPE: PRT
<213> ORGANISM: Artificial sequence
<220> FEATURE:
<223> OTHER INFORMATION: Synthesized: Modified butyrate--acetoacetate
      CoA-transferase subunit B [Clostridium acetobutylicum]

<400> SEQUENCE: 2

Met Ile Asn Asp Lys Asn Leu Ala Lys Glu Ile Ile Ala Lys Arg Val
1               5                   10                  15

Ala Arg Glu Leu Lys Asn Gly Gln Leu Val Asn Leu Gly Val Gly Leu
            20                  25                  30

Pro Thr Met Val Ala Asp Tyr Ile Pro Lys Asn Phe Lys Ile Thr Phe
        35                  40                  45

Gln Ser Asp Asn Gly Ile Val Gly Met Gly Ala Ser Pro Lys Ile Asn
    50                  55                  60

Glu Ala Asp Lys Asp Val Val Asn Ala Gly Gly Asp Tyr Thr Thr Val
65                  70                  75                  80

Leu Pro Asp Gly Thr Phe Phe Asp Ser Ser Val Ser Phe Ser Leu Ile
                85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
    130                 135                 140

Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
                165                 170                 175

Glu Leu Gly Val Ile Glu Val Ile Asn Asp Gly Leu Leu Leu Thr Glu
            180                 185                 190

```
Ile Asn Lys Asn Thr Thr Ile Asp Glu Ile Arg Ser Leu Thr Ala Ala
            195                 200                 205

Asp Leu Leu Ile Ser Asn Glu Leu Arg Pro Met Ala Val
    210                 215                 220

<210> SEQ ID NO 3
<211> LENGTH: 216
<212> TYPE: PRT
<213> ORGANISM: Artificial sequence
<220> FEATURE:
<223> OTHER INFORMATION: Synthesized: Acetate CoA--transferase subunit
      beta [Escherichia coli]

<400> SEQUENCE: 3

Met Asp Ala Lys Gln Arg Ile Ala Arg Arg Val Ala Gln Glu Leu Arg
1               5                   10                  15

Asp Gly Asp Ile Val Asn Leu Gly Ile Gly Leu Pro Thr Met Val Ala
            20                  25                  30

Asn Tyr Leu Pro Glu Gly Ile His Ile Thr Leu Gln Ser Glu Asn Gly
        35                  40                  45

Phe Leu Gly Leu Gly Pro Val Thr Thr Ala His Pro Asp Leu Val Asn
50                  55                  60

Ala Gly Gly Gln Pro Cys Gly Val Leu Pro Gly Ala Ala Met Phe Asp
65                  70                  75                  80

Ser Ala Met Ser Phe Ala Leu Ile Arg Gly Gly His Ile Asp Ala Cys
                85                  90                  95

Val Leu Gly Gly Leu Gln Val Asp Glu Glu Ala Asn Leu Ala Asn Trp
            100                 105                 110

Val Val Pro Gly Lys Met Val Pro Gly Met Gly Gly Ala Met Asp Leu
        115                 120                 125

Val Thr Gly Ser Arg Lys Val Ile Ile Ala Met Glu His Cys Ala Lys
    130                 135                 140

Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
            180                 185                 190

Ala Thr Val Arg Ala Lys Thr Glu Ala Arg Phe Glu Val Ala Ala Asp
        195                 200                 205

Leu Asn Thr Gln Arg Gly Asp Leu
    210                 215

<210> SEQ ID NO 4
<211> LENGTH: 216
<212> TYPE: PRT
<213> ORGANISM: Artificial sequence
<220> FEATURE:
<223> OTHER INFORMATION: Synthesized: Modified Acetate CoA--transferase
      subunit beta [Escherichia coli]

<400> SEQUENCE: 4

Met Asp Ala Lys Gln Arg Ile Ala Arg Arg Val Ala Gln Glu Leu Arg
1               5                   10                  15

Asp Gly Asp Ile Val Asn Leu Gly Ile Gly Leu Pro Thr Met Val Ala
            20                  25                  30

Asn Tyr Leu Pro Glu Gly Ile His Ile Thr Leu Gln Ser Asp Asn Gly
        35                  40                  45
```

```
Phe Leu Gly Leu Gly Pro Val Thr Thr Ala His Pro Asp Leu Val Asn
    50                  55                  60

Ala Gly Gly Gln Pro Cys Gly Val Leu Pro Gly Ala Ala Met Phe Asp
65                  70                  75                  80

Ser Ala Met Ser Phe Ala Leu Ile Arg Gly Gly His Ile Asp Ala Cys
                85                  90                  95

Val Leu Gly Gly Leu Gln Val Asp Glu Glu Ala Asn Leu Ala Asn Trp
            100                 105                 110

Val Val Pro Gly Lys Met Val Pro Gly Met Gly Ala Met Asp Leu
            115                 120                 125

Val Thr Gly Ser Arg Lys Val Ile Ile Ala Met Glu His Cys Ala Lys
130                 135                 140

Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
            180                 185                 190

Ala Thr Val Arg Ala Lys Thr Glu Ala Arg Phe Glu Val Ala Ala Asp
            195                 200                 205

Leu Asn Thr Gln Arg Gly Asp Leu
    210                 215

<210> SEQ ID NO 5
<211> LENGTH: 531
<212> TYPE: PRT
<213> ORGANISM: Artificial sequence
<220> FEATURE:
<223> OTHER INFORMATION: Synthesized: Acetate CoA-transferase YdiF
      [Escherichia coli]

<400> SEQUENCE: 5

Met Lys Pro Val Lys Pro Pro Arg Ile Asn Gly Arg Val Pro Val Leu
1               5                   10                  15

Ser Ala Gln Glu Ala Val Asn Tyr Ile Pro Asp Glu Ala Thr Leu Cys
            20                  25                  30

Val Leu Gly Ala Gly Gly Gly Ile Leu Glu Ala Thr Thr Leu Ile Thr
        35                  40                  45

Ala Leu Ala Asp Lys Tyr Lys Gln Thr Gln Thr Pro Arg Asn Leu Ser
    50                  55                  60

Ile Ile Ser Pro Thr Gly Leu Gly Asp Arg Ala Asp Arg Gly Ile Ser
65                  70                  75                  80

Pro Leu Ala Gln Glu Gly Leu Val Lys Trp Ala Leu Cys Gly His Trp
                85                  90                  95

Gly Gln Ser Pro Arg Ile Ser Glu Leu Ala Glu Gln Asn Lys Ile Ile
            100                 105                 110

Ala Tyr Asn Tyr Pro Gln Gly Val Leu Thr Gln Thr Leu Arg Ala Ala
        115                 120                 125

Ala Ala His Gln Pro Gly Ile Ile Ser Asp Ile Gly Ile Gly Thr Phe
    130                 135                 140

Val Asp Pro Arg Gln Gln Gly Gly Lys Leu Asn Glu Val Thr Lys Glu
145                 150                 155                 160

Asp Leu Ile Lys Leu Val Glu Phe Asp Asn Lys Glu Tyr Leu Tyr Tyr
                165                 170                 175
```

```
Lys Ala Ile Ala Pro Asp Ile Ala Phe Ile Arg Ala Thr Thr Cys Asp
            180                 185                 190

Ser Glu Gly Tyr Ala Thr Phe Glu Asp Glu Val Met Tyr Leu Asp Ala
        195                 200                 205

Leu Val Ile Ala Gln Ala Val His Asn Asn Gly Gly Ile Val Met Met
    210                 215                 220

Gln Val Gln Lys Met Val Lys Ala Thr Leu His Pro Lys Ser Val
225                 230                 235                 240

Arg Ile Pro Gly Tyr Leu Val Asp Ile Val Val Asp Pro Asp Gln
                245                 250                 255

Thr Gln Leu Tyr Gly Gly Ala Pro Val Asn Arg Phe Ile Ser Gly Asp
            260                 265                 270

Phe Thr Leu Asp Asp Ser Thr Lys Leu Ser Leu Pro Leu Asn Gln Arg
        275                 280                 285

Lys Leu Val Ala Arg Arg Ala Leu Phe Glu Met Arg Lys Gly Ala Val
    290                 295                 300

Gly Asn Val Gly Val Gly Ile Ala Asp Gly Ile Gly Leu Val Ala Arg
305                 310                 315                 320

Glu Glu Gly Cys Ala Asp Asp Phe Ile Leu Thr Val Glu Thr Gly Pro
                325                 330                 335

Ile Gly Gly Ile Thr Ser Gln Gly Ile Ala Phe Gly Ala Asn Val Asn
            340                 345                 350

Thr Arg Ala Ile Leu Asp Met Thr Ser Gln Phe Asp Phe Tyr His Gly
        355                 360                 365

Gly Gly Leu Asp Val Cys Tyr Leu Ser Phe Ala Glu Val Asp Gln His
    370                 375                 380

Gly Asn Val Gly Val His Lys Phe Asn Gly Lys Ile Met Gly Thr Gly
385                 390                 395                 400

Gly Phe Ile Asp Ile Ser Ala Thr Ser Lys Lys Ile Ile Phe Cys Gly
                405                 410                 415

Thr Leu Thr Ala Gly Ser Leu Lys Thr Glu Ile Thr Asp Gly Lys Leu
            420                 425                 430

Asn Ile Val Gln Glu Gly Arg Val Lys Lys Phe Ile Arg Glu Leu Pro
        435                 440                 445

Glu Ile Thr Phe Ser Gly Lys Ile Ala Leu Glu Arg Gly Leu Asp Val
    450                 455                 460

Arg Tyr Ile Thr Glu Arg Ala Val Phe Thr Leu Lys Glu Asp Gly Leu
465                 470                 475                 480

His Leu Ile Glu Ile Ala Pro Gly Val Asp Leu Gln Lys Asp Ile Leu
                485                 490                 495

Asp Lys Met Asp Phe Thr Pro Val Ile Ser Pro Glu Leu Lys Leu Met
            500                 505                 510

Asp Glu Arg Leu Phe Ile Asp Ala Ala Met Gly Phe Val Leu Pro Glu
        515                 520                 525

Ala Ala His
    530

<210> SEQ ID NO 6
<211> LENGTH: 531
<212> TYPE: PRT
<213> ORGANISM: Artificial sequence
<220> FEATURE:
<223> OTHER INFORMATION: Synthesized: Modified Acetate CoA-transferase
      YdiF [Escherichia coli]
```

<400> SEQUENCE: 6

```
Met Lys Pro Val Lys Pro Pro Arg Ile Asn Gly Arg Val Pro Val Leu
1               5                   10                  15

Ser Ala Gln Glu Ala Val Asn Tyr Ile Pro Asp Glu Ala Thr Leu Cys
            20                  25                  30

Val Leu Gly Ala Gly Gly Gly Ile Leu Glu Ala Thr Thr Leu Ile Thr
        35                  40                  45

Ala Leu Ala Asp Lys Tyr Lys Gln Thr Gln Thr Pro Arg Asn Leu Ser
    50                  55                  60

Ile Ile Ser Pro Thr Gly Leu Gly Asp Arg Ala Asp Arg Gly Ile Ser
65                  70                  75                  80

Pro Leu Ala Gln Glu Gly Leu Val Lys Trp Ala Leu Cys Gly His Trp
                85                  90                  95

Gly Gln Ser Pro Arg Ile Ser Glu Leu Ala Glu Gln Asn Lys Ile Ile
            100                 105                 110

Ala Tyr Asn Tyr Pro Gln Gly Val Leu Thr Gln Thr Leu Arg Ala Ala
        115                 120                 125

Ala Ala His Gln Pro Gly Ile Ile Ser Asp Ile Gly Ile Gly Thr Phe
    130                 135                 140

Val Asp Pro Arg Gln Gln Gly Gly Lys Leu Asn Glu Val Thr Lys Glu
145                 150                 155                 160

Asp Leu Ile Lys Leu Val Glu Phe Asp Asn Lys Glu Tyr Leu Tyr Tyr
                165                 170                 175

Lys Ala Ile Ala Pro Asp Ile Ala Phe Ile Arg Ala Thr Thr Cys Asp
            180                 185                 190

Ser Glu Gly Tyr Ala Thr Phe Glu Asp Glu Val Met Tyr Leu Asp Ala
        195                 200                 205

Leu Val Ile Ala Gln Ala Val His Asn Asn Gly Ile Val Met Met
    210                 215                 220

Gln Val Gln Lys Met Val Lys Lys Ala Thr Leu His Pro Lys Ser Val
225                 230                 235                 240

Arg Ile Pro Gly Tyr Leu Val Asp Ile Val Val Asp Pro Asp Gln
                245                 250                 255

Thr Gln Leu Tyr Gly Gly Ala Pro Val Asn Arg Phe Ile Ser Gly Asp
            260                 265                 270

Phe Thr Leu Asp Asp Ser Thr Lys Leu Ser Leu Pro Leu Asn Gln Arg
        275                 280                 285

Lys Leu Val Ala Arg Arg Ala Leu Phe Glu Met Arg Lys Gly Ala Val
    290                 295                 300

Gly Asn Val Gly Val Gly Ile Ala Asp Gly Ile Gly Leu Val Ala Arg
305                 310                 315                 320

Glu Glu Gly Cys Ala Asp Asp Phe Ile Leu Thr Val Asp Thr Gly Pro
                325                 330                 335

Ile Gly Gly Ile Thr Ser Gln Gly Ile Ala Phe Gly Ala Asn Val Asn
            340                 345                 350

Thr Arg Ala Ile Leu Asp Met Thr Ser Gln Phe Asp Phe Tyr His Gly
        355                 360                 365

Gly Gly Leu Asp Val Cys Tyr Leu Ser Phe Ala Glu Val Asp Gln His
    370                 375                 380

Gly Asn Val Gly Val His Lys Phe Asn Gly Lys Ile Met Gly Thr Gly
385                 390                 395                 400

Gly Phe Ile Asp Ile Ser Ala Thr Ser Lys Lys Ile Ile Phe Cys Gly
                405                 410                 415
```

```
Thr Leu Thr Ala Gly Ser Leu Lys Thr Glu Ile Thr Asp Gly Lys Leu
                420                 425                 430

Asn Ile Val Gln Glu Gly Arg Val Lys Lys Phe Ile Arg Glu Leu Pro
            435                 440                 445

Glu Ile Thr Phe Ser Gly Lys Ile Ala Leu Glu Arg Gly Leu Asp Val
        450                 455                 460

Arg Tyr Ile Thr Glu Arg Ala Val Phe Thr Leu Lys Glu Asp Gly Leu
465                 470                 475                 480

His Leu Ile Glu Ile Ala Pro Gly Val Asp Leu Gln Lys Asp Ile Leu
                485                 490                 495

Asp Lys Met Asp Phe Thr Pro Val Ile Ser Pro Glu Leu Lys Leu Met
            500                 505                 510

Asp Glu Arg Leu Phe Ile Asp Ala Ala Met Gly Phe Val Leu Pro Glu
        515                 520                 525

Ala Ala His
    530
```

<210> SEQ ID NO 7
<211> LENGTH: 2433
<212> TYPE: DNA
<213> ORGANISM: Artificial sequence
<220> FEATURE:
<223> OTHER INFORMATION: Synthesized: PFLB

<400> SEQUENCE: 7

| | | |
|---|---|---|
| atgaccacac tgaaactgga cacgctcagc gaccgcatta aagcgcacaa aaatgcgctg | 60 |
| gtgcatattg tgaaaccgcc agtctgtacc gagcgcgcgc agcactatac cgagatgtat | 120 |
| caacaacatc tcgataagcc gatcccggta cgtcgcgcgc tggcactggc gcatcacctg | 180 |
| gcgaatcgca ccatctggat caaacacgat gagttgatca ttggcaacca ggcaagcgaa | 240 |
| gttcgcgccg cgccgatctt cccggaatat actgtctcgt ggatcgaaaa agagattgat | 300 |
| gatctggcag atcgtcccgg tgctggcttt gcgtgagcg aagagaacaa acgcgttctg | 360 |
| catgaagtgt gcccgtggtg gcgcggtcag accgtacagg atcgctgcta cggcatgttt | 420 |
| accgatgagc aaaaaggtct gctggcgacc ggaatcatta aagcggaagg caatatgacc | 480 |
| tccggcgatg cgcacctggc ggtgaatttc ccgctgctgc tggaaaaagg gcttgatggt | 540 |
| ctgcgcgagg aagtagcgga acgtcgctcg cgcatcaacc tgacggtgct ggaagattta | 600 |
| cacggtgagc aattcctgaa agcgattgat atcgtgctgg tggcagtcag tgaacacatt | 660 |
| gaacgtttcg ctgccctggc gcgtgaaatg gccgcgaccg aaaccgcgcga agccgtcgc | 720 |
| gatgaactgc tggcgatggc agaaaactgc gatcttatcg cccaccagcc gccgcagact | 780 |
| ttctggcagg cgctgcaact gtgttacttc atccagttga ttttgcagat cgaatctaac | 840 |
| ggtcactcag tatcgtttgg tcgtatggac cagtatctct acccgtacta tcgccgcgac | 900 |
| gttgaactca accagacgct ggatcgcgaa cacgccatcg agatgctgca tagctgctgg | 960 |
| ctgaaactgc tggaagtgaa caagatccgc tccggctcac actcaaaagc ctctgcggga | 1020 |
| agtccgctgt atcagaacgt cactattggc gggcaaaatc tggttgatgg tcaaccaatg | 1080 |
| gacgcggtga atccactctc ttacgcgatc ctcgaatcct gcgtcgcct gcgttccact | 1140 |
| cagcctaacc tcagcgtgcg ttaccatgca ggaatgagca acgatttcct cgacgcctgc | 1200 |
| gtacaggtga tccgttgcgg cttcgggatg ccggcgttca acaacgacga aatcgtgatc | 1260 |
| ccggaattta ttaaactcgg tattgaaccg caggacgctt atgactacgc agcgattggt | 1320 |
| tgtatagaaa ccgccgtcgg tggcaaatgg ggctatcgct gtaccggcat gagctttatc | 1380 |

-continued

```
aacttcgccc gcgtgatgct ggcggcgctg gaaggcgggc atgatgccac cagcggcaaa      1440
gtgttcctgc cacaagaaaa agcgttgtcg gcaggtaact tcaacaactt cgatgaagtg      1500
atggacgcgt gggatacgca aatccgttac tacacccgca atcaatcga atcgaatat       1560 gtcgtcgaca ccatgctgga agagaacgtg cacgatattc tctgctcggc gctggtggat      1620
gactgtattg agcgagcgaa aagtatcaag caaggcggcg cgaaatatga ctgggtttct      1680
ggcctgcagg tcggcattgc caacctcggc aacagcctgg cggcagtgaa gaaactggtg      1740
tttgaacaag gtgcgattgg tcagcaacag cttgctgccg cactggcaga tgacttcgac      1800
ggcctgactc acgagcagct gcgtcagcgg ctgattaacg gtgcgccgaa gtacggcaac      1860
gacgatgata ctgtcgatac gctgctggct cgcgcttatc agacctatat cgacgaactg      1920
aaacagtacc ataatccgcg ctacggtcgt ggtccggttg gcggcaacta ttacgcgggt      1980
acgtcatcaa tctccgctaa cgtaccgttt ggcgcgcaga ctatggcaac accggacggg      2040
cgtaaagccc acaccccgct ggcagaaggc gcaagcccgg cctccggtac tgaccatctt      2100
ggccctactg cggtcattgg ctcagtgggt aaactgccta cggcagcgat tctcggcggc      2160
gtgttgctca accagaaact gaatccggca acgctggaga cgaatctga caagcagaaa      2220 ctgatgatcc tgctgcgtac cttctttgaa gtgcataaag gctggcatat tcagtacaac      2280
atcgtttccc gcgaaacgct gctggatgcg aaaaaacatc ccgatcagta tcgcgatctg      2340
gtagtgcgtg tcgcgggcta ttccgcgttc ttcaccgcgc tctctccaga cgctcaggac      2400
gatatcatcg cccgtactga acatatgctg taa                                   2433
```

<210> SEQ ID NO 8
<211> LENGTH: 927
<212> TYPE: DNA
<213> ORGANISM: Artificial sequence
<220> FEATURE:
<223> OTHER INFORMATION: Synthesized: PFLA

<400> SEQUENCE: 8

```
atgcttgaac gaaatagaga ggcaactatg attttcaata ttcagcgcta ctcgacccat        60
gatggccccg gtatccgcac ggtcgtattt cttaaaggct gttcgctggg ctgccgctgg       120
tgtcagaacc cggaaagccg cgcccgcacg caggatctgc tgtatgacgc acgactgtgt       180
ctggaaggct gcgagctgtg cgctaaggcc gcgccggaag tgattgagcg cgcgctgaat       240
ggtttgctta ttcatcggga aaagttaacc ccggagcatc tgacggcgtt aaccgactgc       300
tgtccgacac aggcattaac cgtgtgtggt gaagtgaaaa gcgttgagga gatcatgacg       360
accgttctgc gcgataaacc gttttacgat cgcagcggcg gcggtttaac gctttcgggt       420
ggtgagccct ttatgcagcc ggaaatggcg atggcgctac tgcaagccag ccacgaggca       480
ggcattcata ctgcggtaga aacctgtctg catgtgccgt ggaaatatat cgccccttct       540
ctgccctata tcgatctgtt tcttgccgat ttaaaacacg ttgccgacgc gccgtttaaa       600
cagtggaccg acggtaacgc cgccagagtg ctggataacc tgaaaaaact cgccgcagcg       660
ggcaaaaaaa tcattatccg cgtgccgctg attcagggct ttaatgccga cgaaacctct       720
gtaaaagcca ttaccgattt tgccgccgac gagctgcacg ttggcgaaat tcattttctg       780
ccctaccaca cgctgggcat caacaaatat cacttactta atctgcccta tgacgccccg       840
gaaaaaccgc ttgatgcgcc agaactgctc gactttgccc agcagtatgc ctgccagaaa       900
gggttaaccg cgaccttacg aggataa                                          927
```

```
<210> SEQ ID NO 9
<211> LENGTH: 2415
<212> TYPE: DNA
<213> ORGANISM: Artificial sequence
<220> FEATURE:
<223> OTHER INFORMATION: Synthesized: PFLB

<400> SEQUENCE: 9
atggaaagtt taactttagt caacaacgct cttgtcaagt cagtttcagt taatgctgtt      60
gctgccacta aggttgctgg tgttagaatc agcaagccat ctcgtgctat tcacactact     120
ccaatgacca ctactagtct taaggttgct aagaaggctg ccttctctca atctaagact     180
tatgctactg ctccatgcat tactaatgat gctgctgcca agagtgaaat cgatgttgaa     240
ggttggatta agaagcacta cactccatat gaaggagatg gttctttcct tgctggtcca     300
actgaaaaga ctaagaagct ttttgccaag gctgaagaat acttagccaa ggaacgtgct     360
aacggtggtt tatacgatgt tgacccacac accccatcta ccattacttc tcacaagcca     420
ggttaccttg acaaagaaaa tgaagttatc tacggttacc aaactgatgt tccacttaag     480
agagccatta agccattcgg tggtgttaat atggtaaaga acgctcttaa ggctgttaac     540
gttccaatgg ataaggaagt tgaacacatt ttcactgatt accgtaagac tcacaacact     600
gctgtattcg atatttactc taaggaaatg agagctggtc gttccaatgc tatcatgacc     660
ggtttaccag atggttatgg tcgtggtcgt attattggtg attaccgtcg tgttgccctt     720
tacggtactg accgtcttat tgcccaaaag caaaaggata aggttgaatt acaaagagac     780 aaatggatg aaccaactat gaaattaatt ggtgaagttg ctgatcaaat taaggctctt     840
aagcaactta ctcaaatggc caagtcttac ggtattgata ttactaagcc agctaagaac     900
gccagagaag ctactcaatt cgtttacttc ggttacttag gttctatcaa ggaacaagat     960
ggtgctgcta tgtctcttgg tcgtgttgat gccttccttg attgtttctt cgaaaatgat    1020
ttaaagaatg gtgttcttga tgaagcccat gcccaagaaa ttattgataa ccttatctta    1080
aagttacgtt tcgctcgtca cttacgtact ccagaataca cgatttatt cgctggtgat    1140 ccaacctggg ttactatgtc tctcggtggt actggttctg atggtcgtac attagttacc    1200
aagacttcct tccgtgttct taacactctt tacaacttag tccagctcc agaaccaaac    1260 atcactgtcc tttggaacaa gaaccttcca aagaacttta aggactttgc tactaaggtt    1320
tctattgata cctcttccat tcaatacgaa tctgatgctc ttatgtccgc tagattcggt    1380
gatgactacg gtattgcttg ctgtgtctct gccatgagaa ttggtaagga tatgcaattc    1440
ttcggtgctc gttgtaacct tgctaagctt atgctttacg tcctcaacca tggtaaggat    1500
gaaagaactg gtaagcaagt tggtccagac tttggtccag ttccagatgg tccaattcca    1560
ttcgactgga tgtgggaaac ctatgacaag gctatggact ggattgccaa gctttacgtc    1620
aacaccatga cgttattca cttctgccat gaccaatact gttacgaatc ccttcaaatg    1680
gctcttcatg ataccgatgt ccgtcgtctt atggccttcg tgttgctgg tcttctgtt     1740 gttgctgatt cattctctgc tattaagtac gccaaggtta ctccaatccg tgatccaaag    1800
accggtttaa ctactgactt taaggttgaa ggtgaattcc caaaattcgg taatgatgat    1860
gaccgtgtcg atttcttcgc tcgtaccgtt actgataagc ttattaccaa gttaagaaaa    1920
actccaactt accgtggtgc cactcacact ctttccattc ttaccattac ctctaatgtc    1980
gtttacggta agaagaccgg ttctactcca gatggtcgta aggctggtca accattcgct    2040
ccaggttgta acccaatgca cggtcgtgaa ttctctggtg ctgttgcttc tctttctctca    2100
```

```
gtcgctaagg ttaactacga ctcttgtatg gatggtattt ctaacacctt ctctattgtt    2160
ccaaacacca ttggtaagac cttacaagaa cgtcaaggta acctttccgg tttattagat    2220
ggttacttca gcaagggtgc tcaccatctt aacgttaacg ttcttaagcg tgaaacttta    2280
gaagatgcca tggctcaccc agaaaactat ccaaacctta ctattcgtgt ttctggttat    2340
gctgttaact tgttaagtt aactccagct caacaaaagg aagtcattgc ccgtaccttc     2400
cacgaaaaga tgtaa                                                     2415
```

<210> SEQ ID NO 10
<211> LENGTH: 801
<212> TYPE: DNA
<213> ORGANISM: Artificial sequence
<220> FEATURE:
<223> OTHER INFORMATION: Synthesized: PFLA

<400> SEQUENCE: 10

```
atgccagcta tcgttgatcc aactactatg gattatatgg aagtcaaggg caatgtccat     60
tcaactgaaa gtttggcttg tcttgaaggt ccaggaaaca gattccttt attttaaat      120 ggttgtgctg ctcgttgctt atactgtagt aatccagata cttgggatga aactgttggt    180
actccaatga ccgttggcca acttattaag aagattggaa atcttaaaaa ctactatatc    240
aattctgttg gtggtggtgg tgtcactgtt tctggtggtg aaccattaac tcaatttggt    300
ttcttatctt gtttcttata tgctgtcaag aagcacttaa atcttcatac ctgtgttgaa    360
accactggtc aaggttgtac taaggcttgg aattcagttt tacctcatac tgacttatgc    420
ttagtatgta ttaaacatgc tattccagaa aaatacgaac aaattactcg tactaagaaa    480
ttagatagat gtcttaagtt ccttaaggaa ttagaaaaga gaaacattcc atggtggtgt    540
cgttacgttt tcttccagg ttacactgat tctaaggaag atattgaagc tttaattgaa    600
ttagttaaga acagtccaac ttgtgaaaga attgaattcc ttccataccc cgaattaggt    660
aaaaacaaat gggaagaatt aggtattgaa tatccattaa agaatattaa acaacttaag    720
aaaagtgaaa ttaaatggat ctgtgatatg gtccgtgaag ctttcaagga ccgtaatatt    780
ccagttactg gtgatactta a                                              801
```

<210> SEQ ID NO 11
<211> LENGTH: 1263
<212> TYPE: DNA
<213> ORGANISM: Artificial sequence
<220> FEATURE:
<223> OTHER INFORMATION: Synthesized: pda1

<400> SEQUENCE: 11

```
atgcttgctg cttcattcaa acgccaacca tcacaattgg tccgcgggtt aggagctgtt     60
cttcgcactc ccaccaggat aggtcatgtt cgtaccatgg caactttaaa aacaactgat    120
aagaaggccc ctgaggacat cgagggctcg gacacagtgc aaattgagtt gcctgaatct    180
tccttcgagt cgtatatgct agagcctcca gacttgtctt atgagacttc gaaagccacc    240 tgttacacaga tgtataaga tatggtcatc atcagaagaa tggagatggc ttgtgacgcc    300
ttgtacaagg ccaagaaaat cagaggtttt tgccatctat ctgttggtca ggaggccatt    360
gctgtcggta tcgagaatgc catcacaaaa ttggattcca tcatcacatc ttacagatgt    420
cacggtttca cttttatgag aggtgcctca gtgaaagccg ttctggctga attgatgggt    480
agaagagccg gtgtctctta tggtaagggt ggttccatgc acctttacgc tccaggcttc    540
tatggtggta atggtatcgt gggtgcccag gttccttag gtgcaggttt agcttttgct    600
```

```
caccaataca agaacgagga cgcctgctct ttcactttgt atggtgatgg tgcctctaat    660
caaggtcaag tttttgaatc tttcaacatg gccaaattat ggaatttgcc cgtcgtgttt    720
tgctgtgaga acaacaagta cggtatgggt accgccgctt caagatcctc cgcgatgact    780
gaatatttca agcgtggtca atatattcca ggtttaaaag ttaacggtat ggatattcta    840
gctgtctacc aagcatccaa gtttgctaag gactggtgtc tatccggcaa aggtcctctc    900
gttctagaat atgaaaccta taggtacggt ggccattcta tgtctgatcc cggtactacc    960
tacagaacta gagacgagat tcagcatatg agatccaaga cgatccaat tgctggtctt    1020 aagatgcatt tgattgatct aggtattgcc actgaagctg aagtcaaagc ttacgacaag    1080
tccgctagaa aatacgttga cgaacaagtt gaattagctg atgctgctcc tcctccagaa    1140
gccaaattat ccatcttgtt tgaagacgtc tacgtgaaag gtacagaaac tccaaccc ta   1200 agaggtagga tccctgaaga tacttgggac ttcaaaaagc aaggttttgc ctctagggat    1260
taa                                                                  1263

<210> SEQ ID NO 12
<211> LENGTH: 1101
<212> TYPE: DNA
<213> ORGANISM: Artificial sequence
<220> FEATURE:
<223> OTHER INFORMATION: Synthesized: pdb1

<400> SEQUENCE: 12
atgttttcca gactgccaac atcattggcc agaaatgttg cacgtcgtgc cccaacttct     60
tttgtaagac cctctgcagc agcagcagca ttgagattct catcaacaaa gacgatgacc    120
gtcagagagg ccttgaatag tgccatggcg gaagaattgg accgtgatga tgatgtcttc    180
cttattggtg aagaagttgc acaatataac ggggcttata agtgtcaaa gggtttattg     240 gacaggttcg gtgaacgtcg tgtggttgac acacctatta ccgaatacgg gttcacaggt    300
ttggccgttg gtgccgcttt gaagggtttg aagccaattg tagagtttat gtcgttcaat    360
ttctctatgc aagctatcga tcatgttgtc aattccgctg caaagactca ctacatgtct    420
ggtggtactc aaaaatgtca aatggtcttc agaggtccta atggtgctgc agtgggtctt    480
ggtgctcaac attcacagga cttttctcct tggtacggtt ccattccagg gttaaaggtc    540
cttgtccctt attctgctga agatgctagg ggttgttaa aggccgccat cagagatcca    600
aaccctgttg tatttttaga gaacgaattg ttgtacggtg aatcttttga aatctcagaa    660
gaagctttat cccctgagtt caccttgcca tacaaggcta gatcgaaag agaaggtacc    720 gatatttcca ttgttacgta cacaagaaac gttcagtttt ctttggaagc cgctgaaatt    780
ctacaaaaga aatatggtgt ctctgcagaa gttatcaact tgcgttctat tagacccttta   840 gatactgaag ctatcatcaa aactgtcaag aagacaaacc acttgattac tgttgaatcc    900
actttcccat catttggtgt tggtgctgaa attgtcgccc aagttatgga gtctgaagcc    960
tttgattact tggatgctcc aatccaaaga gttactggtg ccgatgttcc aacaccttac    1020
gctaaagaat tagaagattt cgctttccct gatactccaa ccatcgttaa agctgtcaaa    1080
gaagtcttgt caattgaata a                                              1101

<210> SEQ ID NO 13
<211> LENGTH: 1449
<212> TYPE: DNA
<213> ORGANISM: Artificial sequence
<220> FEATURE:
<223> OTHER INFORMATION: Synthesized: lat1
```

<400> SEQUENCE: 13

```
atgtctgcct tgtcagggt ggttccaaga atatccagaa gttcagtact caccagatca     60
ttgagactgc aattgagatg ctacgcatcg tacccagagc acaccattat tggtatgccg    120
gcactgtctc ctacgatgac gcaaggtaat cttgctgctt ggactaagaa ggaaggtgac    180
caattgtctc ccggtgaagt tattgccgaa atagaaacag acaaggctca aatggacttt    240
gagttccaag aagatggtta cttagccaag attctagttc ctgaaggtac aaaggacatt    300
cctgtcaaca agcctattgc cgtctatgtg gaggacaaag ctgatgtgcc agcttttaag    360
gactttaagc tggaggattc aggttctgat tcaaagacca gtacgaaggc tcagcctgcc    420
gaaccacagg cagaaaagaa acaagaagcg ccagctgaag agaccaagac ttctgcacct    480
gaagctaaga atctgacgt tgctgctcct caaggtagga ttttgcctc tccacttgcc     540
aagactatcg ccttggaaaa gggtatttct ttgaaggatg ttcacggcac tggaccccgc    600
ggtagaatta ccaaggctga cattgagtca tatctagaaa agtcgtctaa gcagtcttct    660
caaaccagtg gtgctgccgc cgccactcct gccgccgcta cctcaagcac tactgctggc    720
tctgctccat cgccttcttc tacagcatca tatgaggatg ttccaatttc aaccatgaga    780
agcatcattg gagaacgttt attgcaatct actcaaggca ttccatcata catcgtttcc    840
tccaagatat ccatctccaa acttttgaaa ttgagacagt ccttgaacgc tacagcaaac    900
gacaagtaca aactgtccat taatgaccta ttagtaaaag ccatcactgt tgcggctaag    960
agggtgccag atgccaatgc ctactggtta cctaatgaga cgttatccg taaattcaag    1020
aatgtcgatg tctcagtcgc tgttgccaca ccaacaggat tattgacacc aattgtcaag    1080
aattgtgagg ccaagggctt gtcgcaaatc tctaacgaaa tcaaggaact agtcaagcgt    1140
gccagaataa acaaattggc accagaggaa ttccaaggtg gaccatttg catatccaat    1200
atgggcatga ataatgctgt taacatgttt acttcgatta tcaacccacc acagtctaca    1260
atcttggcca tcgctactgt tgaaagggtc gctgtggaag acgccgctgc tgagaacgga    1320
ttctccttg ataaccaggt taccataaca gggacctttg atcatagaac cattgatggc     1380
gccaaaggtg cagaattcat gaaggaattg aaaactgtta ttgaaaatcc tttggaaatg    1440
ctattgtga                                                          1449
```

<210> SEQ ID NO 14
<211> LENGTH: 1500
<212> TYPE: DNA
<213> ORGANISM: Artificial sequence
<220> FEATURE:
<223> OTHER INFORMATION: Synthesized: lpd1

<400> SEQUENCE: 14

```
atgttaagaa tcagatcact cctaaataat aagcgtgcct tttcgtccac agtcaggaca     60
ttgaccatta acaagtcaca tgatgtagtc atcatcggtg gtggccctgc tggttacgtg    120
gctgctatca aagctgctca attgggattt aacactgcat gtgtagaaaa aagaggcaaa    180
ttaggcggta cctgtcttaa cgttggatgt atccctcca agcacttct aaataattct     240
catttattcc accaaatgca tacggaagcg caaagagag gtattgacgt caacggtgat    300
atcaaaatta acgtagcaaa cttccaaaag gctaaggatg acgctgttaa gcaattaact    360
ggaggtattg agcttctgtt caagaaaaat aaggtcacct attataaagg taatggttca    420
ttcgaagacg aaacgaagat cagagtaact cccgttgatg ggttggaagg cactgtcaag    480
gaagaccaca tactagatgt taagaacatc atagtcgcca cgggctctga agttacaccc    540
```

|  |  |  |  |  |  |
|---|---|---|---|---|---|
| ttccccggta | ttgaaataga | tgaggaaaaa | attgtctctt | caacaggtgc | tctttcgtta | 600 |
| aaggaaattc | ccaaaagatt | aaccatcatt | ggtggaggaa | tcatcggatt | ggaaatgggt | 660 |
| tcagtttact | ctagattagg | ctccaaggtt | actgtagtag | aatttcaacc | tcaaattggt | 720 |
| gcatctatgg | acggcgaggt | tgccaaagcc | acccaaaagt | tcttgaaaaa | gcaaggtttg | 780 |
| gacttcaaat | taagcaccaa | agttatttct | gcaaagagaa | cgacgacaa | gaacgtcgtc | 840 |
| gaaattgttg | tagaagatac | taaaacgaat | aagcaagaaa | attttgaagc | tgaagttttg | 900 |
| ctggttgctg | ttggtagaag | accttacatt | gctggcttag | gggctgaaaa | gattggatta | 960 |
| gaagtagaca | aaaggggacg | cctagtcatt | gatgaccaat | ttaattccaa | gttcccacac | 1020 |
| attaaagtgg | taggagatgt | tacatttggt | ccaatgctgg | ctcacaaagc | cgaagaggaa | 1080 |
| ggtattgcag | ctgtcgaaat | gttgaaaact | ggtcacggtc | atgtcaacta | taacaacatt | 1140 |
| ccttcggtca | tgtattctca | cccagaagta | gcatgggttg | gtaaaaccga | agagcaattg | 1200 |
| aaagaagccg | gcattgacta | taaaattggt | aagttcccct | tgcggccaa | ttcaagagcc | 1260 |
| aagaccaacc | aagacactga | aggtttcgtg | aagattttga | tcgattccaa | gaccgagcgt | 1320 |
| attttggggg | ctcacattat | cggtccaaat | gccggtgaaa | tgattgctga | agctggctta | 1380 |
| gccttagaat | atggcgcttc | cgcagaagat | gttgctaggg | tctgccatgc | tcatcctact | 1440 |
| ttgtccgaag | catttaagga | agctaacatg | gctgcctatg | ataaagctat | tcattgttga | 1500 |

<210> SEQ ID NO 15
<211> LENGTH: 1233
<212> TYPE: DNA
<213> ORGANISM: Artificial sequence
<220> FEATURE:
<223> OTHER INFORMATION: Synthesized: pdx1

<400> SEQUENCE: 15

|  |  |  |  |  |  |
|---|---|---|---|---|---|
| atgctaagtg | caatttccaa | agtctccact | ttaaaatcat | gtacaagata | tttaaccaaa | 60 |
| tgcaactatc | atgcatcagc | taaattactt | gctgtaaaga | cattttcaat | gcctgcaatg | 120 |
| tctcctacta | tggagaaagg | ggggattgtg | tcttggaaat | ataaagttgg | cgaaccattc | 180 |
| agcgcgggcg | atgtgatatt | agaagtggaa | acagataaat | ctcaaattga | tgtggaagca | 240 |
| ctggacgatg | gtaaactagc | taagatcctg | aaagatgaag | gctctaaaga | tgttgatgtt | 300 |
| ggtgaaccta | ttgcttatat | tgctgatgtt | gatgatgatt | tagctactat | aaagttaccc | 360 |
| caagaggcca | acaccgcaaa | tgcgaaatct | attgaaatta | gaagccatc | cgcagatagt | 420 |
| actgaagcaa | cacaacaaca | tttaaaaaaa | gccacagtta | caccaataaa | aaccgttgac | 480 |
| ggcagccaag | ccaatcttga | acagacgcta | ttaccatccg | tgtcattact | actggctgag | 540 |
| aacaatatat | ccaaacaaaa | ggctttgaag | gaaattgcgc | catctggttc | caacggtaga | 600 |
| ctattaaagg | gtgatgtgct | agcataccta | gggaaaatac | cacaagattc | ggttaacaag | 660 |
| gtaacagaat | ttatcaagaa | gaacgaacgt | ctcgatttat | cgaacattaa | acctatacag | 720 |
| ctcaaaccaa | aaatagccga | gcaagctcaa | acaaaagctg | ccgacaagcc | aaagattact | 780 |
| cctgtagaat | ttgaagagca | attagtgttc | catgctcccg | cctctattcc | gtttgacaaa | 840 |
| ctgagtgaat | cattgaactc | tttcatgaaa | gaagcttacc | agttctcaca | cggaacacca | 900 |
| ctaatggaca | caaattcgaa | atactttgac | cctatttcg | aggaccttgt | caccttgagc | 960 |
| ccaagagagc | caagatttaa | attttcctat | gacttgatgc | aaattcccaa | agctaataac | 1020 |
| atgcaagaca | cgtacggtca | agaagacata | tttgacctct | taacaggttc | agacgcgact | 1080 |
| gcctcatcag | taagacccgt | tgaaaagaac | ttacctgaaa | aaaacgaata | tatactagcg | 1140 |

| ttgaatgtta gcgtcaacaa caagaagttt aatgacgcgg aggccaaggc aaaaagattc | 1200 |
| cttgattacg taaggagtt agaatcattt tga | 1233 |

```
<210> SEQ ID NO 16
<211> LENGTH: 1116
<212> TYPE: DNA
<213> ORGANISM: Artificial sequence
<220> FEATURE:
<223> OTHER INFORMATION: Synthesized: pdhA

<400> SEQUENCE: 16
```

| atggcaaagg ctaagaaaca aaaacctatt gactttaaag agctaatggc taaagtcgac | 60 |
| gctgatttcc caactttcca atcttggat caagatggaa aaattgtgaa tgaagattta | 120 |
| gtacctgatt tatcggatga ggaattagtt gaattaatga cacgcatggt ttggtctcgt | 180 |
| gtgttagacc aacgttctac tgcattaaac cgtcaaggac gcttaggatt cttcgcgcca | 240 |
| acagctggac aagaagcaag ccaattggca agtcaatttg caatggaaaa agaagactac | 300 |
| ttactaccag gttaccgtga tgtacctcaa ttagtacaac atggtttacc attaagagaa | 360 |
| gctttcttat ggtctcgtgg tcacgtagca gggaactact acgcggaaga tttaaatgca | 420 |
| ttaccaccac aaattatcat tggtgctcaa tacatccaag cagctggtgt tgctttagga | 480 |
| ttgaaaaaac gtggaaaaga aatgttgtc ttcactttata ctggtgacgg cggttcttca | 540 |
| caaggggact tctatgaagc aattaacttt gctggtgctt accaagcaaa cggtgtcttc | 600 |
| attatccaaa acaatggttt tgcgatttct acacctcgtg aaaaacaaac agcggctaaa | 660 |
| actttagctc aaaaagctgt tgcagcagga attcctggta ttcaagttga tggtatggat | 720 |
| ccattagcag tttacgcaat tgcaaaagaa gcacgtgatt ggtcagctgc aggaaacggt | 780 |
| ccagttttaa ttgaaacatt aacctatcgt tatggtccac atactttatc tggagacgat | 840 |
| ccaacacgtt accgttcaaa agaaatggat gacgaatggg tacaaaaaga tccattgact | 900 |
| cgtttccgta atatctaac agataaaggc ttatggtctg aagcaaaaga gaagaaatt | 960 |
| attgaaaaaa caaagaaga atcaaagta gcgattgcag aagcggataa agcgccaaaa | 1020 |
| caaaaagttt ctgatttctt gaaaaatatg tttgaagttc aacctcaaac aattaaagaa | 1080 |
| caaattgcat tttatgaagc gaaggagtcg aaataa | 1116 |

```
<210> SEQ ID NO 17
<211> LENGTH: 735
<212> TYPE: DNA
<213> ORGANISM: Artificial sequence
<220> FEATURE:
<223> OTHER INFORMATION: Synthesized: adc

<400> SEQUENCE: 17
```

| atgttaaagg atgaagtaat taaacaaatt agcacgccat taacttcgcc tgcatttcct | 60 |
| agaggacccct ataaatttca taatcgtgag tattttaaca ttgtatatcg tacagatatg | 120 |
| gatgcacttc gtaaagttgt gccagagcct ttagaaattg atgagccctt agtcaggttt | 180 |
| gaaattatgg caatgcatga tacgagtgga cttggttgtt atacagaaag cggacaggct | 240 |
| attcccgtaa gctttaatgg agttaaggga gattatcttc atatgatgta tttagataat | 300 |
| gagcctgcaa ttgcagtagg aagggaatta agtgcatatc ctaaaaagct cgggtatcca | 360 |
| aagcttttg tggattcaga tactttagta ggaactttag actatggaaa acttagagtt | 420 |
| gcgacagcta caatggggta caaacataaa gccttagatg ctaatgaagc aaaggatcaa | 480 |
| atttgtcgcc ctaattatat gttgaaaata ataccaatt atgatggaag ccctagaata | 540 |

| | |
|---|---|
| tgtgagctta taaatgcgaa aatcacagat gttaccgtac atgaagcttg acaggacca | 600 |
| actcgactgc agttatttga tcacgctatg gcgccactta atgatttgcc agtaaaagag | 660 |
| attgtttcta gctctcacat tcttgcagat ataatattgc ctagagctga agttatatat | 720 |
| gattatctta agtaa | 735 |

<210> SEQ ID NO 18
<211> LENGTH: 741
<212> TYPE: DNA
<213> ORGANISM: Artificial sequence
<220> FEATURE:
<223> OTHER INFORMATION: Synthesized: adc

<400> SEQUENCE: 18

| | |
|---|---|
| atgttagaaa gtgaagtatc taaacaaatt acaactccac ttgctgctcc agcgtttcct | 60 |
| agaggaccat ataggtttca caatagagaa tatctaaaca ttatttatcg aactgattta | 120 |
| gatgctcttc gaaaaatagt accagagcca cttgaattag atagagcata tgttagattt | 180 |
| gaaatgatgg ctatgcctga tacaaccgga ctaggctcat atacagaatg tggtcaagct | 240 |
| attccagtaa aatataatgg tgttaagggt gactacttgc atatgatgta tctagataat | 300 |
| gaacctgcta ttgctgttgg aagagaaagt agcgcttatc aaaaaagct tggctatcca | 360 |
| aagctatttg ttgattcaga tactttagtt gggacactta aatatggtac attaccagta | 420 |
| gctactgcaa caatgggata taagcacgag cctctagatc ttaaagaagc ctatgctcaa | 480 |
| attgcaagac ccaattttat gctaaaaatc attcaaggtt acgatggtaa gccaagaatt | 540 |
| tgtgaactaa tatgtgcaga aaatactgat ataactattc acggtgcttg gactggaagt | 600 |
| gcacgtctac aattatttag ccatgcacta gctcctcttg ctgatttacc tgtattagag | 660 |
| attgtatcag catctcatat cctcacagat ttaactcttg gaacacctaa ggttgtacat | 720 |
| gattatcttt cagtaaaata a | 741 |

<210> SEQ ID NO 19
<211> LENGTH: 1056
<212> TYPE: DNA
<213> ORGANISM: Artificial sequence
<220> FEATURE:
<223> OTHER INFORMATION: Synthesized: adh

<400> SEQUENCE: 19

| | |
|---|---|
| atgaaaggtt ttgcaatgct aggtattaat aagttaggat ggatcgaaaa agaaaggcca | 60 |
| gttgcgggtt catatgatgc tattgtacgc ccattagcag tatctccgtg tacatcagat | 120 |
| atacatactg tttttgaggg agctcttgga gataggaaga atatgatttt agggcatgaa | 180 |
| gctgtaggtg aagttgttga agtaggaagt gaagtgaagg attttaaacc tggtgacaga | 240 |
| gttatagttc cttgtacaac tccagattgg agatctttgg aagttcaagc tggttttcaa | 300 |
| cagcactcaa acggtatgct cgcaggatgg aaatttcaa atttcaagga tggagttttt | 360 |
| ggtgaatatt ttcatgtaaa tgatgcggat atgaatcttg cgattctacc taaagacatg | 420 |
| ccattagaaa atgctgttat gataacagat atgatgacta ctggatttca tggagcagaa | 480 |
| cttgcagata ttcaaatggg ttcaagtgtt gtggtaattg cattggagc tgttggctta | 540 |
| atgggaatag caggtgctaa attacgtgga gcaggtagaa taattggagt ggggagcagg | 600 |
| ccgatttgtg ttgaggctgc aaaatttat ggagcaacag atattctaaa ttataaaaat | 660 |
| ggtcatatag ttgatcaagt tatgaaatta acgaatggaa aaggcgttga ccgcgtaatt | 720 |
| atggcaggcg gtggttctga acattatcc caagcagtat ctatggttaa accaggagga | 780 |

```
ataatttcta atataaatta tcatggaagt ggagatgctt tactaatacc acgtgtagaa      840
tggggatgtg gaatggctca caagactata aaaggaggtc tttgtcctgg gggacgtttg      900
agagcagaaa tgttaagaga tatggtagta tataatcgtg ttgatctaag taaattagtt      960
acacatgtat atcatggatt tgatcacata gaagaagcac tgttattaat gaaagacaag     1020
ccaaaagact aattaaagc agtagttata ttataa                                 1056
```

```
<210> SEQ ID NO 20
<211> LENGTH: 414
<212> TYPE: DNA
<213> ORGANISM: Artificial sequence
<220> FEATURE:
<223> OTHER INFORMATION: Synthesized: mgsA

<400> SEQUENCE: 20
atgaaaattg ctttgatcgc gcatgacaag aaaaaacagg atatggttca atttacgact       60
gcctatcggg atattttaaa gaatcatgat ctatacgcaa ccggaaccac agggttgaaa      120
attcatgagg cgacaggtct tcaaattgaa cgttttcaat ccggcccttt aggggggagac    180 cagcaaatcg gtgcactgat cgctgccaat gcactcgatc ttgtcatttt tttgcgcgac      240
ccgctgaccg cgcagccgca tgaaccggat gtctcggcat taatccgttt atgtgatgtg      300
tattccattc cgctcgccac aaatatgggt actgcggaaa ttcttgtgcg cacacttgat      360
gaaggtgttt tcgaattccg tgaccttctt cggggagaag agccgaatgt ataa            414
```

```
<210> SEQ ID NO 21
<211> LENGTH: 459
<212> TYPE: DNA
<213> ORGANISM: Artificial sequence
<220> FEATURE:
<223> OTHER INFORMATION: Synthesized: mgsA

<400> SEQUENCE: 21
atggaactga cgactcgcac tttacctgcg cggaaacata ttgcgctggt ggcacacgat       60
cactgcaaac aaatgctgat gagctgggtg aacggcatc aaccgttact ggaacaacac      120
gtactgtatg caacaggcac taccggtaac ttaaatttccc gcgcgaccgg catgaacgtc    180
aacgcgatgt tgagtggccc aatgggggggt gaccagcagg ttggcgcatt gatctcagaa    240
gggaaaattg atgtattgat tttcttctgg gatccactaa atgccgtgcc gcacgatcct     300
gacgtgaaag ccttgctgcg tctggcgacg gtatggaaca ttccggtcgc caccaacgtg     360
gcaacggcag acttcataat ccagtcgccg catttcaacg acgcggtcga tattctgatc    420
cccgattatc agcgttatct cgcggaccgt ctgaagtaa                             459
```

```
<210> SEQ ID NO 22
<211> LENGTH: 459
<212> TYPE: DNA
<213> ORGANISM: Artificial sequence
<220> FEATURE:
<223> OTHER INFORMATION: Synthesized: mgsA

<400> SEQUENCE: 22
atggaactga cgactcgcac tttacctgcg cggaaacata ttgcgctggt ggcacacgat       60
caatgcaaac aaatgctgat gagctgggtg aacggcatc aaccgttact ggaacaacac      120
gtactgtatg caacaggcac taccggtaac ttaaatttccc gcgcgaccgg catgaacgtc    180
aacgcgatgt tgagtggccc aatgggggggt gaccagcagg ttggcgcatt gatctcagaa    240
gggaaaattg atgtattgat tttcttctgg gatccactaa atgccgtgcc gcacgatcct    300
```

| | |
|---|---|
| gacgtgaaag ccttgctgcg tctggcgacg gtatggaaca ttccggtcgc caccaacgtg | 360 |
| gcaacggcag acttcataat ccagtcgccg catttcaacg acgcggtcga tattctgatc | 420 |
| cccgattatc agcgttatct cgcggaccgt ctgaagtaa | 459 |

```
<210> SEQ ID NO 23
<211> LENGTH: 981
<212> TYPE: DNA
<213> ORGANISM: Artificial sequence
<220> FEATURE:
<223> OTHER INFORMATION: Synthesized: ydjg

<400> SEQUENCE: 23
```

| | |
|---|---|
| atgaaaaaga tacctttagg cacaacggat attacgcttt cgcgaatggg gttggggaca | 60 |
| tgggccattg gcggcggtcc tgcatggaat ggcgatctcg atcggcaaat atgtattgat | 120 |
| acgattcttg aagcccatcg ttgtggcatt aatctgattg atactgcgcc aggatataac | 180 |
| tttggcaata gtgaagttat cgtcggtcag gcgttaaaaa aactgccccg tgaacaggtt | 240 |
| gtagtagaaa ccaaatgcgg cattgtctgg aacgaaaaag aagtttatt caacaaagtt | 300 |
| ggcgatcggc agttgtataa aaacctttcc ccggaatcta ccgcgaaga ggtagcagcg | 360 |
| agcttgcaac gtctgggtat tgattacatc gatatctaca tgacgcactg gcagtcggtg | 420 |
| ccgccatttt ttacgccgat cgctgaaaact gtcgcagtgc ttaatgagtt aaagtctgaa | 480 |
| gggaaaattc gcgctatagg cgctgctaac gtcgatgctg accatatccg cgagtatctg | 540 |
| caatatggtg aactggatat tattcaggcg aaatacagta tcctcgaccg ggcaatggaa | 600 |
| aacgaactgc tgccactatg tcgtgataat ggcattgtgg ttcaggttta ttccccgcta | 660 |
| gagcagggat tgttgaccgg caccatcact cgtgattacg ttccgggcgg cgctcgggca | 720 |
| aataaagtct ggttccagcg tgaaaacatg ctgaaagtga ttgatatgct tgaacagtgg | 780 |
| cagccacttt gtgctcgtta tcagtgcaca attcccactc tggcactggc gtggatatta | 840 |
| aaacagagtg atttaatctc cattcttagt ggggctactg caccggaaca ggtacgcgaa | 900 |
| aatgtcgcgg cactgaatat caacttatcg gatgcagacg caacattgat gagggaaatg | 960 |
| gcagaggccc tggagcgtta a | 981 |

```
<210> SEQ ID NO 24
<211> LENGTH: 939
<212> TYPE: DNA
<213> ORGANISM: Artificial sequence
<220> FEATURE:
<223> OTHER INFORMATION: Synthesized: ypr1

<400> SEQUENCE: 24
```

| | |
|---|---|
| atgcctgcta cgttaaagaa ttcttctgct acattaaaac taaatactgg tgcctccatt | 60 |
| ccagtgttgg gtttcggcac ttggcgttcc gttgacaata gcggttacca ttctgtaatt | 120 |
| gcagctttga agctggata cagacacatt gatgctgcgg ctatctattt gaatgaagaa | 180 |
| gaagttggca gggctattaa agattccgga gtccctcgtg aggaaatttt tattactact | 240 |
| aagctttggg gtacggaaca acgtgatccg gaagctgctc taaacaagtc tttgaaaaga | 300 |
| ctaggcttgg attatgttga cctatatctg atgcattggc cagtgccttt gaaaaccgac | 360 |
| agagttactg atggtaacgt tctgtgtatt ccaacattag aagatggcac tgttgacatc | 420 |
| gatactaagg aatggaattt tatcaagacg tgggagttga tgcaagaatt gccaagacg | 480 |
| ggcaaaacta agccgttgg tgtctctaat ttttctatta caacattaa agaattatta | 540 |
| gaatctccaa ataacaaggt ggtaccagct actaatcaaa ttgaaattca tccattgcta | 600 |

| ccacaagacg | aattgattgc | cttttgtaaa | gaaaagggta | tcgttgttga | agcctactca | 660 |
| ccatttggga | gtgctaatgc | tcctttacta | aaagagcaag | caattattga | tatggctaaa | 720 |
| aagcacggtg | ttgagccagc | acagcttatt | atcagttgga | gtattcaaag | aggctacgtt | 780 |
| gttctggcca | aatcggttaa | tcctgaaaga | attgtatcca | attttaagat | tttcactctg | 840 |
| cccgaggatg | atttcaagac | tattagtaac | ctatccaaag | tgcatggtac | aaagagagtc | 900 |
| gttgatatga | agtggggatc | cttcccaatt | ttccaatga | | | 939 |

<210> SEQ ID NO 25
<211> LENGTH: 771
<212> TYPE: DNA
<213> ORGANISM: Artificial sequence
<220> FEATURE:
<223> OTHER INFORMATION: Synthesized: budC

<400> SEQUENCE: 25

| atgaaaaaag | tcgcacttgt | taccggcgcc | ggccagggga | ttggtaaagc | tatcgccctt | 60 |
| cgtctggtga | aggatggatt | tgccgtgcc | attgccgatt | ataacgacgc | caccgccaaa | 120 |
| gcggtcgcct | ccgaaatcaa | ccaggccggc | ggccgcgcca | tggcggtgaa | agtggatgtt | 180 |
| tctgaccgcg | accaggtatt | tgccgccgtc | gaacaggcgc | gcaaaacgct | gggcggcttc | 240 |
| gacgtcatcg | tcaacaacgc | cggcgtggcg | ccgtccacgc | cgatcgagtc | cattaccccg | 300 |
| gagattgtcg | acaaagtcta | caacatcaac | gtcaaagggg | tgatctgggg | catccaggcg | 360 |
| gcggtcgagg | cctttaagaa | agagggtcac | ggcgggaaaa | tcatcaacgc | ctgttcccag | 420 |
| gccggccacg | tcgtaacccc | ggagctggcg | gtgtatagct | cgagtaaatt | cgccgtacgc | 480 |
| ggcttaaccc | agaccgccgc | tcgcgacctc | gcgccgctgg | gcatcacggt | caacggctac | 540 |
| tgcccgggga | ttgtcaaaac | gccaatgtgg | gccgaaattg | accgcaggt | gtccgaagcc | 600 |
| gccggtaaac | cgctgggcta | cggtaccgcc | gagttcgcca | aacgcatcac | tctcggtcgt | 660 |
| ctgtccgagc | cggaagatgt | cgccgcctgc | gtctcctatc | ttgccagccc | ggattctgat | 720 |
| tacatgaccg | gtcagtcgtt | gctgatcgac | ggcgggatgg | tatttaacta | a | 771 |

<210> SEQ ID NO 26
<211> LENGTH: 1149
<212> TYPE: DNA
<213> ORGANISM: Artificial sequence
<220> FEATURE:
<223> OTHER INFORMATION: Synthesized: fucO

<400> SEQUENCE: 26

| atggctaaca | gaatgattct | gaacgaaacg | gcatggtttg | gtcggggtgc | tgttggggct | 60 |
| ttaaccgatg | aggtgaaacg | ccgtggttat | cagaaggcgc | tgatcgtcac | cgataaaacg | 120 |
| ctggtgcaat | gcggcgtggt | ggcgaaagtg | accgataaga | tggatgctgc | agggctggca | 180 |
| tgggcgattt | acgacggcgt | agtgcccaac | ccaacaatta | ctgtcgtcaa | agaagggctc | 240 |
| ggtgtattcc | agaatagcgg | cgcggattac | ctgatcgcta | ttggtggtgg | ttctccacag | 300 |
| gatacttgta | aagcgattgg | cattatcagc | aacaacccgg | agtttgccga | tgtgcgtagc | 360 |
| ctggaagggc | tttccccgac | caataaaccc | agtgtaccga | ttctggcaat | tcctaccaca | 420 |
| gcaggtactg | cggcagaagt | gaccattaac | tacgtgatca | ctgacgaaga | gaaacggcgc | 480 |
| aagtttgttt | gcgttgatcc | gcatgatatc | ccgcaggtgg | cgtttattga | cgctgacatg | 540 |
| atggatggta | tgcctccagc | gctgaaagct | gcgacgggtg | tcgatgcgct | cactcatgct | 600 |
| attgagggt | atattacccg | tggcgcgtgg | gcgctaaccg | atgcactgca | cattaaagcg | 660 |

| | |
|---|---|
| attgaaatca ttgctggggc gctgcgagga tcggttgctg gtgataagga tgccggagaa | 720 |
| gaaatggcgc tcgggcagta tgttgcgggt atgggcttct cgaatgttgg gttagggttg | 780 |
| gtgcatggta tggcgcatcc actgggcgcg ttttataaca ctccacacgg tgttgcgaac | 840 |
| gccatcctgt taccgcatgt catgcgttat aacgctgact ttaccggtga agtaccgc | 900 |
| gatatcgcgc gcgttatggg cgtgaaagtg aaggtatga gcctggaaga ggcgcgtaat | 960 |
| gccgctgttg aagcggtgtt tgctctcaac cgtgatgtcg gtattccgcc acatttgcgt | 1020 |
| gatgttggtg tacgcaagga agacattccg gcactggcgc aggcggcact ggatgatgtt | 1080 |
| tgtaccggtg caacccgcg tgaagcaacg cttgaggata ttgtagagct ttaccatacc | 1140 |
| gcctggtaa | 1149 |

```
<210> SEQ ID NO 27
<211> LENGTH: 804
<212> TYPE: DNA
<213> ORGANISM: Artificial sequence
<220> FEATURE:
<223> OTHER INFORMATION: Synthesized: yafB

<400> SEQUENCE: 27
```

| | |
|---|---|
| atggctatcc ctgcatttgg tttaggtact ttccgtctga agacgacgt tgttatttca | 60 |
| tctgtgataa cggcgcttga acttggttat cgcgcaattg ataccgcaca aatctatgat | 120 |
| aacgaagccg cagtaggtca ggcgattgca gaaagtggcg tgccacgtca tgaactctac | 180 |
| atcaccacta aaatctggat tgaaaatctc agcaaagaca aattgatccc aagtctgaaa | 240 |
| gagagcctgc aaaaattgcg taccgattat gttgatctga cgctaatcca ctggccgtca | 300 |
| ccaaacgatg aagtctctgt tgaagagttt atgcaggcgc tgctggaagc caaaaaacaa | 360 |
| gggctgacgc gtgagatcgg tatttccaac ttcacgatcc cgttgatgga aaaagcgatt | 420 |
| gctgctgttg gtgctgaaaa catcgctact aaccagattg aactctctcc ttatctgcaa | 480 |
| aaccgtaaag tggttgcctg ggctaaacag cacggcatcc atattacttc ctatatgacg | 540 |
| ctggcgtatg gtaaggccct gaaagatgag gttattgctc gtatcgcagc taaacacaat | 600 |
| gcgactccgg cacaagtgat tctggcgtgg gctatggggg aaggttactc agtaattcct | 660 |
| tcttctacta aacgtaaaaa cctggaaagt aatcttaagg cacaaaattt acagcttgat | 720 |
| gccgaagata aaaagcgat cgccgcactg gattgcaacg accgcctggt tagcccggaa | 780 |
| ggtctggctc ctgaatggga ttaa | 804 |

```
<210> SEQ ID NO 28
<211> LENGTH: 2364
<212> TYPE: DNA
<213> ORGANISM: Artificial sequence
<220> FEATURE:
<223> OTHER INFORMATION: Synthesized: dhaB1

<400> SEQUENCE: 28
```

| | |
|---|---|
| atgataagta aaggatttag tacccaaaca gaaagaataa atattttaaa ggctcaaata | 60 |
| ttaaatgcta aaccatgtgt tgaatcagaa agagcaatat taataacaga atcatttaaa | 120 |
| caaacagaag gccagccagc aatttttaaga gagcattgg cattgaaaca catacttgaa | 180 |
| aatatcccta taacaattag agatcaagaa cttatagtgg aagtttaac taagaaccca | 240 |
| aggtcttcac aagtatttcc tgagtttttct aataagtggt tacaagatga attggatag | 300 |
| ttaaataaga gaactggaga tgcattccaa atttcagaag aaagtaaaga aaattaaaa | 360 |
| gatgtctttg agtattggaa tggaaagaca acaagtgagt tagcaacttc atatatgaca | 420 |

| gaggaaacaa gagaggcagt aaattgtgat gtatttactg taggaaacta ctattataat | 480 |
| ggcgtaggac atgtatctgt agattatgga aaagtattaa gggttggatt taatgggatt | 540 |
| ataaatgagg ctaaggaaca attagaaaaa acaggagta tagatcctga ttttataaag | 600 |
| aaagaaaaat tcctaaatag tgttattatc tcatgcgaag ctgcaataac atatgtaaat | 660 |
| agatatgcta aaaggctaa agagattgca gataatacaa gtgatgcaaa agaaaagct | 720 |
| gaattaaatg aaatagcaaa aatttgttca aaagtttcag gagagggagc taaatctttc | 780 |
| tatgaagcat gtcaattatt ttggtttatt catgcaataa taaatataga atctaatgga | 840 |
| cattctattt ctccagctag atttgatcaa tacatgtatc catattatga aaatgataaa | 900 |
| aatataacag ataagtttgc tcaagaatta atagattgta tctggattaa attaaatgat | 960 |
| attaataaag taagagatga gatttcaact aaacattttg gtggttaccc aatgtatcaa | 1020 |
| aacttaattg ttgggggtca aaattcagaa ggaaaagatg caactaataa agtatcatat | 1080 |
| atggcattag aagcagctgt ccatgtaaag ttgcctcagc catctttgtc agtaagaata | 1140 |
| tggaataaga ctccagatga attttgctt agagcagcag aattaactag agaagggtta | 1200 |
| ggacttcctg cttattataa tgatgaagtt attattccag cattagtttc tagaggtctt | 1260 |
| acattagaag atgcaagaga ctacggaata attggatgtg ttgaaccaca aaagccagga | 1320 |
| aaaacagaag gatggcatga ttcagcattc tttaatcttg caagaatagt agagttaact | 1380 |
| ataaattctg gatttgataa aaataaacag attggaccta aaactcaaaa ttttgaagaa | 1440 |
| atgaaatcct ttgatgaatt catgaaagct tataaagctc aaatggagta ttttgtaaaa | 1500 |
| catatgtgct gtgctgataa ttgcatagat attgcacatg cagaaagagc tccattacct | 1560 |
| ttcttgtcat caatggttga taattgtatc ggaaaaggaa agagccttca agatggtggt | 1620 |
| gcagaatata acttcagtgg accacaaggt gttggagtag ctaatattgg agattcatta | 1680 |
| gttgcagtta aaaaaattgt gtttgatgaa aataagatta ctccttcaga attaaagaaa | 1740 |
| acattaaata atgattttaa aaattcagaa gaaatacaag ccttactaaa aaatgctcct | 1800 |
| aagtttggaa atgatattga tgaagttgat aatttagcta gagagggtgc attagtatac | 1860 |
| tgtagagaag ttaataaata tacaaatcca aggggaggaa attttcaacc aggattatat | 1920 |
| ccatcttcaa ttaatgtata ttttggaagc ttaacaggtg ctactccaga tggaaggaaa | 1980 |
| tccggacaac cattagctga tggggtttct ccatcaagag ctgtgatgt atctggacct | 2040 |
| actgcagctt gtaactcagt tagtaaatta gatcattta tagcttcaaa tggaactta | 2100 |
| tttaatcaaa aattccatcc gtcagcatta aaggtgata atggattaat gaatttatca | 2160 |
| tcattaataa gaagttattt tgatcaaaag ggatttcatg ttcaatttaa tgtaatagat | 2220 |
| aaaaaaatat tacttgcagc acaaaaaaat cctgaaaaat atcaagattt aattgttaga | 2280 |
| gttgcaggat atagtgcaca gttcatttct ttagataaat ctattcaaaa tgatattatt | 2340 |
| gcaagaactg aacatgttat gtaa | 2364 |

<210> SEQ ID NO 29
<211> LENGTH: 915
<212> TYPE: DNA
<213> ORGANISM: Artificial sequence
<220> FEATURE:
<223> OTHER INFORMATION: Synthesized: dhaB2

<400> SEQUENCE: 29

| atgagtaagg agataaaagg cgttttattt aacatacaaa aatttcgtt acatgatggg | 60 |
| cctggaataa gaactatagt atttttaag ggatgttcaa tgtcgtgctt atggtgcagt | 120 |

```
aatccagaat cccaagatat taaacctcaa gtaatgttta ataaaaattt atgtacaaaa      180
tgtggaagat gtaaatctca atgtaaaagt gcagctattg atatgaattc agaatatagg      240
atagataaaa gcaaatgtac agagtgtaca aaatgtgttg ataattgctt aagcggggca      300
cttgttattg aaggaaggaa ttacagtgtt gaagacgtta taaggaatt gaaaaaagat       360 agtgttcaat atagaagatc aaacggtgga attacactat ctggagggga agtattactt     420
caaccagatt ttgcagtgga gcttttaaaa gagtgtaaat catatggctg gcacactgcc     480
attgaaacag caatgtatgt taatagtgaa tctgtaaaaa aagtaattcc atatatagat     540
ctggctatga ttgatataaa aagtatgaat gatgaaatcc ataggaaatt tacaggagtg     600
agtaacgaaa taatattaca aaacattaaa ttaagtgatg aattagctaa agaaataata     660
atcagaattc ctgtaataga aggatttaat gcagatttac aaagtatagg agcaatagct     720
caattttcaa aatcattaac aaatcttaaa agaatagatc ttcttccata ccataattat     780
ggagaaaata gtatcaagc aattggaaga gagtattctt tgaaagaact aaaatcacct      840
agtaaagaca aaatgaaag attaaaagct ttagttgaaa tcatgggaat accgtgcaca      900
attggagctg agtaa                                                      915
```

<210> SEQ ID NO 30
<211> LENGTH: 2532
<212> TYPE: DNA
<213> ORGANISM: Artificial sequence
<220> FEATURE:
<223> OTHER INFORMATION: Synthesized: b1

<400> SEQUENCE: 30

```
atgggaaatt atgatagtac tccaattgcg aagtcggatc gtataaaaag acttgtagat      60
catctgtatg caaagatgcc tgagattgag gcggcaagag cggaactgat cacagaatca     120
tttaaggcta cggaaggtca gccggtagtg atgcgcaaag cacgtgcttt tgaacatatt     180 ttaagaatc ttccgatcat tatcagacca gaagaattaa ttgtcggaag tacaacgatc      240
gcaccgagag gatgccagac atatccggaa ttttcatatg aatggttaga ggcagaattc     300
gaaacagtcg aaacaagaag tgctgatcca ttctatattt cagaggaaac aaaaaagaga     360
ttattagctg cagatgctta ctggaaagga aaaacaacca gtgagctggc aacttcctat     420
atggctccgg agacactccg tgccatgaaa cataatttct ttacaccggg caactatttt     480
tataatggtg taggacatgt aacagttcag tatgaaaccg tattggcgat cggtctgaat     540
ggtgtaaaag aaaagtcag aaaagagatg gagaactgcc attttggaga tgcggattat      600
tctaccaaga tgtgtttctt agaatccatc ctgatttcct gtgatgcagt catcactttat    660 gcaaatcgtt atgcgaaaat ggcagaagag atggcagaga agaaacagag tgcagcaaga     720
agacaggagc ttctgacaat tgcaagagta tgtaaaaatg taccggaatt ccctgctgaa     780
agcttccagg aggcgtgcca gtccttctgg ttcatccagc aggtattaca gattgaatcc     840
agtggacatt ctatttcacc gggacgtttt gaccagtata tgtatcctta ttacgagaag     900
gatttaaaag aaggcagtct cacccgtgag tacgcacagg aactgatcga ctgtatctgg     960
gtaaaattaa atgatctgaa taatgtcgt gatgccgcaa gtgcagaagg ttttgcagga     1020
tattccttat tccagaacct gatcgttggt ggacagacag ttcagggaag agacgctacc    1080
aatgatcttt cgtttatgtg catcactgcc agtgagcatg tattttttacc aatgccatcc    1140 ttatcgatcc gtgtgtggca tggatcatcc aaggcattat taatgcgtgc ggcagagctg    1200
acaagaaccg gtatcggttt accggcttat tataatgacg aagttatcat tcctgcattg    1260
```

| | | |
|---|---|---|
| gttcatcgtg gagcaaccat ggacgaggca aggaattaca acatcatcgg atgtgtagaa | 1320 | |
| ccgcaggttc cgggtaaaac agacggatgg cacgatgcag cgttcttcaa tatgtgccgc | 1380 | |
| ccattggaga tggtattttc caatggttat gacaatggag agatcgcaag tatccagacc | 1440 | |
| ggtaatgtgg agagcttcca gtcatttgat gaatttatgg aagcatacag aaaacagatg | 1500 | |
| ttatataaca tcgaattgat ggtaaatgca gataatgcaa ttgattatgc tcatgcaaag | 1560 | |
| cttgcaccat taccatttga gtcatgtctg gtagatgact gcatcaagcg gggaatgagt | 1620 | |
| gcacaggaag gcggagcaat ttataacttt accggtccgc agggctttgg tatcgcaaat | 1680 | |
| gtcgcagact ctttatatac gatcaagaag ctggtatttg aagaaaaacg cattaccatg | 1740 | |
| ggcgagttaa agaaagctct tgagatgaat tacggtaaag ggctggatgc cacaactgcc | 1800 | |
| ggagatattg caatgcaggt tgcaaaagga ttaaaagatg caggtcagga agtgggacct | 1860 | |
| gatgtgatag cgaatacgat cagacaggta ttagagatgg aattaccgga agatgtcagg | 1920 | |
| aagcgttatg aagagatcca tgaaatgatc cttgaacttc cgaaatacgg aaatgatatt | 1980 | |
| gatgaagtag atgagcttgc ccgcgaggca gcatatttct acacaagacc attagagaca | 2040 | |
| ttcaaaaatc caagaggtgg aatgtatcag gcaggtctct atccggtatc agccaatgtt | 2100 | |
| ccattaggag ctcagaccgg tgctactccg gacggaagat tagcacatac tccggtggca | 2160 | |
| gatggagtcg gaccgacatc aggattcgat atcagtggac cgacagcatc ctgtaactca | 2220 | |
| gttgcaaaat tagatcatgc gatcgcaagt aacggaacac tctttaatat gaaaatgcat | 2280 | |
| ccaacagcta tggctggaga aaggggctg gagagcttta tttctctgat tcgtggttac | 2340 | |
| tttgatcagc agggtatgca catgcagttt aatgtcgtag accgtgcaac tcttttggac | 2400 | |
| gcacaggctc atccagaaaa atacagtggg ctgatcgtac gtgtagccgg atattctgct | 2460 | |
| ttgtttacta cgttatcgaa atccttacag gatgatatca ttaagagaac agaacaggct | 2520 | |
| gataatcgat ag | 2532 | |

<210> SEQ ID NO 31
<211> LENGTH: 795
<212> TYPE: DNA
<213> ORGANISM: Artificial sequence
<220> FEATURE:
<223> OTHER INFORMATION: Synthesized: b2

<400> SEQUENCE: 31

| | | |
|---|---|---|
| atgaaagaat atttgaatac atccggcagg atttttgata ttcaaagata ttccatacat | 60 | |
| gatggtccgg gagtccgaac catagtcttc ttaaaaggat gtgcgttacg atgcagatgg | 120 | |
| tgctgtaatc cggaatcaca gtcttttgaa gtggaaacaa tgacgatcaa cggaaaacca | 180 | |
| aaggttatgg gcaaagatgt aactgtagcg gaggttatga agacagtaga agagacatg | 240 | |
| cctattatt tacagtccgg tggaggaatc actctttccg gtggtgaatg tacgcttcaa | 300 | |
| ccggagttct cattagggct tttaagagca gcaaagatt tgggaatatc aacagccatt | 360 | |
| gaaagtatgg cttatgcaaa atacgaagtg atcgaaacac tgcttccgta tctggatact | 420 | |
| tacttaatgg atattaagca tatgaatccg gaaaagcata agaatatac aggtcatgat | 480 | |
| aatctcagaa tgttggagaa tgcactcagg gtagcccaca gtgggcagac agaactgatc | 540 | |
| atccgtgttc ctgttattcc tggatttaat gctacagagc aggaattgct tgatatagcg | 600 | |
| aagtttgcag ataccttacc gggcgtcaga cagatccaca tattgcctta tcataacttt | 660 | |
| ggtcagggaa aatacgaagg attgaacaga gactatccaa tgggagatac agagaagcct | 720 | | tccaatgagc agatgaaggc atttcaggaa atgatccaaa aaaatacgtc attacactgc    780 cagattggtg gttaa    795

<210> SEQ ID NO 32
<211> LENGTH: 2580
<212> TYPE: DNA
<213> ORGANISM: Artificial sequence
<220> FEATURE:
<223> OTHER INFORMATION: Synthesized: adh

<400> SEQUENCE: 32
atgaaggtaa ctaatgttga agaactgatg aaaaaaatgc aggaagtgca aaatgctcaa     60
aaaaaatttg ggagttttac tcaggaacaa gtagatgaaa ttttcaggca agcagcacta    120
gcagctaaca gtgccagaat agatctagct aaaatggcag tggaagaaac taaaatggga    180
attgtagagg ataaggttat aaaaaatcat tttgttgcag aatacatata ataagtat     240 aaaaatgaaa aaacttgtgg gattttggaa gaagatgaag ctttggaat ggttaaaatt     300 gcagaacctg taggtgtgat tgcagcagta attccaacaa caaatccaac atctacagca    360
atatttaaag cattattagc tttgaaaaca agaaatggta aattttttc accacatcca    420 agagcaaaaa agtgtactat tgcagcagct aagttagttc ttgatgctgc agttaaagca    480
ggtgctccta aaggaattat aggttggata gatgaacctt ctattgaact ttcacagata    540
gtaatgaaag aagctgatat aatccttgca acaggtggtc aggtatggt taaagcagct    600 tattcttcag gtaaacctgc tataggggtt ggtcctggta acacacctgc tttaattgat    660
gaaagtgctg atattaaaat ggcagtaaat tcaatacttc tttccaaaac ttttgataat    720
ggtatgattt gtgcttcaga gcagtcggta gtagttgtag attcaatata tgaagaagtt    780
aagaaagaat ttgctcatag aggagcttat attttaagta aggatgaaac aactaaagtt    840
ggaaaaatac tcttagttaa tggtacatta aatgctggta tcgttggtca gagtgcttat    900
aaaatagcag aaatggcagg agttaaagtt ccagaagatg ctaaagttct tataggagaa    960
gtaaaatcag tggagcattc agaagagcca ttttcacatg aaaagttatc tccagtttta   1020
gctatgtata gagctaaaaa ttttgatgaa gctcttttaa aagctggaag attagttgaa   1080
ctcggtggaa tgggtcatac atctgtatta tatgtaaatg caataactga aaaagtaaaa   1140
gtagaaaaat ttagagaaac tatgaagact ggtagaacat aataaaatat gccttcagca   1200
caaggtgcta taggagacat atataacttt aaactagctc cttcattaac attaggttgt   1260
ggttcatggg gaggaaactc cgtatcagaa atgttggac ctaaacactt attaaatata   1320
aaaagtgttg ctgagaggag agaaaatatg ctttggttta gagttcctga aaaggtttat   1380
tttaaatatg gtagtcttgg agttgcatta aagaattag atattttgga taagaaaaaa   1440
gtatttatag taacagataa agttctttat caattaggtt atatagatag agttacaaag   1500
attcttgaag aattgaaaat ttcatataaa atatttacag atgtagaacc agatccaacc   1560
ctagctacag ctaaaaaagg tgcagaagaa ttgttatcat ttaatccaga tactattata   1620
gcagttggtg gtggttcagc aatggatgct gctaagatta tgtgggtaat gtatgaacat   1680
ccggaagtaa gatttgaaga tttagctatg agatttatgg atataagaaa gagagtatat   1740
acttttccta agatgggtga aaaagcaatg atgatttctg ttgcaacatc agcaggaaca   1800
ggatcagaag taacacccttt tgcagtaatt actgatgaaa aaacaggagc taaatatcca   1860
ttagctgatt atgaattaac tccaaatatg gctataattg atgctgaact tatgatgggt   1920
atgccaaaag gattaacagc agcttcagga atagatgcac taactcatgc aatagaagct   1980

| tatgtatcaa | taatggcttc | agaatatact | aatggattag | cgttagaagc | aataagattg | 2040 |
| atatttaagt | atttaccaat | agcttacagt | gaaggaacaa | caagtataaa | ggcaagagaa | 2100 |
| aaaatggcgc | atgcttcaac | aatagctggt | atggcatttg | ctaatgcatt | tttaggagta | 2160 |
| tgtcattcaa | tggcacataa | attaggatca | actcatcacg | taccacatgg | cattgccaat | 2220 |
| gcactactta | taaatgaagt | tataaaattt | aatgcagtag | aaaatccaag | aaaacaagct | 2280 |
| gcatttccac | aatataagta | tccaaatata | aaaagagat | atgctagaat | agcagattac | 2340 |
| cttaacttag | gtgggtcaac | agacgatgaa | aaagtacaat | tattaataaa | tgctatagat | 2400 |
| gaattaaaag | ctaagataaa | tattccagaa | agtattaaag | aagcaggagt | aacagaagaa | 2460 |
| aaatttatg | ctactttaga | taaaatgtca | gaattagctt | ttgatgatca | atgtacaggt | 2520 |
| gcaaacccta | gatatccatt | aataagtgaa | ataaaacaaa | tgtatgtaaa | tgcattttaa | 2580 |

<210> SEQ ID NO 33
<211> LENGTH: 990
<212> TYPE: DNA
<213> ORGANISM: Artificial sequence
<220> FEATURE:
<223> OTHER INFORMATION: Synthesized: ldhA

<400> SEQUENCE: 33

| atgaaactcg | ccgtttatag | cacaaaacag | tacgacaaga | agtacctgca | acaggtgaac | 60 |
| gagtcctttg | gctttgagct | ggaattttt | gactttctgc | tgacgaaaaa | aaccgctaaa | 120 |
| actgccaatg | gctgcgaagc | ggtatgtatt | tcgtaaacg | atgacggcag | ccgcccggtg | 180 |
| ctggaagagc | tgaaaaagca | cggcgttaaa | tatatcgccc | tgcgctgtgc | cggtttcaat | 240 |
| aacgtcgacc | ttgacgcggc | aaaagaactg | gggctgaaag | tagtccgtgt | tccagcctat | 300 |
| gatccagagg | ccgttgctga | acacgccatc | ggtatgatga | tgacgctgaa | ccgccgtatt | 360 |
| caccgcgcgt | atcagcgtac | ccgtgatgct | aacttctctc | tggaaggtct | gaccggcttt | 420 |
| actatgtatg | gcaaaacggc | aggcgttatc | ggtaccggta | aaatcggtgt | ggcgatgctg | 480 |
| cgcattctga | aggttttggg | tatgcgtctg | ctggcgttcg | atccgtatcc | aagtgcagcg | 540 |
| gcgctggaac | tcgtgtgga | gtatgtcgat | ctgccaaccc | tgttctctga | atcagacgtt | 600 |
| atctctctgc | actgcccgct | gacaccggaa | aactatcatc | tgttgaacga | agccgccttc | 660 |
| gaacagatga | aaaatggcgt | gatgatcgtc | aataccagtc | gcggtgcatt | gattgattct | 720 |
| caggcagcaa | ttgaagcgct | gaaaaatcag | aaaattggtt | cgttgggtat | ggacgtgtat | 780 |
| gagaacgaac | gcgatctatt | cttgaagat | aaatccaacg | acgtgatcca | ggatgacgta | 840 |
| ttccgtcgcc | tgtctgcctg | ccacaacgtg | ctgtttaccg | gcaccaggc | attcctgaca | 900 |
| gcagaagcac | tgaccagtat | ttctcagact | acgctgcaaa | acttaagcaa | tctggaaaaa | 960 |
| ggcgaaacct | gcccgaacga | actggtttaa | | | | 990 |

<210> SEQ ID NO 34
<211> LENGTH: 930
<212> TYPE: DNA
<213> ORGANISM: Artificial sequence
<220> FEATURE:
<223> OTHER INFORMATION: Synthesized: ldhL2

<400> SEQUENCE: 34

| atggataaga | agcaacgcaa | agtcgtaatt | gttggtgatg | gctcggtggg | ttcatcattt | 60 |
| gccttttcat | tggtccaaaa | ttgcgcccta | gatgaactcg | ttatcgttga | cttggttaaa | 120 |
| acgcacgcag | aggggggacgt | taaggatttg | gaagatgttg | ccgcctttac | gaatgcgacc | 180 |

| | |
|---|---|
| aacattcata ccggtgaata tgcggatgcg cgtgatgctg acatcgttgt cattacggct | 240 |
| ggtgtgcctc gtaagcctgg tgagagtcgt ttagatttga ttaaccgcaa tacgaagatt | 300 |
| ctggaatcca tcgtcaaacc agtggttgcg agtggtttta atggttgctt cgttatctca | 360 |
| agtaatcccg tcgatatttt gacttcgatg acgcaacgtt tatccggttt tccacggcat | 420 |
| cgggtcattg gtaccgggac ttccttggat acggcgcggt tacgggtcgc cttggctcag | 480 |
| aagttgaatg ttgccaccac tgcagttgat gctgcggtac ttggagaaca tggtgatagt | 540 |
| tccatcgtta attttgatga aattatgatc aatgctcagc ccttaaagac ggtcacaacg | 600 |
| gtcgatgatc agttcaaagc tgaaatcgag caagctgttc gtggtaaagg tggtcaaatc | 660 |
| attagtcaga agggggccac gttctatggg gtcgccgtta gtttgatgca aatctgccga | 720 |
| gcaattttga acgatgaaaa tgctgagttg attgtctccg ccgctttgtc tggtcaatat | 780 |
| ggcattaacg atttgtactt ggggtcaccc gccattatta accgcaacgg gctccaaaaa | 840 |
| gtgatcgaag ctgagctatc agatgatgag cgtgcccgga tgcaacattt cgcagccaag | 900 |
| atgctgacca tgatgaatgt ggcatcataa | 930 |

<210> SEQ ID NO 35
<211> LENGTH: 999
<212> TYPE: DNA
<213> ORGANISM: Artificial sequence
<220> FEATURE:
<223> OTHER INFORMATION: Synthesized: ldh2

<400> SEQUENCE: 35

| | |
|---|---|
| atggcaactc tcaaggatca gctgattcag aatcttctta aggaagaaca tgtcccccag | 60 |
| aataagatta caattgttgg ggttggtgct gttggcatgg cctgtgccat cagtatctta | 120 |
| atgaaggact tggcagatga agttgctctt gttgatgtca tggaagataa actgaaggga | 180 |
| gagatgatgg atctccaaca tggcagcctt ttccttagaa caccaaaaat tgtctctggc | 240 |
| aaagactata atgtgacagc aaactccagg ctggttatta tcacagctgg ggcacgtcag | 300 |
| caagagggag agagccgtct gaatttggtc cagcgtaacg tgaacatctt taaattcatc | 360 |
| attcctaata ttgtaaaata cagcccaaat tgcaagttgc ttgttgtttc caatccagtc | 420 |
| gatatttga cctatgtggc ttggaagata agtggctttc ccaaaaaccg tgttattgga | 480 |
| agtggttgca atctggattc agctcgcttc cgttatctca tggggagag ctgggagtt | 540 |
| cacccattaa gctgccatgg gtggatcctt ggggagcatg gtgactctag tgtgcctgta | 600 |
| tggagtggag tgaatgttgc tggtgtctcc ctgaagaatt tacaccctga attaggcact | 660 |
| gatgcagata aggaacagtg gaaagcggtt cacaaacaag tggttgacag tgcttatgag | 720 |
| gtgatcaaac tgaaaggcta cacatcctgg gccattggac tgtcagtggc cgatttggca | 780 |
| gaaagtataa tgaagaatct taggcgggtg catccgattt ccaccatgat taagggtctc | 840 |
| tatgaataa aagaggatgt cttccttagt gttccttgca tcttgggaca gaatggaatc | 900 |
| tcagacgttg tgaaagtgac tctgactcat gaagaagagg cctgtttgaa gaagagtgca | 960 |
| gatacacttt gggggatcca gaaagaactg cagttttaa | 999 |

<210> SEQ ID NO 36
<211> LENGTH: 1575
<212> TYPE: DNA
<213> ORGANISM: Artificial sequence
<220> FEATURE:
<223> OTHER INFORMATION: Synthesized: pct

<400> SEQUENCE: 36

```
atgagaaagg ttcccattat taccgcagat gaggctgcaa agcttattaa agacggtgat      60
acagttacaa caagtggttt cgttggaaat gcaatccctg aggctcttga tagagctgta     120
gaaaaaagat tcttagaaac aggcgaaccc aaaaacatta catatgttta ttgtggttct     180
caaggtaaca gagacggaag aggtgctgag cactttgctc atgaaggcct tttaaaacgt     240
tacatcgctg gtcactgggc tacagttcct gctttgggta aaatggctat ggaaaataaa     300
atggaagcat ataatgtatc tcagggtgca ttgtgtcatt tgttccgtga tatagcttct     360
cataagccag gcgtatttac aaaggtaggt atcggtactt tcattgaccc agaaatggc      420
ggcggtaaag taatgatat taccaaagaa gatattgttg aattggtaga gattaagggt      480
caggaatatt tattctaccc tgcttttcct attcatgtag ctcttattcg tggtacttac     540
gctgatgaaa gcggaaatat cacatttgag aaagaagttg ctcctctgga aggaacttca     600
gtatgccagg ctgttaaaaa cagtggcggt atcgttgtag ttcaggttga agagtagta      660
aaagctggta ctcttgaccc tcgtcatgta aaagttccag gaattatgt tgactatgtt      720
gttgttgctg acccagaaga tcatcagcaa tctttagatt gtgaatatga tcctgcatta     780
tcaggcgagc atagaagacc tgaagttgtt ggagaaccac ttccttgag tgcaaagaaa      840
gttattggtc gtcgtggtgc cattgaatta gaaaaagatg ttgctgtaaa tttaggtgtt     900
ggtgcgcct aatatgtagc aagtgttgct gatgaagaag gtatcgttga ttttatgact      960
ttaactgctg aaagtggtgc tattggtggt gttcctgctg gtggcgttcg ctttggtgct    1020
tcttataatg cggatgcatt gatcgatcaa ggttatcaat tcgattacta tgatggcggc    1080
ggcttagacc tttgctattt aggcttagct gaatgcgatg aaaaaggcaa tatcaacgtt    1140
tcaagatttg gccctcgtat cgctggttgt ggtggtttca tcaacattac acagaataca    1200
cctaaggtat tcttctgtgg tactttcaca gcaggtggct aaaggttaa aattgaagat     1260
ggcaaggtta ttattgttca agaaggcaag cagaaaaaat tcttgaaagc tgttgagcag    1320
attacattca atggtgacgt tgcacttgct aataagcaac aagtaactta tattacagaa    1380
agatgcgtat tccttttgaa ggaagatggt ttgcacttat ctgaaattgc acctggtatt    1440
gatttgcaga cacagattct tgacgttatg gattttgcac ctattattga cagagatgca    1500
aacggccaaa tcaaattgat ggacgctgct ttgtttgcag aaggcttaat gggtctgaag    1560
gaaatgaagt cctga                                                     1575
```

<210> SEQ ID NO 37
<211> LENGTH: 2142
<212> TYPE: DNA
<213> ORGANISM: Artificial sequence
<220> FEATURE:
<223> OTHER INFORMATION: Synthesized: ACS1

<400> SEQUENCE: 37

```
atgtcgccct ctgccgtaca atcatcaaaa ctagaagaac agtcaagtga aattgacaag      60
ttgaaagcaa aaatgtccca gtctgccgcc actgcgcagc agaagaagga acatgagtat     120
gaacatttga cttcggtcaa gatcgtgcca caacggccca tctcagatag actgcagccc     180
gcaattgcta cccactattc tccacacttg gacgggttgc aggactatca gcgcttgcac     240
aaggagtcta ttgaagaccc tgctaagttc ttcggttcta agctaccca attttttaaac    300
tggtctaagc cattcgataa ggtgttcatc ccagacccta aacgggcag gccctccttc     360
cagaacaatg catggttcct caacggccaa ttaaacgcct gttacaactg tgttgacaga    420
```

```
catgccttga agactcctaa caagaaagcc attattttcg aaggtgacga gcctggccaa      480
ggctattcca ttacctacaa ggaactactt gaagaagttt gtcaagtggc acaagtgctg      540
acttactcta tgggcgttcg caagggcgat actgttgccg tgtacatgcc tatggtccca      600
gaagcaatca taaccttgtt ggccatttcc cgtatcggtg ccattcactc cgtagtcttt      660
gccgggtttt cttccaactc cttgagagat cgtatcaacg atgggactc taaagttgtc       720 atcactacag atgaatccaa cagaggtggt aaagtcattg agactaaaag aattgttgat      780
gacgcgctaa gagagacccc aggcgtgaga cacgtcttgg tttatagaaa gaccaacaat      840
ccatctgttg ctttccatgc ccccagagat ttggattggg caacagaaaa gaagaaatac      900
aagacctact atccatgcac acccgttgat tctgaggatc cattattctt gttgtatacg      960
tctggttcta ctggtgcccc caagggtgtt caacattcta ccgcaggtta cttgctggga     1020
gctttgttga ccatgcgcta cactttgac actcaccaag aagacgtttt cttcacagct      1080
ggagacattg ctggattac aggccacact tatgtggttt atggtccctt actatatggt       1140
tgtgccactt tggtctttga agggactcct gcgtacccaa attactcccg ttattgggat     1200
attattgatg aacacaaagt cacccaattt tatgttgcgc caactgcttt gcgtttgttg     1260
aaaagagctg tgattcctca tcgaaaat cattccttaa atctttgcg ttgcttgggt         1320 tcggtcggtg agccaattgc tgctgaagtt tgggagtggt actctgaaaa aataggtaaa     1380
aatgaaatcc ccattgtaga cacctactgg caaacagaat ctggttcgca tctggtcacc     1440
ccgctggctg tggtgttac accaatgaaa ccgggttctg cctcattccc cttcttcggt      1500
attgatgcag ttgttcttga ccctaacact ggtgaagaac ttaacaccag ccacgcagag     1560
ggtgtccttg ccgtcaaagc tgcatggcca tcatttgcaa gaactatttg gaaaaatcat     1620
gataggtatc tagacactta tttgaaccct taccctggct actatttcac tggtgatggt     1680
gctgcaaagg ataaggatgg ttatatctgg attttgggtc gtgtagacga tgtggtgaac     1740
gtctctggtc accgtctgtc taccgctgaa attgaggctg ctattatcga agatccaatt     1800
gtggccgagt gtgctgttgt cggattcaac gatgacttga ctggtcaagc agttgctgca     1860
tttgtggtgt tgaaaaacaa atctagttgg tccaccgcaa cagatgatga attacaagat     1920
atcaagaagc atttggtctt tactgttaga aaagacatcg gccatttgc cgcaccaaaa      1980 ttgatcattt tagtggatga cttgcccaag acaagatccg gcaaaattat gagacgtatt     2040
ttaagaaaaa tcctagcagg agaaagtgac caactaggcg acgtttctac attgtcaaac     2100
cctggcattg ttagacatct aattgattcg gtcaagttgt aa                        2142
```

<210> SEQ ID NO 38
<211> LENGTH: 1395
<212> TYPE: DNA
<213> ORGANISM: Artificial sequence
<220> FEATURE:
<223> OTHER INFORMATION: Synthesized: pduP

<400> SEQUENCE: 38

```
atgaatactt ctgaactcga aaccctgatt cgcaccattc ttagcgagca attaaccacg       60
ccggcgcaaa cgccggtcca gcctcagggc aaagggattt ccagtccgt gagcgaggcc       120 atcgacgccg cgcaccaggc gttcttacgt tatcagcagt gcccgctaaa aacccgcagc     180
gccattatca gcgcgatgcg tcaggagctg acgccgctgc tggcgcccct ggcggaagag     240
agcgccaatg aaacggggat gggcaacaaa gaagataaat ttctcaaaaa caaggctgcg     300
ctggacaaca cgccgggcgt agaagatctc accaccaccg cgctgaccgg cgacggcggc     360
```

```
atggtgctgt ttgaatactc accgtttggc gttatcggtt cggtcgcccc aagcaccaac      420
ccgacggaaa ccatcatcaa caacagtatc agcatgctgg cggcgggcaa cagtatctac      480
tttagcccgc atccgggagc gaaaaaggtc tctctgaagc tgattagcct gattgaagag      540
attgccttcc gctgctgcgg catccgcaat ctggtggtga ccgtggcgga acccaccttc      600
gaagcgaccc agcagatgat ggcccacccg cgaatcgcag tactggccat taccggcggc      660
ccgggcattg tggcaatggg catgaagagc ggtaagaagg tgattggcgc tggcgcgggt      720
aacccgccct gcatcgttga tgaaacggcg gacctggtga agcggcggga agatatcatc      780
aacggcgcgt cattcgatta caacctgccc tgcattgccg agaagagcct gatcgtagtg      840
gagagtgtcg ccgaacgtct ggtgcagcaa atgcaaacct tcggcgcgct gctgttaagc      900
cctgccgata ccgacaaact ccgcgccgtc tgcctgcctg aaggccaggc gaataaaaaa      960
ctggtcggca gagcccatc  ggccatgctg gaagccgccg ggatcgctgt ccctgcaaaa     1020
gcgccgcgtc tgctgattgc gctggttaac gctgacgatc cgtgggtcac cagcgaacag     1080
ttgatgccga tgctgccagt ggtaaaagtc agcgatttcg atagcgcgct ggcgctggcc     1140
ctgaaggttg aagaggggct gcatcatacc gccattatgc actcgcagaa cgtgtcacgc     1200
ctgaacctcg cggcccgcac gctgcaaacc tcgatattgt caaaaacgg ccctctcttat     1260 gccgggatcg gcgtcggcgg cgaaggcttt accaccttca ctatcgccac accaaccggt     1320
gaagggacca cgtcagcgcg tacttttgcc cgttcccggc gctgcgtact gaccaacggc     1380
ttttctattc gctaa                                                     1395
```

<210> SEQ ID NO 39
<211> LENGTH: 1149
<212> TYPE: DNA
<213> ORGANISM: Artificial sequence
<220> FEATURE:
<223> OTHER INFORMATION: Synthesized: fucO

<400> SEQUENCE: 39

```
atggctaaca gaatgattct gaacgaaacg gcatggtttg gtcggggtgc tgttggggct       60
ttaaccgatg aggtgaaacg ccgtggttat cagaaggcgc tgatcgtcac cgataaaacg      120
ctggtgcaat gcggcgtggt ggcgaaagtg accgataaga tggatgctgc agggctggca      180
tgggcgattt acgacggcgt agtgcccaac ccaacaatta ctgtcgtcaa agaagggctc      240
ggtgtattcc agaatagcgg cgcggattac ctgatcgcta ttggtggtgg ttctccacag      300
gatacttgta aagcgattgg cattatcagc aacaacccgg agtttgccga tgtgcgtagc      360
ctggaagggc tttccccgac caataaaccc agtgtaccga ttctggcaat tcctaccaca      420
gcaggtactg cggcagaagt gaccattaac tacgtgatca ctgacgaaga gaaacggcgc      480
aagtttgttt gcgttgatcc gcatgatatc ccgcaggtgg cgtttattga cgctgacatg      540
atggatggta tgcctccagc gctgaaagct gcgacgggtg tcgatgcgct cactcatgct      600 attgagggt  atattacccg tggcgcgtgg gcgctaaccg atgcactgca cattaaagcg      660
attgaaatca ttgctggggc gctgcgagga tcggttgctg gtgataagga tgccggagaa      720
gaaatggcgc tcgggcagta tgttgcgggt atgggcttct cgaatgttgg gttagggttg      780
gtgcatggta tggcgcatcc actgggcgcg ttttataaca ctccacacgg tgttgcgaac      840
gccatcctgt taccgcatgt catgcgttat aacgctgact ttaccggtga agtaccgc       900 gatatcgcgc gcgttatggg cgtgaaagtg aaggtatga gcctggaaga ggcgcgtaat      960
gccgctgttg aagcggtgtt tgctctcaac cgtgatgtcg gtattccgcc acatttgcgt     1020
```

```
gatgttggtg tacgcaagga agacattccg gcactggcgc aggcggcact ggatgatgtt    1080
tgtaccggtg caacccgcg tgaagcaacg cttgaggata ttgtagagct ttaccatacc    1140
gcctggtaa                                                            1149
```

<210> SEQ ID NO 40
<211> LENGTH: 10
<212> TYPE: PRT
<213> ORGANISM: Artificial sequence
<220> FEATURE:
<223> OTHER INFORMATION: Synthesized: ATOA_ECOLI catalytic GLU location

<400> SEQUENCE: 40

```
Ile Thr Leu Gln Ser Glu Asn Gly Phe Leu
1               5                   10
```

<210> SEQ ID NO 41
<211> LENGTH: 10
<212> TYPE: PRT
<213> ORGANISM: Artificial sequence
<220> FEATURE:
<223> OTHER INFORMATION: Synthesized: ITLQSENGFL catalytic GLU location

<400> SEQUENCE: 41

```
Ile Thr Leu Gln Ser Glu Asn Gly Phe Leu
1               5                   10
```

<210> SEQ ID NO 42
<211> LENGTH: 10
<212> TYPE: PRT
<213> ORGANISM: Artificial sequence
<220> FEATURE:
<223> OTHER INFORMATION: Synthesized: CATJ_PSESB catalytic GLU location

<400> SEQUENCE: 42

```
Val Val Leu Ile Tyr Glu Ser Gly Pro Ile
1               5                   10
```

<210> SEQ ID NO 43
<211> LENGTH: 10
<212> TYPE: PRT
<213> ORGANISM: Artificial sequence
<220> FEATURE:
<223> OTHER INFORMATION: Synthesized: CTFB_CLOAB catalytic GLU location

<400> SEQUENCE: 43

```
Ile Thr Phe Gln Ser Glu Asn Gly Ile Val
1               5                   10
```

<210> SEQ ID NO 44
<211> LENGTH: 10
<212> TYPE: PRT
<213> ORGANISM: Artificial sequence
<220> FEATURE:
<223> OTHER INFORMATION: Synthesized: GCTB_ACIFV catalytic GLU location

<400> SEQUENCE: 44

```
Cys His Ile Ile Val Glu Ser Gly Leu Met
1               5                   10
```

<210> SEQ ID NO 45
<211> LENGTH: 10
<212> TYPE: PRT
<213> ORGANISM: Artificial sequence
<220> FEATURE:
<223> OTHER INFORMATION: Synthesized: PCAJ_ACIAD catalytic GLU location

```
<400> SEQUENCE: 45

Val Phe Leu His Ser Glu Asn Gly Leu Leu
1               5                   10

<210> SEQ ID NO 46
<211> LENGTH: 10
<212> TYPE: PRT
<213> ORGANISM: Artificial sequence
<220> FEATURE:
<223> OTHER INFORMATION: Synthesized: PCAJ_PSEPK catalytic GLU location

<400> SEQUENCE: 46

Val Phe Leu His Ser Glu Asn Gly Leu Leu
1               5                   10

<210> SEQ ID NO 47
<211> LENGTH: 10
<212> TYPE: PRT
<213> ORGANISM: Artificial sequence
<220> FEATURE:
<223> OTHER INFORMATION: Synthesized: PCAJ_PSEPU catalytic GLU location

<400> SEQUENCE: 47

Val Phe Leu His Ser Glu Asn Gly Leu Leu
1               5                   10

<210> SEQ ID NO 48
<211> LENGTH: 10
<212> TYPE: PRT
<213> ORGANISM: Artificial sequence
<220> FEATURE:
<223> OTHER INFORMATION: Synthesized: SCOB_BACSU catalytic GLU location

<400> SEQUENCE: 48

Val Met Leu Gln Ser Glu Asn Gly Leu Leu
1               5                   10

<210> SEQ ID NO 49
<211> LENGTH: 10
<212> TYPE: PRT
<213> ORGANISM: Artificial sequence
<220> FEATURE:
<223> OTHER INFORMATION: Synthesized: SCOB_HELPJ catalytic GLU location

<400> SEQUENCE: 49

Ile Val Phe Gln Ser Glu Asn Gly Leu Leu
1               5                   10

<210> SEQ ID NO 50
<211> LENGTH: 10
<212> TYPE: PRT
<213> ORGANISM: Artificial sequence
<220> FEATURE:
<223> OTHER INFORMATION: Synthesized: SCOB_HELPY catalytic GLU location

<400> SEQUENCE: 50

Ile Val Phe Gln Ser Glu Asn Gly Leu Leu
1               5                   10

<210> SEQ ID NO 51
<211> LENGTH: 10
<212> TYPE: PRT
<213> ORGANISM: Artificial sequence
<220> FEATURE:
<223> OTHER INFORMATION: Synthesized: SCOB_MYCBO catalytic GLU location
```

```
<400> SEQUENCE: 51

Val Val Leu His Ser Glu Asn Gly Ile Leu
1               5                   10

<210> SEQ ID NO 52
<211> LENGTH: 10
<212> TYPE: PRT
<213> ORGANISM: Artificial sequence
<220> FEATURE:
<223> OTHER INFORMATION: Synthesized: SCOB_MYCTU catalytic GLU location

<400> SEQUENCE: 52

Val Val Leu His Ser Glu Asn Gly Ile Leu
1               5                   10

<210> SEQ ID NO 53
<211> LENGTH: 10
<212> TYPE: PRT
<213> ORGANISM: Artificial sequence
<220> FEATURE:
<223> OTHER INFORMATION: Synthesized: SCOB_XANCB catalytic GLU location

<400> SEQUENCE: 53

Val Trp Leu Gln Ser Glu Asn Gly Leu Leu
1               5                   10

<210> SEQ ID NO 54
<211> LENGTH: 10
<212> TYPE: PRT
<213> ORGANISM: Artificial sequence
<220> FEATURE:
<223> OTHER INFORMATION: Synthesized: SCOB_XANCP catalytic GLU location

<400> SEQUENCE: 54

Val Trp Leu Gln Ser Glu Asn Gly Leu Leu
1               5                   10

<210> SEQ ID NO 55
<211> LENGTH: 10
<212> TYPE: PRT
<213> ORGANISM: Artificial sequence
<220> FEATURE:
<223> OTHER INFORMATION: Synthesized: Y3552_MYCTU catalytic GLU location

<400> SEQUENCE: 55

Ile Leu Leu Thr Asp Gly Glu Ala Gln Leu
1               5                   10

<210> SEQ ID NO 56
<211> LENGTH: 10
<212> TYPE: PRT
<213> ORGANISM: Artificial sequence
<220> FEATURE:
<223> OTHER INFORMATION: Synthesized: Y3582_MYCBO catalytic GLU location

<400> SEQUENCE: 56

Ile Leu Leu Thr Asp Gly Glu Ala Gln Leu
1               5                   10

<210> SEQ ID NO 57
<211> LENGTH: 10
<212> TYPE: PRT
<213> ORGANISM: Artificial sequence
<220> FEATURE:
<223> OTHER INFORMATION: Synthesized: YODR_BACSU catalytic GLU location
```

```
<400> SEQUENCE: 57

Val Met Phe Gln Ala Glu Asn Gly Val Leu
1               5                   10

<210> SEQ ID NO 58
<211> LENGTH: 10
<212> TYPE: PRT
<213> ORGANISM: Artificial sequence
<220> FEATURE:
<223> OTHER INFORMATION: Synthesized: YDIF ECOLI catalytic GLU location

<400> SEQUENCE: 58

Phe Ile Leu Thr Val Glu Thr Gly Pro Ile
1               5                   10
```